(12) United States Patent
Chee et al.

(10) Patent No.: US 11,753,677 B2
(45) Date of Patent: Sep. 12, 2023

(54) METHODS FOR BARCODING MACROMOLECULES IN INDIVIDUAL CELLS

(71) Applicant: Encodia, Inc., San Diego, CA (US)

(72) Inventors: Mark S. Chee, Encinitas, CA (US);
Haibiao Gong, San Diego, CA (US);
Kevin L. Gunderson, Encinitas, CA (US)

(73) Assignee: Encodia, Inc., San Diego, CA (US)

( * ) Notice: Subject to any disclaimer, the term of this patent is extended or adjusted under 35 U.S.C. 154(b) by 0 days.

(21) Appl. No.: 17/984,207

(22) Filed: Nov. 9, 2022

(65) Prior Publication Data

US 2023/0143290 A1 May 11, 2023

Related U.S. Application Data

(60) Provisional application No. 63/278,045, filed on Nov. 10, 2021.

(51) Int. Cl.
*C12Q 1/68* (2018.01)
*C12Q 1/6841* (2018.01)
(Continued)

(52) U.S. Cl.
CPC ......... *C12Q 1/6841* (2013.01); *C12Q 1/6806* (2013.01); *C12Q 1/6858* (2013.01);
(Continued)

(58) Field of Classification Search
CPC ...................................................... C12Q 1/68
(Continued)

(56) References Cited

U.S. PATENT DOCUMENTS 5,447,841 A 9/1995 Gray et al.
5,948,617 A 9/1999 Utermohlen et al.
(Continued)

FOREIGN PATENT DOCUMENTS

WO 2020247685 A2 12/2020
WO 2021097250 A2 5/2021
WO 2022072560 A1 4/2022

OTHER PUBLICATIONS

Cheng, J. et al. (Sep. 2021). "Multiplexing Methods for Simultaneous Large-Scale Transcriptomic Profiling of Samples at Single-Cell Resolution," Adv Sci (Weinh). 8(17): e2101229, 14 pages.
(Continued)

*Primary Examiner* — Aaron A Priest
(74) *Attorney, Agent, or Firm* — MORRISON & FOERSTER LLP

(57) ABSTRACT

The present disclosure relates to methods and kits for generating single cell barcodes and imparting them to the constituent molecules within a single cell. Additionally, methods to overlay sample barcode and spatial barcode information onto the single cell barcodes are also described. Generation of single cell barcodes is achieved by labeling the genomic DNA of a cell/nucleus with a small handful, preferably just a one or two cellular barcode probes (CBP) that can be amplified and propagated to label the constituent molecules within the cell. The disclosure finds utility in applications such as characterization of cellular heterogeneity, comprehensive profiling of tissue composition, characterization of adherent cells, discovery of new cell subtypes and functions of individual cells in the context of its microenvironment, and others.

22 Claims, 25 Drawing Sheets

Specification includes a Sequence Listing.

(51) Int. Cl.
*C12Q 1/6858* (2018.01)
*C12Q 1/6806* (2018.01)
(52) U.S. Cl.
CPC . *C12Q 2600/154* (2013.01); *C12Q 2600/156* (2013.01); *C12Q 2600/16* (2013.01)
(58) Field of Classification Search
USPC ........................................................ 435/6.12
See application file for complete search history.

(56) References Cited

U.S. PATENT DOCUMENTS

| | | |
|---|---|---|
| 7,115,400 B1 | 10/2006 | Adessi et al. |
| 7,241,573 B2 | 7/2007 | Choo et al. |
| 7,888,121 B2 | 2/2011 | Urnov et al. |
| 8,119,381 B2 | 2/2012 | Smith et al. |
| 8,163,514 B2 | 4/2012 | Smith et al. |
| 8,236,949 B2 | 8/2012 | Fox et al. |
| 8,420,782 B2 | 4/2013 | Bonas et al. |
| 8,440,431 B2 | 5/2013 | Voytas et al. |
| 8,440,432 B2 | 5/2013 | Voytas et al. |
| 8,697,853 B2 | 4/2014 | Voytas et al. |
| 8,771,945 B1 | 7/2014 | Zhang |
| 8,906,607 B2 | 12/2014 | Duchateau et al. |
| 8,921,112 B2 | 12/2014 | Cai et al. |
| 9,169,283 B2 | 10/2015 | Wiessler et al. |
| 9,187,758 B2 | 11/2015 | Cai et al. |
| 9,303,287 B2 | 4/2016 | Matthiesen |
| 9,309,562 B2 | 4/2016 | Matthiesen |
| 9,315,788 B2 | 4/2016 | Duchateau et al. |
| 9,388,456 B2 | 7/2016 | Matthiesen |
| 9,393,257 B2 | 7/2016 | Osborn et al. |
| 9,499,592 B2 | 11/2016 | Zhang et al. |
| 9,695,432 B2 | 7/2017 | Russell et al. |
| 9,696,247 B2 | 7/2017 | Goldsborough et al. |
| 10,144,950 B2 | 12/2018 | Nolan |
| 10,202,638 B2 | 2/2019 | Matthiesen |
| 10,344,329 B2 | 7/2019 | Hindson et al. |
| 10,428,326 B2 | 10/2019 | Belhocine et al. |
| 10,442,789 B2 | 10/2019 | Yang et al. |
| 10,611,738 B2 | 4/2020 | Hilderbrand et al. |
| 10,697,974 B2 | 6/2020 | Woo et al. |
| 10,752,895 B2 | 8/2020 | Church et al. |
| 10,767,168 B2 | 9/2020 | Joung et al. |
| 10,774,370 B2 | 9/2020 | Zheng et al. |
| 10,815,525 B2 | 10/2020 | Lucero et al. |
| 10,858,639 B2 | 12/2020 | Liu et al. |
| 10,876,107 B2 | 12/2020 | Vigneault et al. |
| 11,124,782 B2 | 9/2021 | Liu et al. |
| 11,427,814 B2 | 8/2022 | Desai et al. |
| 11,441,179 B2 | 9/2022 | Hindson et al. |
| 2015/0148239 A1 | 5/2015 | Peter et al. |
| 2016/0257984 A1 | 9/2016 | Hardenbol et al. |
| 2016/0369268 A1 | 12/2016 | Bleris et al. |
| 2017/0268056 A1* | 9/2017 | Vigneault ............ C12Q 1/6881 |
| 2018/0273933 A1 | 9/2018 | Gunderson et al. |
| 2018/0355348 A1 | 12/2018 | Adey et al. |
| 2019/0032128 A1 | 1/2019 | Chen et al. |
| 2019/0040382 A1 | 2/2019 | Steemers et al. |
| 2019/0145982 A1* | 5/2019 | Chee .................. G01N 33/6845 435/6.11 |
| 2019/0276818 A1 | 9/2019 | Gehring et al. |
| 2019/0330678 A1 | 10/2019 | Singer et al. |
| 2020/0261879 A1 | 8/2020 | Abate et al. |
| 2020/0270632 A1 | 8/2020 | Roy et al. |
| 2020/0277663 A1* | 9/2020 | Ramachandran Iyer ................... G01N 21/6458 |
| 2020/0348307 A1 | 11/2020 | Beierle et al. |
| 2020/0348308 A1* | 11/2020 | Chee .................. C12Q 1/6804 |
| 2020/0385785 A1* | 12/2020 | Chen .................. C12Q 1/6806 |
| 2021/0079557 A1 | 3/2021 | Pawlosky et al. |
| 2021/0123103 A1 | 4/2021 | Schnall-levin et al. |
| 2021/0208150 A1 | 7/2021 | Gunderson et al. |
| 2022/0049246 A1 | 2/2022 | Chee et al. |
| 2022/0283175 A1 | 9/2022 | Okerberg et al. |
| 2022/0403452 A1 | 12/2022 | Lance et al. |

OTHER PUBLICATIONS

Liu, Y. et al. (Dec. 10, 2020). "High-Spatial-Resolution Multi-Omics Sequencing via Deterministic Barcoding in Tissue," Cell 183(6):1665-1681e.18, 39 pages.
Matsunaga, S. et al. (2017). "FISH with Padlock Probes Can Efficiently Reveal the Genomic Position of Low or Single-Copy DNA Sequences," Cytologia 82(4):337-339.
Reimegård, J. et al. (May 25, 2021). "A Combined Approach For Single-Cell Mrna And Intracellular Protein Expression Analysis," Commun Biol. 4(1):624, 11 pages.
Srivatsan, S.R. et al. (Jul. 2, 2021). "Embryo-Scale, Single-Cell Spatial Transcriptomics," Science 373 (6550):111-117, 8 pages.
International Search Report and Written Opinion of the International Search Authority dated Mar. 9, 2023, for PCT Application No. PCT/US2022/079584, filed on Nov. 9, 2022, 15 pages.

* cited by examiner

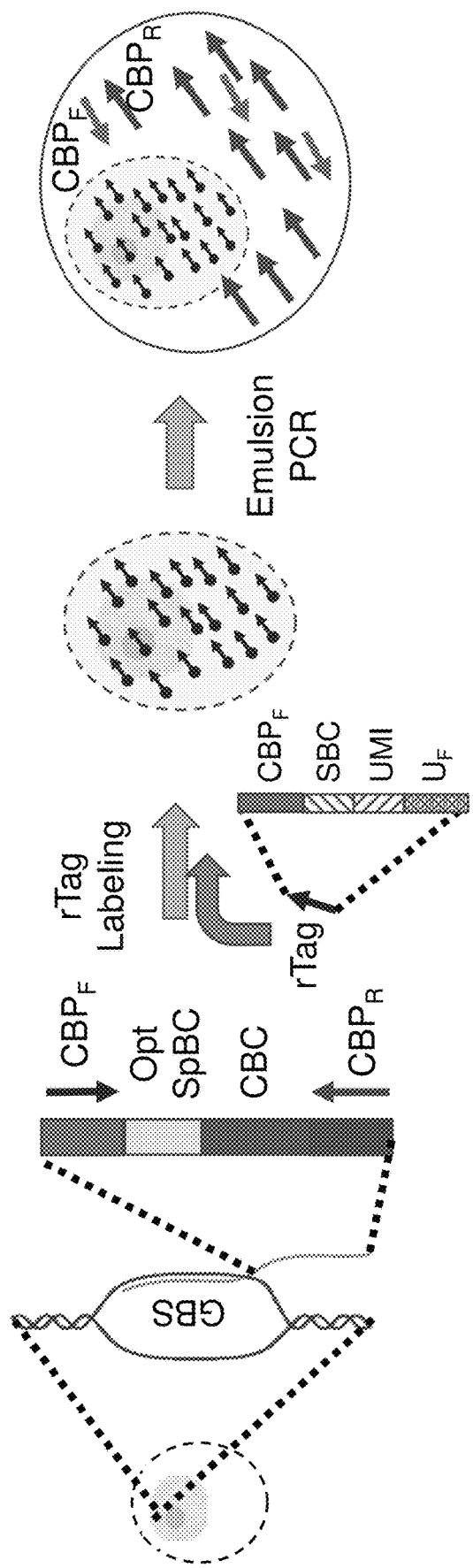

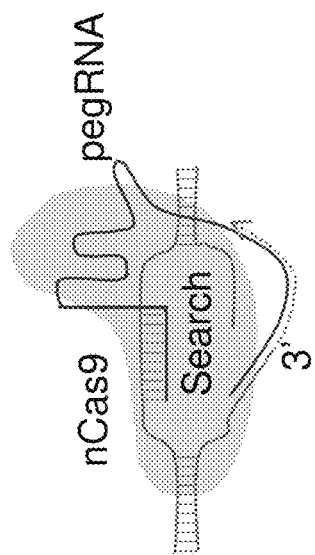
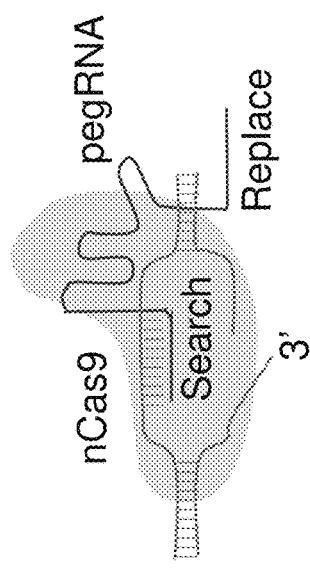
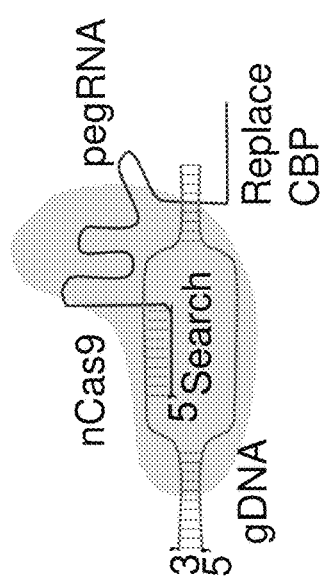
Fig. 9C
Fig. 9B
Fig. 9A

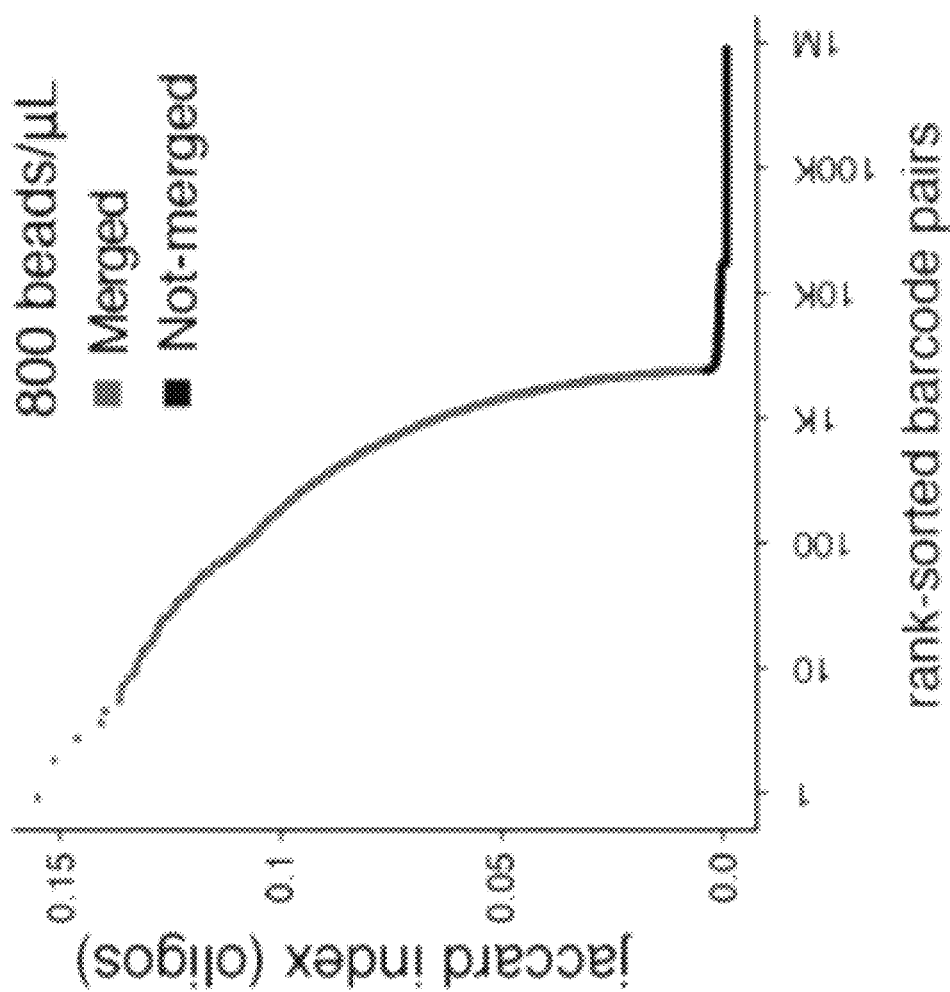

METHODS FOR BARCODING MACROMOLECULES IN INDIVIDUAL CELLS

CROSS-REFERENCE TO RELATED APPLICATION

This application claims priority to U.S. Provisional Patent Application No. 63/278,045 filed Nov. 10, 2021, entitled "METHODS FOR BARCODING MACROMOLECULES IN INDIVIDUAL CELLS," which is herein incorporated by reference in its entirety for all purposes.

REFERENCE TO AN ELECTRONIC SEQUENCE LISTING

The contents of the electronic sequence listing (776532003800SEQLIST.xml; Size: 16,666 bytes; and Date of Creation: Nov. 9, 2022) is herein incorporated by reference in its entirety.

TECHNICAL FIELD

The present disclosure relates to biotechnology, and in some aspects to methods and kits for barcoding macromolecules in individual cells using cell barcode probes (CBPs) that comprise a common genome binding element and a cell barcode. In some embodiments, the disclosure finds utility in applications such as characterization of cellular heterogeneity, comprehensive profiling of tissue composition, characterization of adherent cells, discovery of new cell subtypes and/or functions of individual cells in the context of its microenvironment, and others.

BACKGROUND

It has been increasingly accepted that seemingly homogeneous tissues or cell populations exhibit heterogeneity in gene expression and protein levels. In some situations, such as during cancer cell evolution, the DNA mutation and methylation profiles also differ among individual cells. Therefore, the ability to analyze DNA, RNA and protein at single cell resolution is of great importance. Traditionally single cell mRNA and protein expression have been examined by fluorescent in situ hybridization with a microscope (Kalisky, T. and Quake, S. R. (2011) Single cell genomics. *Nat Methods*, 8, 311-314) and flow cytometer (Wu, M. and Singh, A. K. (2012) Single cell protein analysis. *Curr Opin Biotechnol*, 23, 83-88), respectively. More recently, qPCR was employed for single cell mRNA analysis (Dalerba, P., et al. (2011) Single cell dissection of transcriptional heterogeneity in human colon tumors. *Nat Biotechnol*, 29, 1120-1127). However, to obtain a more comprehensive understanding of the complex molecular networks in the living cell, a highly multiplexed approach is necessary. There remains a need for improved techniques relating to multiplexing DNA, RNA and protein molecules as well as kits for accomplishing the same. The present disclosure addresses these and other needs.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

Next-generation sequencing (NGS) can be used for single cell analysis. The first single cell mRNA sequencing (mRNA-seq) study was published in 2009 (Tang, F., et al. (2009) mRNA-Seq whole-transcriptome analysis of a single cell. *Nat Methods*, 6, 377-382). Since then, this field has been revolutionized and various commercial single cell platforms have been developed including: Fluidigm C1 (Pollen, A. A., et al. (2014) Low-coverage single cell mRNA sequencing reveals cellular heterogeneity and activated signaling pathways in developing cerebral cortex. *Nat Biotechnol*, 32, 1053-1058, and Gong, H., et al. (2017) Single cell protein-mRNA correlation analysis enabled by multiplexed dual-analyte co-detection. *Sci Rep*, 7, 2776); 10× Chromium (Zheng, G. X., et al. (2017); Massively parallel digital transcriptional profiling of single cells. *Nat Commun*, 8, 14049); Mission Bio Tapestri (Demaree, B., et al. (2021); Joint profiling of DNA and proteins in single cells to dissect genotype-phenotype associations in leukemia. *Nat Commun*, 12, 1583); and B D Rhapsody (Mair, F., (2020) et al. A Targeted Multi-omic Analysis Approach Measures Protein Expression and Low-Abundance Transcripts on the Single cell Level. *Cell Rep*, 31, 107499). Moreover, high throughput single cell analysis protocols that do not rely on a dedicated single cell platforms but employ bulk processes to combinatorically barcode cell populations with single cell resolution have been developed including: SPLiT-seq (Rosenberg, A. B., et al. (2018) Single cell profiling of the developing mouse brain and spinal cord with split-pool barcoding. *Science*, 360, 176-182); and sci-RNA-seq (Cao, J., et al. (2017) Comprehensive single cell transcriptional profiling of a multicellular organism. *Science*, 357, 661-667).

Analyzing tissues and cells at single cell level can be used for a variety of applications such as characterization of cellular heterogeneity, profiling of tissue composition, discovery of new cell subtypes, characterization of adherent cell types such as from a fluid biopsy with relevant circulating tumor cells (CTCs) (Marrinucci, et al., 2012. "Fluid Biopsy in Patients with Metastatic Prostate, Pancreatic and Breast Cancers." *Physical Biology* 9 (1): 016003), identification of novel marker genes, investigation of allelic expression patterns, dissection of gene-regulatory networks, study of T cell fate and clonality, and even production of cellular maps of entire cell lineages, organs and organisms (Mereu, E., et al. (2020) Benchmarking single cell RNA-sequencing protocols for cell atlas projects. *Nat Biotechnol*, 38, 747-755). Thiele et al. describe the use of adherent high-density single cell analysis (HD-SCA) using both cell-staining based morphological analysis combined with single-cell genomic analysis to characterized subpopulations with relevance to cancer outcomes (Thiele, et al., 2019. "Single-Cell Analysis of Circulating Tumor Cells." *Methods in Molecular Biology* 1908: 243-64). Adherent cell sample slides can also be created by using a "touch prep" in which a resected tumor tissue or biopsy specimen is lightly touched to the surface of a slide leaving a layer of tumor and associated cells on the surface of the slide in the context of preserving spatial information (Thiele et al., 2019).

The multi-omic analysis of CTCs in a collection of adherent cells such as derived from a fluid biopsy is instrumental in providing diagnostic and prognostic information on tumor development and progression. In some embodiments, adherent cells can provide both phenotypic information derived from cell (e.g., staining with dyes and fluorescent antibodies), and molecular information derived from multi-omic analysis, e.g., as described in the present disclosure. In some embodiments, methods and compositions disclosed herein can be used for characterizing CTC heterogeneity in a fluid biopsy and understanding its impact on cancer progression.

Comprehensive analyses of heterogeneous cell populations require development of simple and efficient methods for barcoding macromolecules in individual cells. In some embodiments, provided herein are methods, compositions, and kits for multiplexing analytes, such as DNA, RNA and protein molecules. In some embodiments, analytes are barcoded at cellular level. In some embodiments, the single cell barcoding methods disclosed herein can allow multiple analytes (e.g., DNA, RNA and protein) from each single cell to be barcoded in a single assay with a cell-specific barcode. The barcoding methods disclosed herein may be utilized in a wide variety of nucleic acid-based and/or protein-based procedures. In some embodiments, the present disclosure provides molecular analysis using single cell barcoding described herein for single cell multi-omic analysis including genomic, transcriptomic, and proteomic analysis a cell sample or a tissue sample, including but not limited to adherent cell samples for HD-SCA.

In some embodiments, disclosed herein is a method for barcoding macromolecules of, in, and/or form a biological sample. In some embodiments, the biological sample comprises a plurality of cells and/or nuclei. The cells and/or nuclei of the biological sample may be dissociated cells and/or nuclei, for example, generated by dissociating a tissue sample into dissociated single cells. In some embodiments, the biological sample can be a tissue sample such as a tissue section or tissue block.

In some embodiments, a method disclosed herein can comprise contacting the cells or nuclei in a biological sample with cell barcode probes or genomic DNA-binding carriers carrying cell barcodes. In some embodiments, the specific genomic DNA-binding carrier comprises a catalytically inactive Cas nuclease, a TALE protein, or a zinc-finger protein.

In some embodiments, a given cell barcode probe comprises: i) a genome binding element shared among the cell barcode probes, and ii) a cell barcode. In some embodiments, the cell barcode is unique to the given cell barcode probe and identifies the given cell barcode probe from among the cell barcode probes.

In some embodiments, the genome binding element or genomic DNA-binding carrier shared among the cell barcode probes binds to a region in the genomic DNA of the cells or nuclei. In some embodiments, the genome binding element shared among the cell barcode probes comprises a sequence that is complementary to a region in the genomic DNA (gDNA) of the cells or nuclei (e.g., the genome binding element can be complementary to a DNA strand in a non-repetitive region in the gDNA. The non-repetitive region can be a unique region compared to other regions in the gDNA, and the non-repetitive region can be shared by all or substantially all of the cells or nuclei of, in, and/or from the biological sample. In some embodiments, the genome binding element targets a specific region in the gDNA of the cells or nuclei, where each cell or nuclei comprises one or two copies of the specific region (such as in a diploid cell. In some embodiments, the given cell barcode probe further comprises a UMI that can be used to distinguish the particular cell barcode probe molecule from other cell barcode probe molecules having the same cell barcode.

In some embodiments, the cells or nuclei can be contacted with the cell barcode probes prior to, during, and/or after dissociating the biological sample into dissociated single cells and/or nuclei. In some embodiments, the method can comprise permeabilizing the cells and/or nuclei, for instance, to facilitate binding of the cell barcode probes to the genomic DNA. In some embodiments, the method can comprise making genomic DNA of the cells and/or nuclei at least partially accessible to nucleic acid hybridization, for instance, to facilitate hybridization of the genome binding element or a portion thereof to a DNA strand of a non-repetitive region in the genomic DNA. In some embodiments, the method comprises forming a nucleic acid duplex between the genome binding element and the region of the genomic DNA in the cells and/or nuclei. In some embodiments, each cell or nucleus contains no more than a defined number of copies of the non-repetitive region, such as one or two copies, thereby limiting the number of cell barcode probe molecules that can bind to the genomic DNA of each cell or nucleus.

In some embodiments, the method comprises removing molecules of cell barcode probes that are not bound or nonspecifically bound to the genomic DNA from the cells and/or nuclei, whereby no more than a defined number of cell barcode probe molecules (such as one or two molecules) remain in each cell or nucleus.

In some embodiments, the method comprises partitioning the cells and/or nuclei into a plurality of partitions (e.g., compartments, such as emulsion droplets or microwells). In some embodiments, each partition contains no more than one cell or nucleus. In some embodiments, each partition contains no more than a single cell or nucleus containing no more than two cell barcode probe molecules specifically bound to the genomic DNA of the single cell or nucleus. The no more than two cell barcode probe molecules can comprise the shared genome binding element and the cell barcode(s) unique to the cell barcode probe(s), and optionally a UMI that is unique to each cell barcode probe molecule.

In some embodiments, the method comprises amplifying the cell barcode(s) within each partition of the plurality of partitions, thereby forming amplified oligonucleotides comprising cell barcodes within the partition. Since in some embodiments for each cell or nucleus, the cell barcode(s) in the cell or nucleus are unique among the plurality of cell barcode probes (therefore distinguishing the cell or nucleus from other cells or nuclei that have received other unique cell barcodes), the cell barcode(s) can be used to uniquely identify the cell or nucleus (and components such as macromolecules thereof) from among the cells or nuclei of the biological sample.

In some embodiments, the method comprises attaching the amplified cell barcodes in each partition to the macromolecules within the partition, thereby forming barcoded macromolecules. In some embodiments, since the barcoded macromolecules comprise cell barcode(s) that can be used to uniquely identify the cell or nucleus containing the macromolecules, the barcoded macromolecules from different partitions (e.g., different single cells or nuclei) can be pooled and analyzed in a high throughput manner, comprising analyzing the cell barcodes (and optionally sample barcodes, UMIs, and/or spatial barcodes) using NGS, thereby analyzing macromolecules such as proteins of the biological sample on a single-cell level.

In some embodiments, the amplified oligonucleotides comprising cell barcodes within each partition can be reacted with nucleic acid molecules attached to macromolecules such as proteins in the partition. The reaction can comprise nucleic acid hybridization between the amplified oligonucleotides and the nucleic acid molecules attached to macromolecules, and primer extension of a nucleic acid molecule attached to a macromolecule using an amplified oligonucleotide (which comprises a cell barcode or complement thereof) as a template, thereby porting the cell barcode sequence information (and optionally the sample barcode information and/UMI) into the extended nucleic acid molecule attached to the macromolecule.

In some embodiments, provided herein are methods for generating barcodes and imparting one or more barcodes to the constituent molecules of a single cell (e.g., constituent molecules in and/or on the single cell). In some embodiments, each single cell in a cell population can be labeled with a unique barcode code (or a unique combination of barcode codes) that corresponds to the single cell and not another single cell in the population, and the unique barcode codes or combinations thereof can be referred to as single cell barcodes. Additionally, methods to overlay sample barcode and spatial barcode information onto the single cell barcodes are also described. In an exemplary embodiment, the genomic DNA of a cell is labeled, preferably in situ, with a small handful, preferably just a one or two cellular barcode probes (CBP) that can be amplified and propagated to label the constituent molecules of the cell. In some embodiments, the CBP comprises a Genome Binding Sequence (GBS) which targets the CBP probe to a specific locus within the genome by virtue of complementary hybridization of the GBS to the target locus. In some cases, this GBS sequence can be organism specific and different GBS sequences can be used for different organisms. In some embodiments, a method to enable the attachment of only one or two DNA cellular barcodes to the entire cell comprises tagging the genomic DNA (gDNA) at a single copy locus within the genome using appropriately designed CBP/GBS sequences and/or genome targeting moieties (e.g., CRISPR/Cas9, TALEs, etc.). In some embodiments, labeling of a single copy of a locus can generate two cell barcode probes (CBPs) in a single cell due to the diploid nature of the genome. In some embodiments, the CBP is designed to be attached to a gDNA locus, so that a single copy of CBP remains within cells or nuclei after nonspecifically bound CBPs are removed by washing. This can be achieved by targeting a CBP to a unique genomic polymorphism, a mutation site, or a differentially methylated region (e.g., attaching CBPs to gDNA in a methylation-specific manner). In some embodiments, the targeting locus of gDNA is not transcribed in order to prevent interference from transcribed RNA during the CBP annealing and labeling process. In some embodiments, specific targeting employs specific gDNA-binding enzyme recognition (e.g., CRISPR or TALE-based approaches) of dsDNA, which can also deliver only a single copy of CBP to each individual cell or nucleus.

In some embodiments, provided herein is a method for barcoding macromolecules (e.g., generating macromolecules comprising a barcode) from a sample comprising a population of cells, the method comprising the following steps:

a. permeabilizing cells or nuclei, and optionally fixing cells or nuclei, from the population of cells of the sample (dispersed cells, cells within a tissue, etc.);
b. optionally making genomic DNA of the permeabilized cells or nuclei at least partially accessible to nucleic acid hybridization;
c. delivering cell barcode probes to the permeabilized cells and/or nuclei of the permeabilized cells, wherein a given cell barcode probe comprises a genome binding element shared among the cell barcode probes, and a cell barcode unique for a given cell barcode probe, and wherein the genome binding element hybridizes to a region in the genomic DNA, thereby forming a nucleic acid duplex between the genome binding element and the region of the genomic DNA in the cells and/or nuclei;
d. removing cell barcode probes that are not bound to the genomic DNA from the cells or nuclei, whereby no more than a defined number of copies of the cell barcode probe remain in each cell or nucleus;
e. optionally disassociating cells within tissue, and partitioning the cells or nuclei into a plurality of compartments;
f. amplifying the cell barcodes within compartments of the plurality of compartments, thereby forming amplified cell barcodes within the compartments;
g. attaching the amplified cell barcodes to the macromolecules within the compartments, thereby forming barcoded macromolecules.

In another embodiment, provided herein is a method for barcoding macromolecules from a sample comprising a population of cells, the method comprising the following steps:

a. permeabilizing cells, or nuclei of the cells, from the population of cells of the sample;
b. delivering reactive primers that are configured to be covalently attached to components of the permeabilized cells, thereby creating a plurality of attached primers;
c. optionally making genomic DNA of the permeabilized cells or nuclei at least partially accessible to nucleic acid hybridization;
d. delivering cell barcode probes to the permeabilized cells and/or nuclei of the permeabilized cells, wherein a given cell barcode probe comprises a genome binding element shared among the cell barcode probes, and a cell barcode unique for a given cell barcode probe, and wherein the genome binding element hybridizes to a region in the genomic DNA, thereby forming a nucleic acid duplex between the genome binding element and the region of the genomic DNA in the cells and/or nuclei;
e. removing cell barcode probes that are not bound to the genomic DNA from the cells or nuclei, whereby no more than a defined number of copies of the cell barcode probe remain in each cell or nucleus;
f. amplifying the cell barcodes using the plurality of attached primers, thereby forming amplified cell barcodes within the compartments;
g. attaching the amplified cell barcodes to the macromolecules within cells, thereby forming barcoded macromolecules.

In yet another embodiment, provided herein is a method for barcoding macromolecules from a sample comprising a population of cells, the method comprising the following steps:

a. permeabilizing cells, or nuclei of the cells, from the population of cells of the sample;
b. delivering a specific genomic DNA-binding carrier comprising a cell barcode probe to the permeabilized cells or nuclei, wherein a given cell barcode probe comprises a cell barcode unique for each cell or nucleus, and a priming site, and wherein the specific genomic DNA-binding carrier specifically binds to a region in the genomic DNA of the cells or nuclei;
c. removing specific genomic DNA-binding carriers that are not bound to the genomic DNA from the cells or nuclei, whereby no more than a defined number of copies of the cell barcode probe remain in each cell or nucleus;

d. amplifying the cell barcodes that were not removed from the cells or nuclei at step (c), thereby forming amplified cell barcodes;

e. attaching the amplified cell barcodes to the macromolecules, thereby forming barcoded macromolecules.

These and other aspects or embodiments of the invention will be apparent upon reference to the following detailed description. To this end, various references are set forth herein which describe in more detail certain background information, procedures, compounds and/or compositions, and are each hereby incorporated by reference in their entireties.

BRIEF DESCRIPTION OF THE DRAWINGS

Non-limiting embodiments of the present invention will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the invention.

FIG. 2A. Exemplary flow diagram for single cell suspension multi-omics analysis using nuclei cellular barcode tagging and Emulsion PCR (ePCR). The steps in grey can be performed in any order and include protein tagging with DNA recording tag (rTags) stubs, in situ cDNA labeling, nuclear ATAC-Seq labeling, and nuclear labeling with a cellular barcode probe (CBP). After encoding, the single cells are partitioned into compartments, and ePCR is used to incorporate the CBP tag into the ATAC-Seq, RNA-Seq, and/or Prot-Seq DNA tags. These pre-library constructs are further processed to prepare scATAC-Seq, scRNA-Seq, and/or scProt-Seq libraries. For short read NGS sequencing of scRNA-Seq libraries, the cDNA library constructs can use further processing involving PCR, fragmentation, adapterization using protocols such as SMART-Seq (tagmentation; full length), STRT-seq-2i (tagmentation, 5' end) and SCRB-Seq (tagmentation, 3' end) (see Lafzi, Atefeh, et al., 2018. "Tutorial: Guidelines for the Experimental Design of Single-Cell RNA Sequencing Studies." Nature Protocols 13 (12): 2742-57). FIG. 2B. Exemplary flow diagram showing similar workflow to FIG. 2A, but for a biological sample such as a tissue sample or adherent cells on a slide, such as spatially arrayed (random or ordered) cells or nuclei. FIG. 2C. Exemplary flow diagram showing workflow for analysis of a biological sample (e.g., a cell or tissue sample having 2D or 3D spatial information to be analyzed, such as a tissue slice or spatially arrayed cells or nuclei) using solid-phase/bridge PCR or in situ PCR, rather than ePCR.

FIG. 4A-FIG. 4E. Exemplary cellular barcoding via nuclear DNA In Situ Hybridization (ISH) of cellular barcode probes (CBPs) and emulsion PCR (ePCR).

FIG. 4A. The nuclear gDNA of permeabilized cells or nuclei are labeled with CBP probes comprised of a Genome Binding Sequence (GBS), forward ($CBP_F$) and reverse ($CBP_R$) priming sites, and internal barcode sequences comprised of an optional spatial barcode (SpBC) sequence and a cellular barcode (CBC) sequence using modified ISH protocols. FIG. 4B. After annealing and optionally cross-linking the CBPs to their cognate gDNA sequence, analytes (e.g., proteins, etc.) within permeabilized CBP-tagged cells are covalently labeled with a recording tags (rTags) comprised of a CBP amplification primer F ($CBP_F$) and a universal PCR primer ($U_F$) sequence; in addition, the rTags attached to proteins, cDNA, or ATAC-Seq elements may also comprise additional barcode information (e.g., sample (SBC), spatial, fraction, etc.) and a unique molecular identifier (UMI) for more accurate counting during NGS analysis. FIG. 4C. Permeabilized cells labeled with nuclear CBPs and proteins labeled with rTag $CBP_F$ primers are emulsified together with a PCR mix comprising free $CBP_F$ and $CBP_R$ primers for amplification of the CBP barcodes. The $CBP_R$ primer is in excess over $CBP_F$ primer, enabling the CBP to be ported to the protein analytes tagged with rTag $CBP_F$ primer. FIG. 4D. A permeabilized cell whose proteins are labeled with the rTag $CBP_F$ primer. FIG. 4E. A permeabilized cell, shown after ePCR, whose proteins have had the entire CBP sequence transferred, via polymerase extension during ePCR, to the labeled proteins (the attached CBP polynucleotide forms an extended recording tag (extended rTag) to be used in further assays). For the downstream ProteoCode assay, the extended rTags are terminated with a $CBP_R$ sequence comprised of a 3' spacer (Sp) sequence for use in the ProteoCode assay for encoding via primer extension.

An exemplar restriction enzyme (RE) digestion can be a PmeI digestion, which cuts on average, every 65,000 bp (8-cutter). ExoIII chews dsDNA back at the 3' ends. CBP is annealed and ligated onto the target gDNA sequence corresponding to the GBS sequence.

Figure 5A:
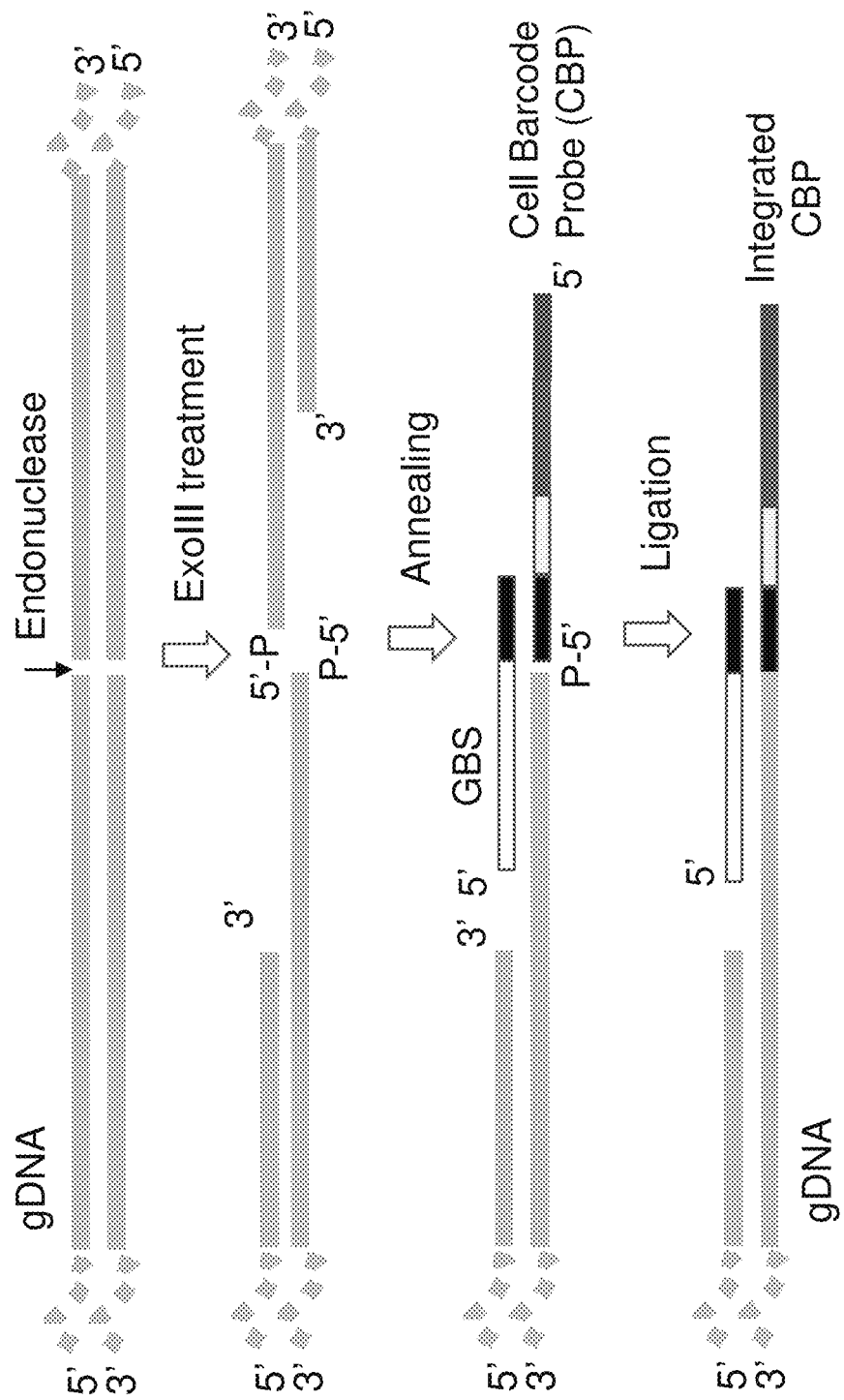
FIG. 5A. Exemplary enzymatic methods for ISH tagging of genomic DNA (gDNA) loci with cellular barcode probes (CBPs). Tagging gDNA with cellular barcodes using a combination of endonuclease digestion and ExoIII digestion to generate a localized linear ssDNA region, and In Situ Hybridization (ISH) with a CBP comprised of a Genome Binding Sequence (GBS) is shown. Fixed/permeabilized cells are incubated with an endonuclease system (RE, CRISPR-Cas, etc.) which generates either a nick or dsDNA break in the genomic DNA either at restriction enzyme (RE) site or at a gRNA targeted site (CRISPR-Cas). After endonuclease digestion, the fixed/permeabilized cells are exposed to Exonuclease III (ExoIII) which digests DNA from a 3' nick, blunt end or 3' recessed end. This digestion creates a long 5' single strand overhang which is the target for ISH annealing of the GBS portion of a Cellular Barcode Probe (CBP) or a splint adaptor for annealing to a CBP. After annealing, the CBP can be cross-linked or ligated to the 5' terminus of the gDNA effectively tagging the gDNA with a CBP.
Figure 5B:
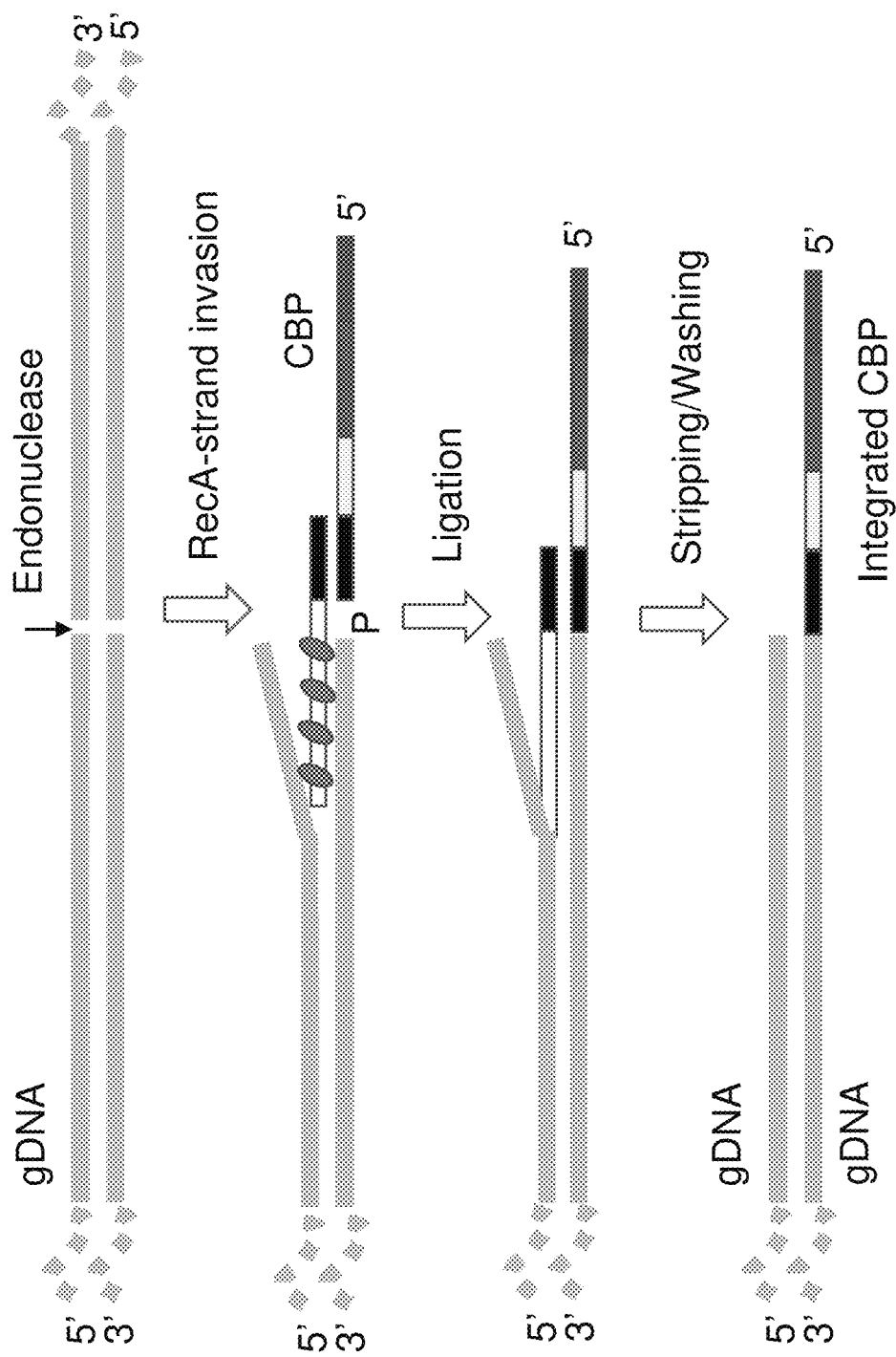

FIG. 5B. Exemplary RecA-coated strand invasion probe for ISH tagging of gDNA with CBPs.

Fixed/permeabilized cells are incubated with an endonuclease system (RE, CRISPR-Cas, etc.) which generates either a nick or dsDNA break in the genomic DNA either semi-randomly (RE) or site-specifically (CRISPR-Cas). After endonuclease digestion, the genomic DNA of fixed/permeabilized cells is annealed with RecA-coated CBP splint adapter enabling ligation of the CBP to the 5' terminus of the gDNA effectively tagging the gDNA with a CBP.

Figure 6:
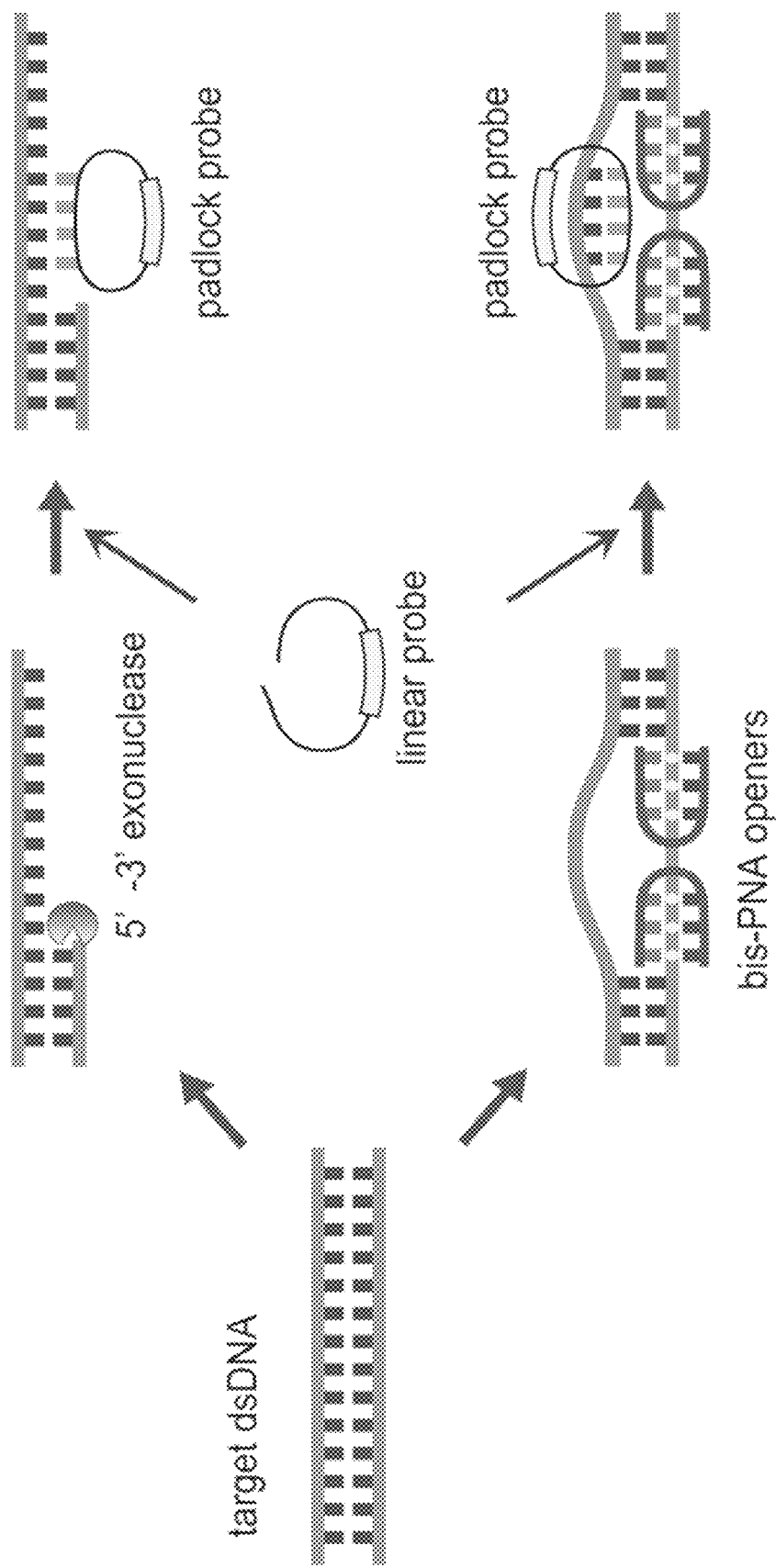

FIG. 6. Exemplary design and use of the padlock CBP in the disclosed barcoding methods (adopted from Matsunaga and Matsunaga, 2017, "FISH with Padlock Probes Can Efficiently Reveal the Genomic Position of Low or Single-Copy DNA Sequences." Cytologia 82 (4): 337-39; Yaroslavsky and Smolina, 2013).

Figure 7A:
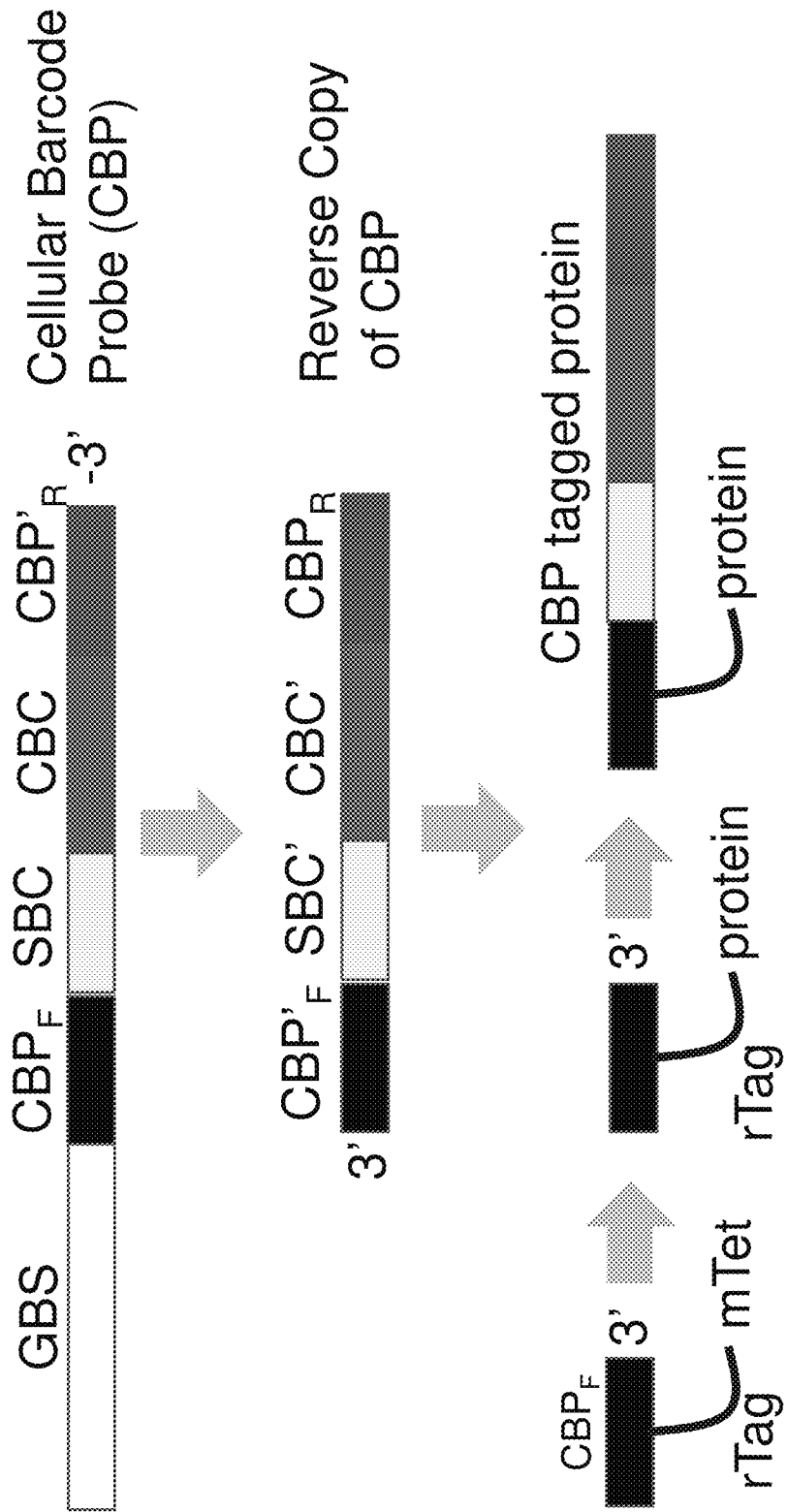
Figure 7B:
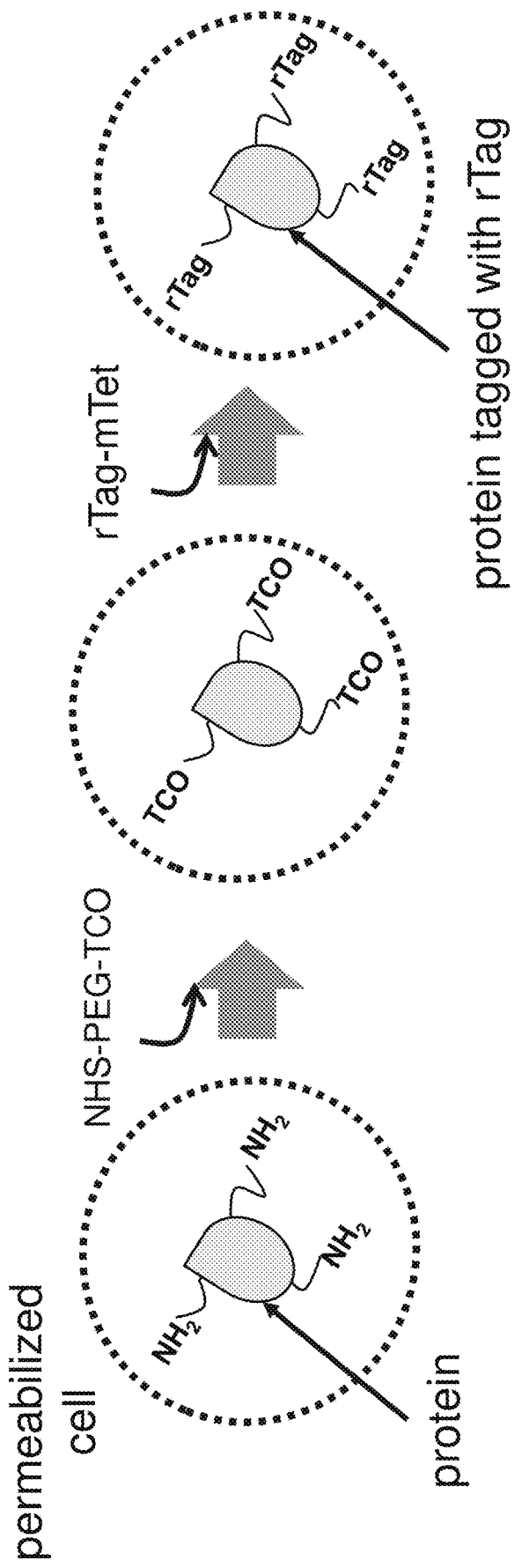
Figure 7C:
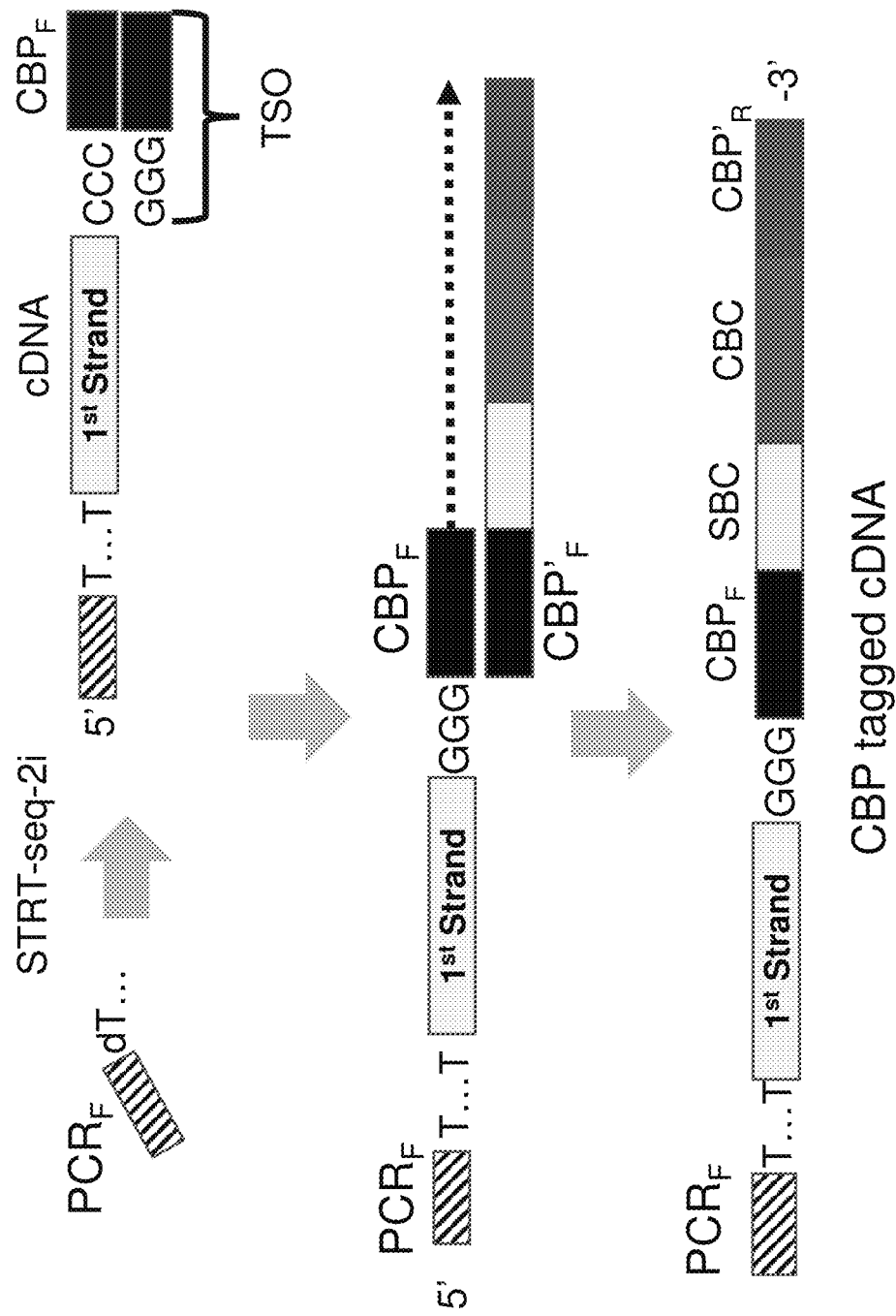

FIG. 7A-FIG. 7C. Exemplary designs of Cellular Barcode Probe (CBP) and transfers CBP to macromolecules within individual cell.

Figures 4D, 4E:
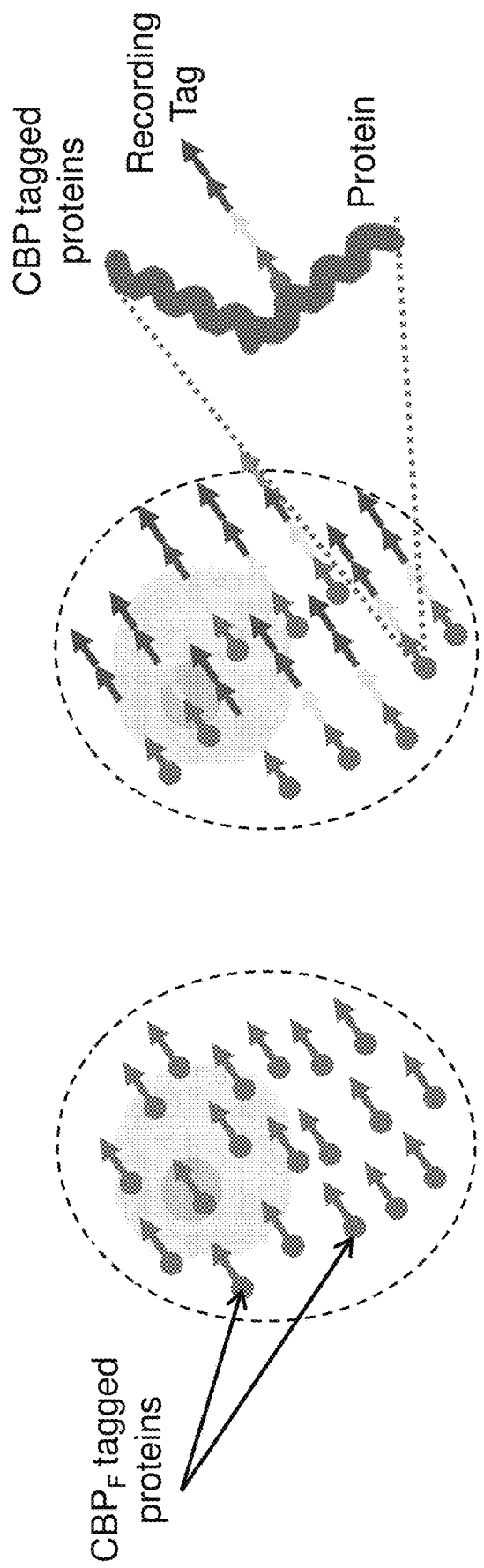

FIG. 7A. The CBP is comprised of several functional sequence elements. The Genome Binding Sequence (GBS), which anneals to a target locus (preferably, unique) on the gDNA of the cell, the CBP forward amplification primer ($CBP_F$), an optional Sample or Spatial Barcode (SBC or SpBC), the Cellular Barcode (CBC), and the CBP reverse primer ($CBP_R$). During amplification, both forward and reverse strands of the CBP (minus the GBS sequence) are generated. The reverse copies of the CBP amplicons diffuse throughout the cell and anneal to the rTag primer sequences attached to the macromolecules (e.g., proteins, cDNA, etc.) and the CBP information is copied to the rTags during the amplification reaction. The final result is CBP-tagged macromolecules with a cell-specific barcode. The rTag can comprise the $CBP_F$ on the 3' end and optionally comprise the SBC, UMI, $U_F$ (e.g., as shown in FIG. 4B) and other elements on the 5' of the $CBP_F$. The $CBP_F$ in the rTag can hybridize to the $CBP'_F$ (complement of the CBP) and port the CBC and optionally SBC information into the rTag.

FIG. 7B. Proteins within a permeabilized cell are labeled with DNA recording tag stubs (rTags) using a two-step reaction, in which the first step uses a heterobifunctional linker for activation of lysines on the proteins converting the amines to a click chemistry moiety (e.g., TCO), which in a subsequent step is coupled to an rTag bearing an mTet moiety, which reacts via iEDDA bioconjugation chemistry to the TCO-derivitized proteins.

FIG. 7C. CBP tagging of cDNA within the cell using a modified STRT-seq-2i protocol for 5' RNA-seq tag counting. During reverse transcription of mRNA into cDNA, an oligo dT primer comprised of a universal PCR sequence ($PCR_F$) anneals to the polyA sequence on the mRNA and generates a $1^{st}$ cDNA strand incorporating the $CBP'_F$ sequence. Using a SMART cDNA protocol employing template switching reverse transcription and template switch oligo primer (TSO) containing a universal priming site ($U_{TSO}$) and 3' GGG nucleotides (or ribonucleotides, or LNA), enables completion of the $1^{st}$ strand with a flanking 3' $CBP'_F$ sequence and a TSO sequence. During CBP amplification, the $2^{nd}$ strand primes on the CBP copy strand and effectively transfer CBP information to the $2^{nd}$ strand DNA sequence. An NGS library is created from this product by amplifying with the PCR primers, $PCR_F$ and $CBP_R$. A short read NGS library is created from this PCR product by a tagmentation reaction coupled with a second and PCR amplification reaction using the tagmentation primer and $CBP_R$ to enable 5' RNA-Seq tag counting.

Figure 7D:
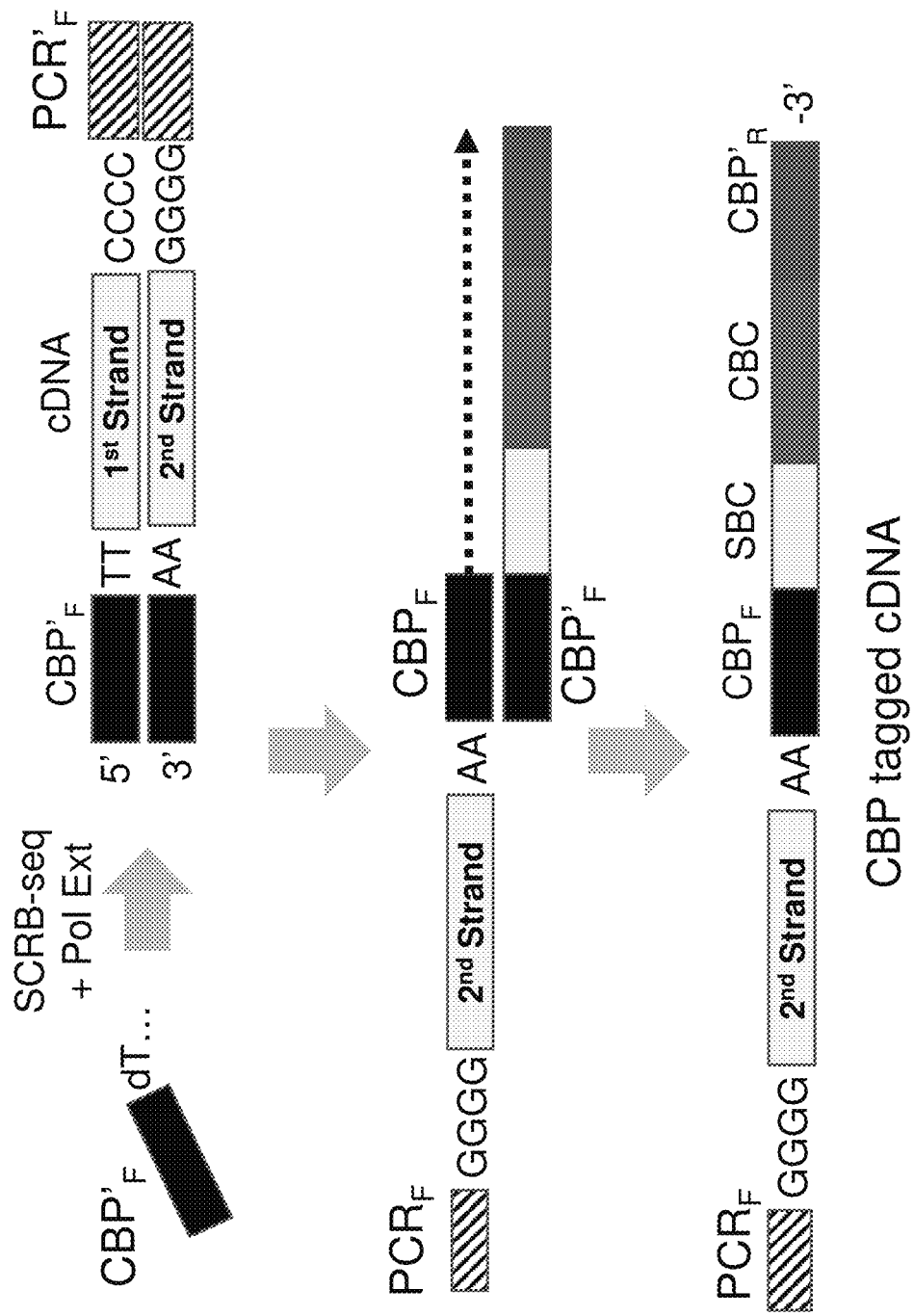

FIG. 7D. CBP tagging of cDNA within the cell using a modified SCRB-seq protocol for 3' RNA-Seq tag counting (Soumillon, et al., 2014. "Characterization of Directed Differentiation by High-Throughput Single-Cell RNA-Seq." bioRxiv). SCRB-Seq relies on a template-switching reverse transcriptase to convert poly(A)+mRNA from isolated single cells to cDNA decorated with universal adapters, single cell barcodes and unique molecular identifiers (UMIs). During reverse transcription of mRNA into cDNA, an oligo dT primer containing a 5' $CBP'_F$ anneals to the polyA sequence on the mRNA and generates a $1^{st}$ cDNA strand incorporating the $CBP'_F$ sequence. Using a SMART-Seq or SCRB-Seq cDNA protocol employing template switching reverse transcription and template switch oligo (TSO) containing a universal priming site and a 3' G nucleotides (or ribonucleotides, LNA), enables completion of the $1^{st}$ strand with a flanking 3' $CBP'_F$ sequence and a PCR amplification sequence. During CBP amplification, the $2^{nd}$ strand primes on the CBP copy strand and effectively transfers CBP information to the $2^{nd}$ strand DNA sequence. An NGS library is created from this product by amplifying with the TSO $PCR_F$ primer and the $CBP_R$ primer. A short read NGS library is created from this PCR product by a tagmentation reaction coupled with a second and PCR amplification reaction using the tagmentation primer and $CBP_R$ to enable 3' RNA-Seq tag counting.

Figure 8A:
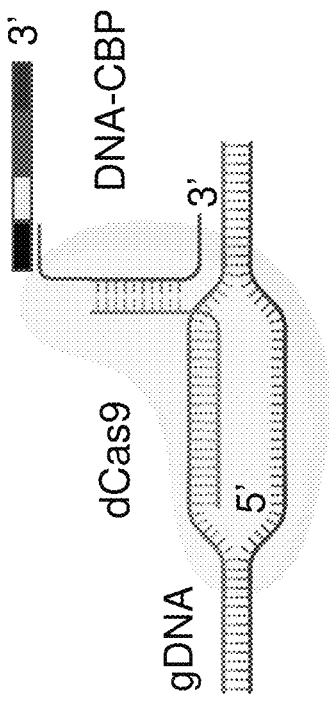
Figure 8B:
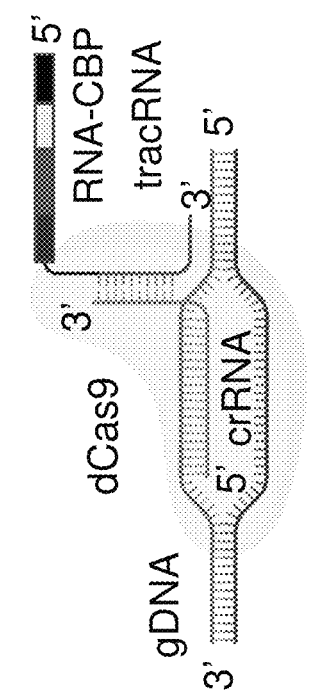
Figure 8C:
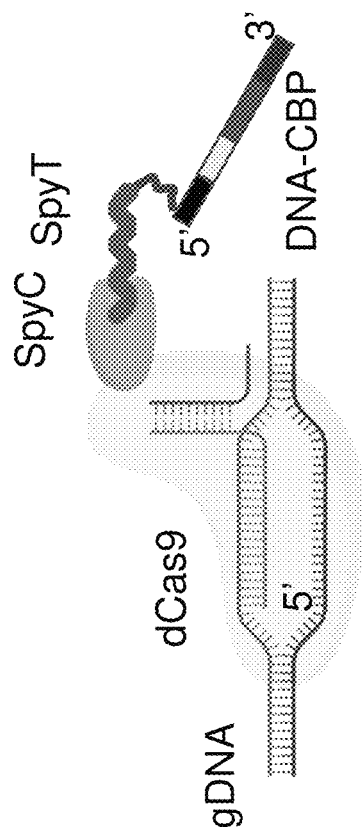

FIG. 8A-FIG. 8C. Exemplary designs of specific genomic DNA-binding carriers (CRISPR-dCas9) for locus-specific targeting of Cellular Barcode Probes (CBPs).

FIG. 8A. The CBP probe (RNA) is contiguous with a portion of the gRNA/tracRNA of the ribonucleotide dCas9 complex, or, in FIG. 8B, the CB probe (DNA) is annealed to a complementary region of the gRNA/tracRNA. In the case of an RNA CBP probe, reverse transcription is used to write it into a DNA sequence. FIG. 8C. Alternatively, the CBP can be covalently attached to the dCas9 via a fusion construct; in the example shown, the dCas9 is fused to a SpyCatcher (SpyC) protein which covalently binds a Spy-Tag (SpyT) peptide coupled to a DNA CBP sequence.

FIG. 9A-FIG. 9C. Exemplary prime editing in permeabilized cells to attach cellular barcode probes.

FIG. 9A. A nicking Cas9 (non-target strand cleavage) is loaded with a prime editing guide RNA (pegRNA) which is comprised of a 3' portion encompassing the cellular barcode probe and a complementary region to the targeted DNA (genome-binding region). FIG. 9B. Nicking of the non-target strand with nCas9 creates a 3' ssDNA terminus that extends on the pegRNA terminus through action of a Reverse Transcriptase (RT). FIG. 9C. This step effectively writes the CBP into the gDNA for downstream single cell barcoding applications.

Figure 10:
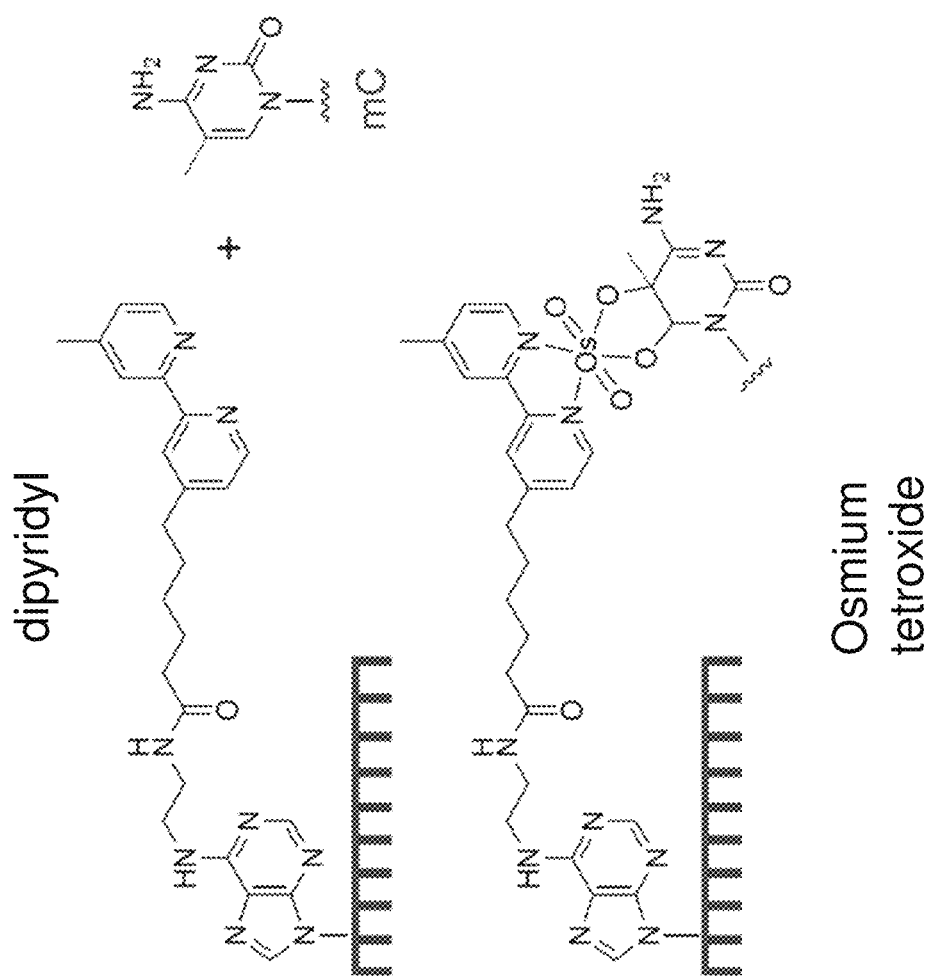

FIG. 10. Exemplary site-specific cellular barcode tagging of imprinted loci. An adenine base labeled with a bipyridyl moiety chelates osmium tetroxide and covalently attaches to opposing methyl cytosine bases. Adapted from Buchmuller, et al., 2021. "Programmable Tools for Targeted Analysis of Epigenetic DNA Modifications." Current Opinion in Chemical Biology 63 (August): 1-10.

Figure 11A:
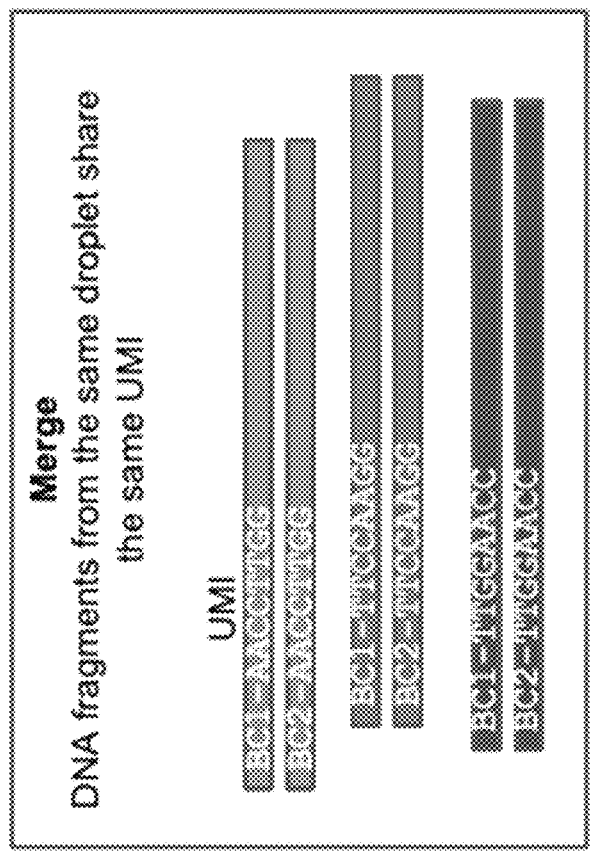
Figure 11A:
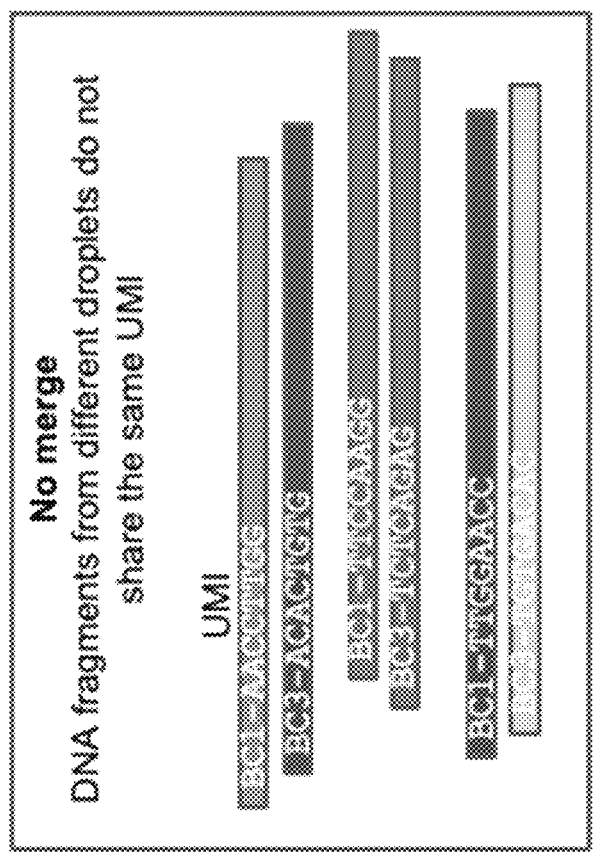

FIG. 11A-FIG. 11B. Exemplary in silico merging macromolecules from the same droplet barcoded by two or more barcode sequences. FIG. 11A. Unique Molecular Identifier (UMI) sequences incorporated in the macromolecules, such as cell DNA fragments, are used. The cell barcodes from the same droplet will share UMI sequences at a rate exceeding what may be expected by chance. For each pair of cell barcodes, the Jaccard index is computed over the UMI sequences, providing a measure of how similar the UMI sequences are for any pair of cell barcodes. FIG. 11B. From these pairwise Jaccard index statistics, a knee plot is generated to determine pairs that are likely to have originated from the same droplet, and a Jaccard index cutoff value is used to determine barcode pairs that need to be merged (adopted from Lareau, C.A., et al. (2019) Droplet-based combinatorial indexing for massive-scale single cell chromatin accessibility. Nat Biotechnol, 37, 916-924).

Figure 12:
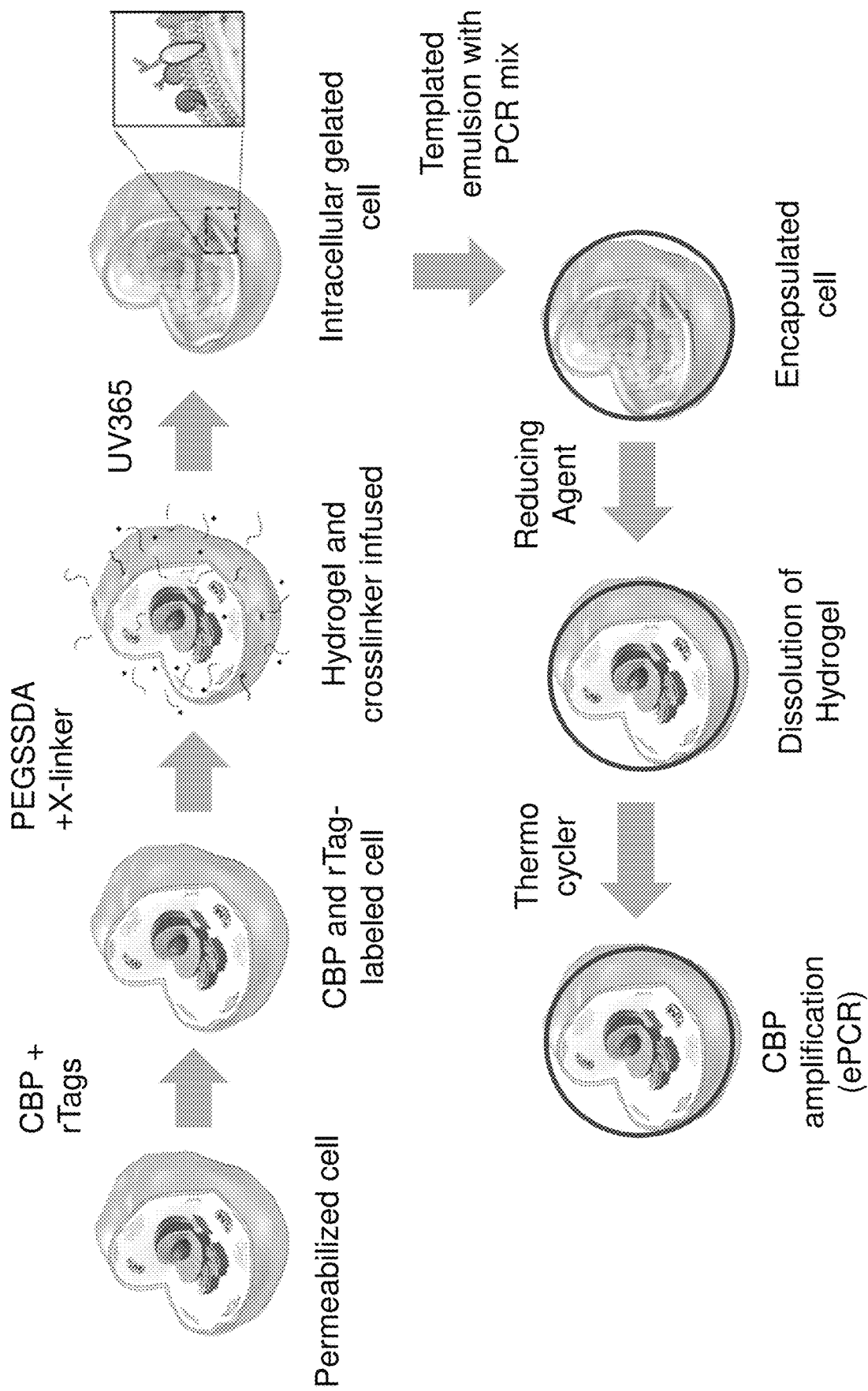

FIG. 12. Exemplary method of hydrogelation of fixed/permeabilized cells for templated emulsions. Fixed/permeabilized cells are labeled with CBP and rTags as described in Example 2. Then, the cells are infused with a cleavable polymer mix (PEGSSDA), a photo-activated crosslinking agent, and primers and PCR mix. Exposure to UV 365 nm light source of appropriate intensity cross-links the polymer forming hydrogel within the interior of the cell. The hydrogelated cell is durable and serves as a particle in templated emulsion formation. Then, the hydrogel is dissolved by exposing the encapsulated cell to a reducing agent such as dithiothreitol (DTT) in saturated fluoropolymer oil. Finally, the cell is ready for emulsion PCR (ePCR). Adopted from Li, Siran, et al., 2020. "Copolymerization of Single-Cell Nucleic Acids into Balls of Acrylamide Gel." Genome Research 30 (1): 49-61.

Figure 13:
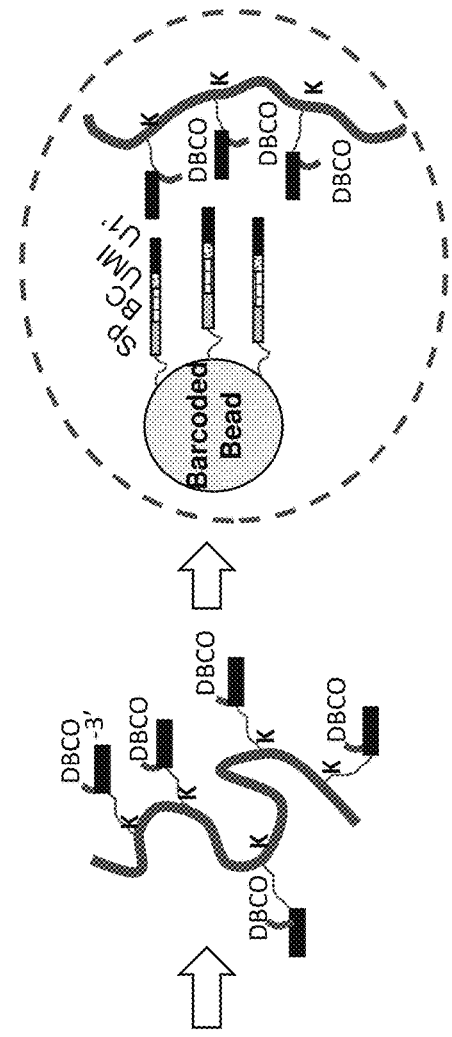
Figure 13:
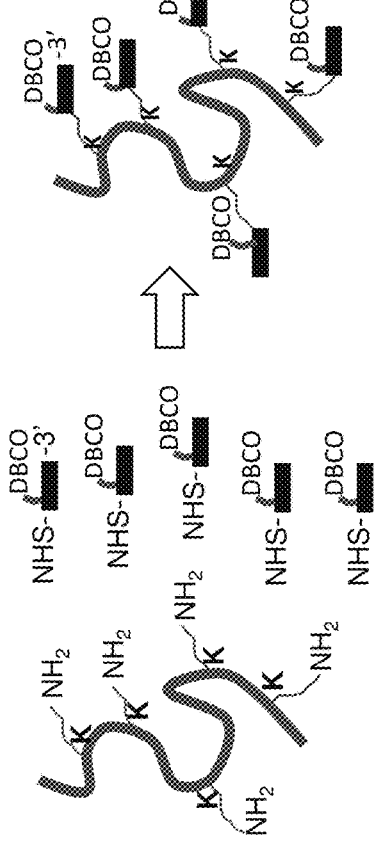
Figure 13:
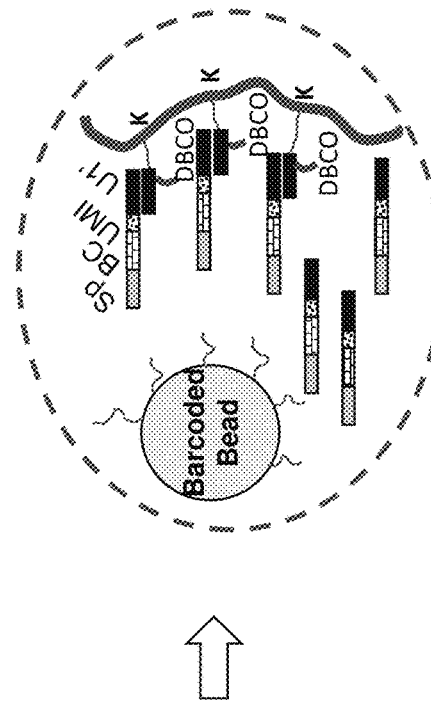

FIG. 13 illustrates exemplary generation of compartment barcoded nucleic acid recording tags attached to peptides. Compartment barcoding technology (e.g., barcoded beads in microfluidic droplets, etc.) can be used to transfer a compartment-specific barcode to molecular contents encapsulated within a particular compartment. In a particular embodiment, the protein molecule is denatured, and the F-amine group of lysine residues (K) is chemically conjugated to an activated universal DNA tag molecule (comprising a universal priming sequence (U1)), shown with NHS moiety at the 5' end). After conjugation of universal DNA tags to the polypeptide, excess universal DNA tags are removed. Then, the universal DNA tagged polypeptides are hybridized to nucleic acid molecules bound to beads, wherein the nucleic acid molecules bound to an individual bead comprise a unique population of compartment tag (barcode) sequences. The compartmentalization can occur by separating the sample into different physical compartments, such as droplets (illustrated by the dashed oval). Alternatively, compartmentalization can be directly accomplished by the immobilization of the labeled polypeptides on the bead surface, e.g., via annealing of the universal DNA tags on the polypeptide to the compartment DNA tags on the bead, without the need for additional physical separation. A single polypeptide molecule interacts with only a single bead (e.g., a single polypeptide does not span multiple beads). Multiple polypeptides, however, may interact with the same bead. In addition to the compartment barcode sequence (BC), the nucleic acid molecules bound to the bead may be comprised of a common Sp (spacer) sequence, a unique molecular identifier (UMI), and a sequence complementary to the polypeptide DNA tag, U1'. After annealing of the universal DNA tagged polypeptides to the compartment tags bound to the bead, the compartment tags are released from the beads via cleavage of the attachment linkers.

Figure 14:
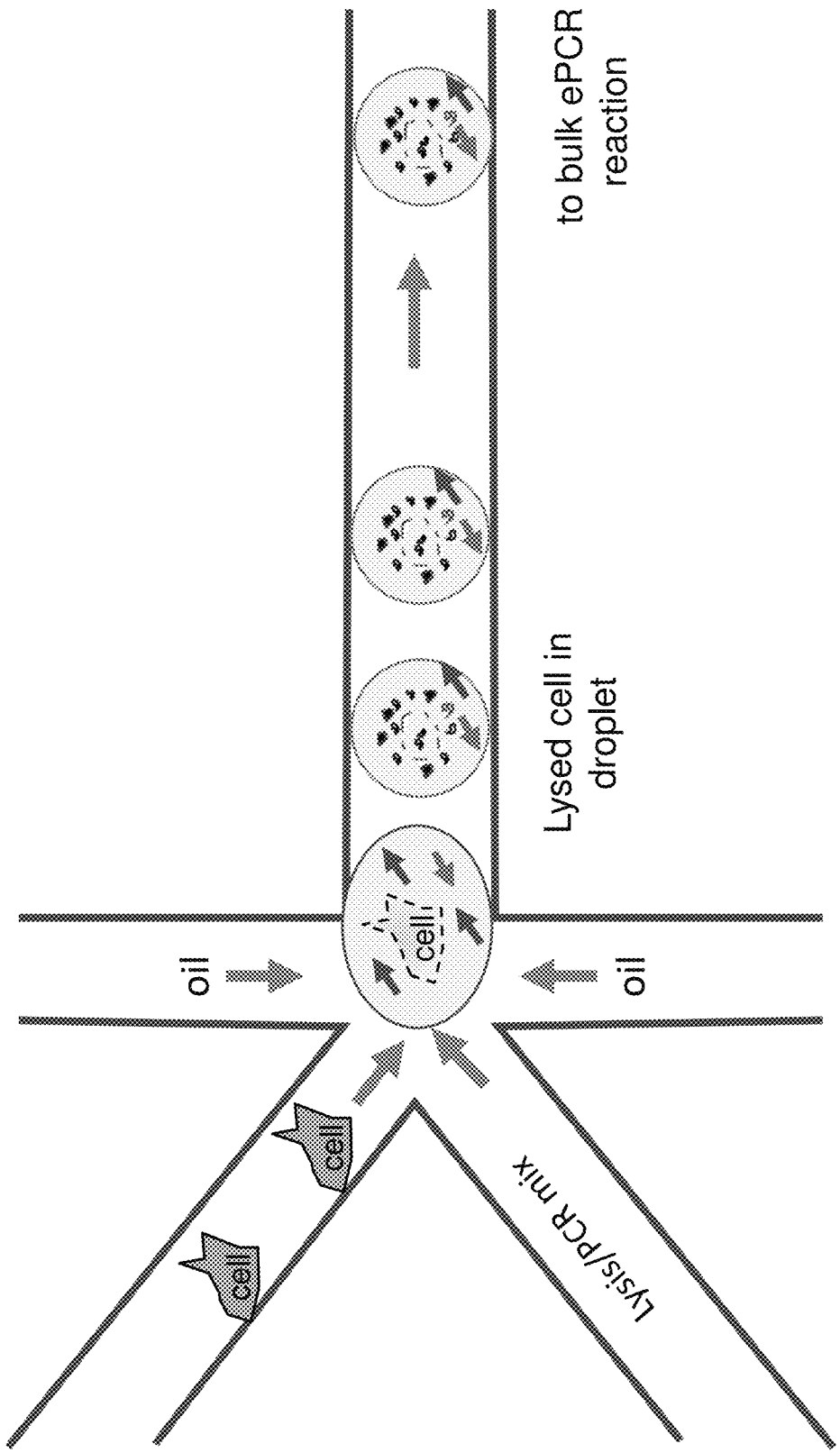

FIG. 14. Exemplary compartmentalization of cells in droplets. Individual cells or nuclei having CBPs are partitioning into a plurality of compartments by droplet formation through a T-junction microfluidic or flow focusing device. In the Y or T-junction shown, one aqueous flow stream contains the cell lysis detergent (e.g., LiDS lysis buffer: 100 mM Tris pH 7.5, 500 mM LiCl, 10 mM EDTA, 1% lithium dodecyl sulfate, 5 mM DTT) and PCR mix and the other aqueous flow stream contains the suspended cells in an isotonic buffer (e.g., PBS). The detergent can be an ionic (e.g., SDS, LDS, etc.), non-ionic (e.g., TX-100, Tween-20, etc.), or zwitterionic (e.g., CHAPS, CHAPSO). Moreover, during emulsification and droplet formation, the droplet interior, such as pH, presence of a reducing agent, activatable detergent, etc., can be modified by addition of a reagent to the fluoro-oil of the emulsion.

Figure 15:
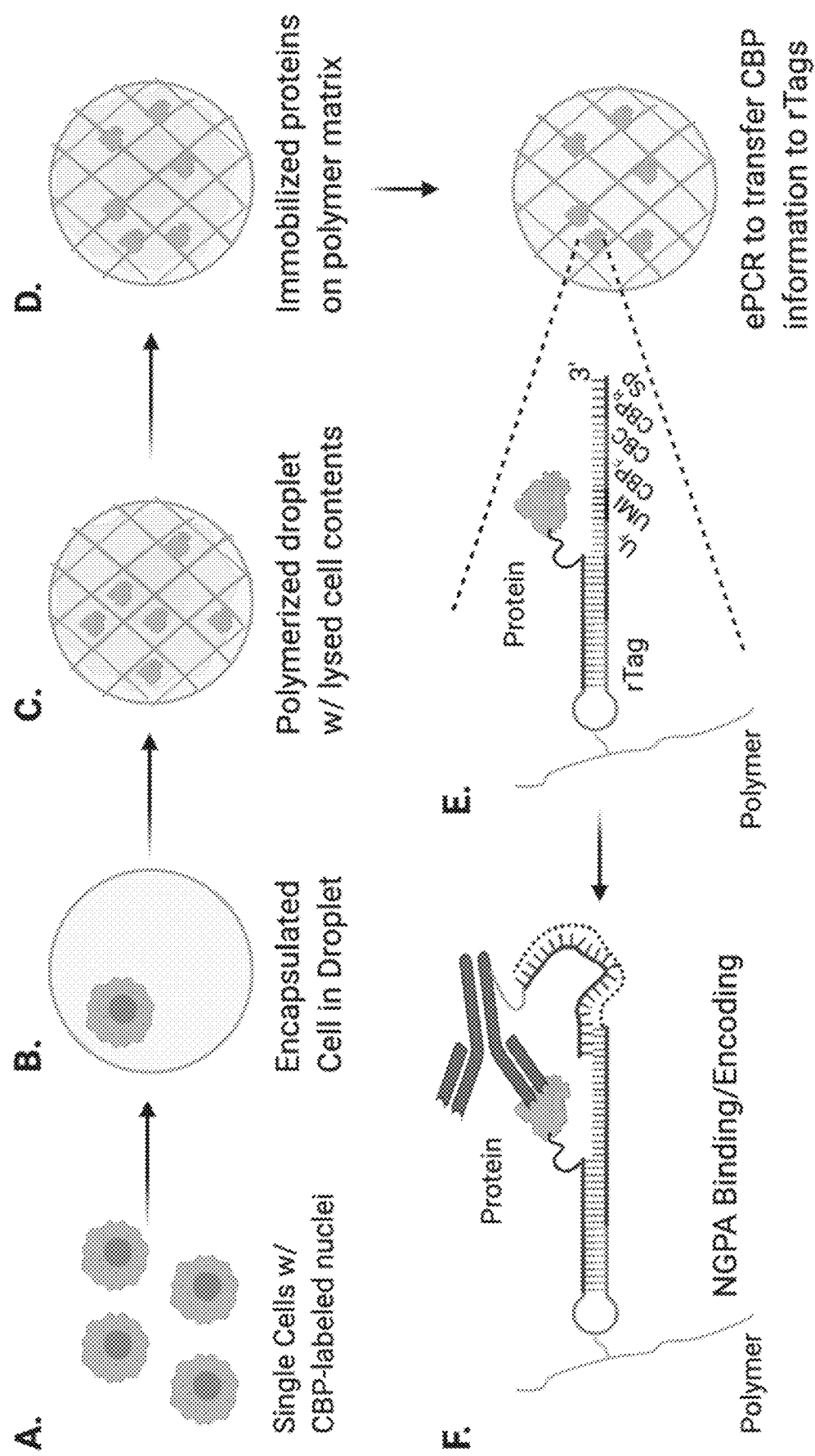

FIG. 15. Exemplary compartmentalization of individual cells in droplets, followed by cell barcode amplification, transfer barcode information to rTags of protein analytes and NGPA assay for the tagged protein analytes. (A) Single cells are fixed, permeabilized, and have their nuclei labeled with CBPs. (B) Single cells are encapsulated in droplets along with a polymerizable matrix and lysis buffer. (C) Polymer matrix polymerizes and immobilizes DNA rTags within matrix. (D) Proteins released from the cell conjugate to activated DNA rTags within polymer matrix. (E) Single cell polymer beads (SCPB) are extracted into aqueous phase and combinatorial barcodes can be added to SCPBs via a SCI-Seq split-pool process. (F) The resultant SCPBs can be used directly in a ProteoCode NGPA immunoassay (exemplary antibody readout shown) or processed for an NGPS assay for quantitative assessment of proteins from single cell.

Approaches for compartmental-based partitioning include droplet formation through microfluidic devices using T-junctions and flow focusing, emulsion generation using agitation or extrusion through a membrane with small holes (e.g., track etch membrane), and others.

Figure 16A:
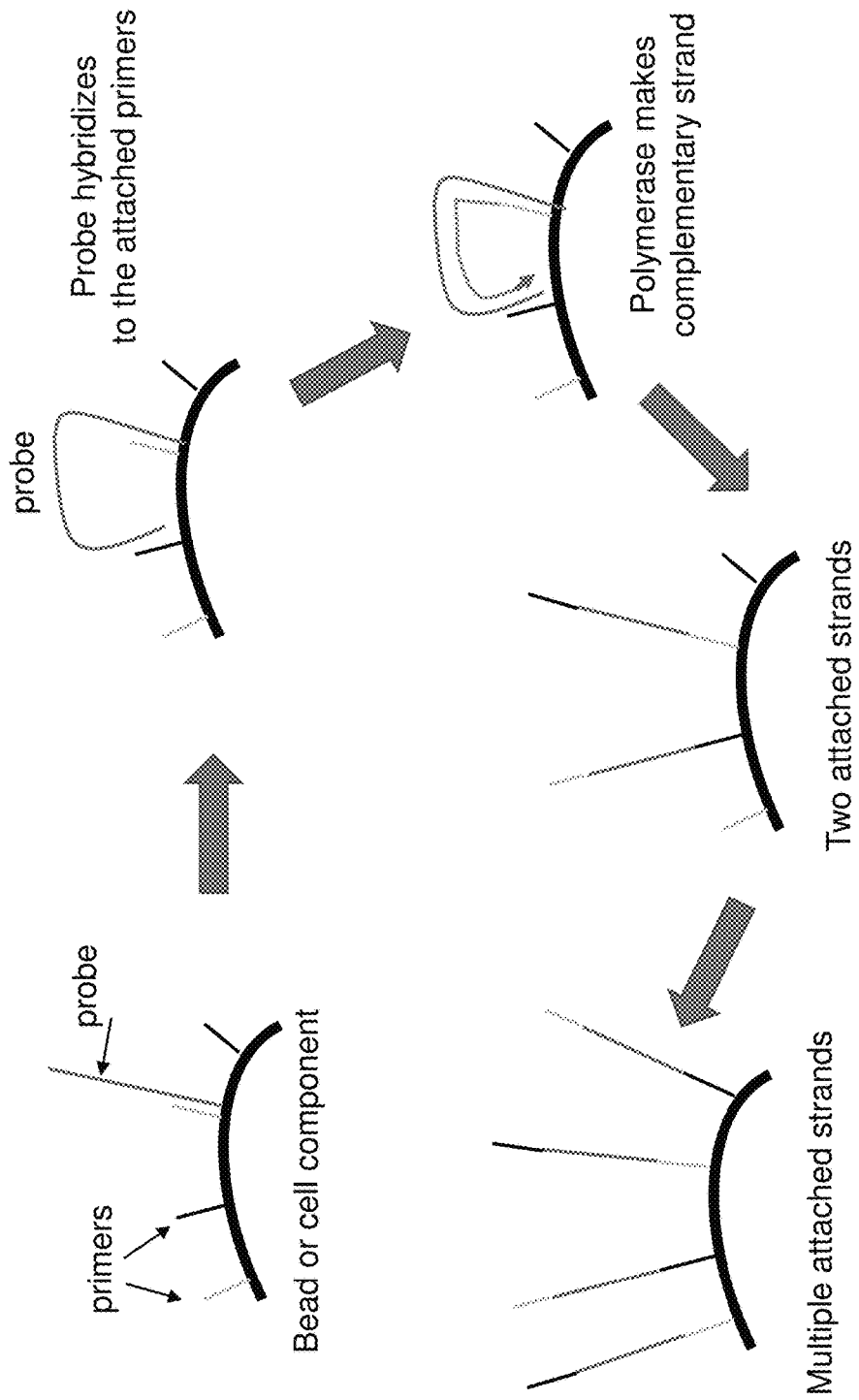
Figure 16B:
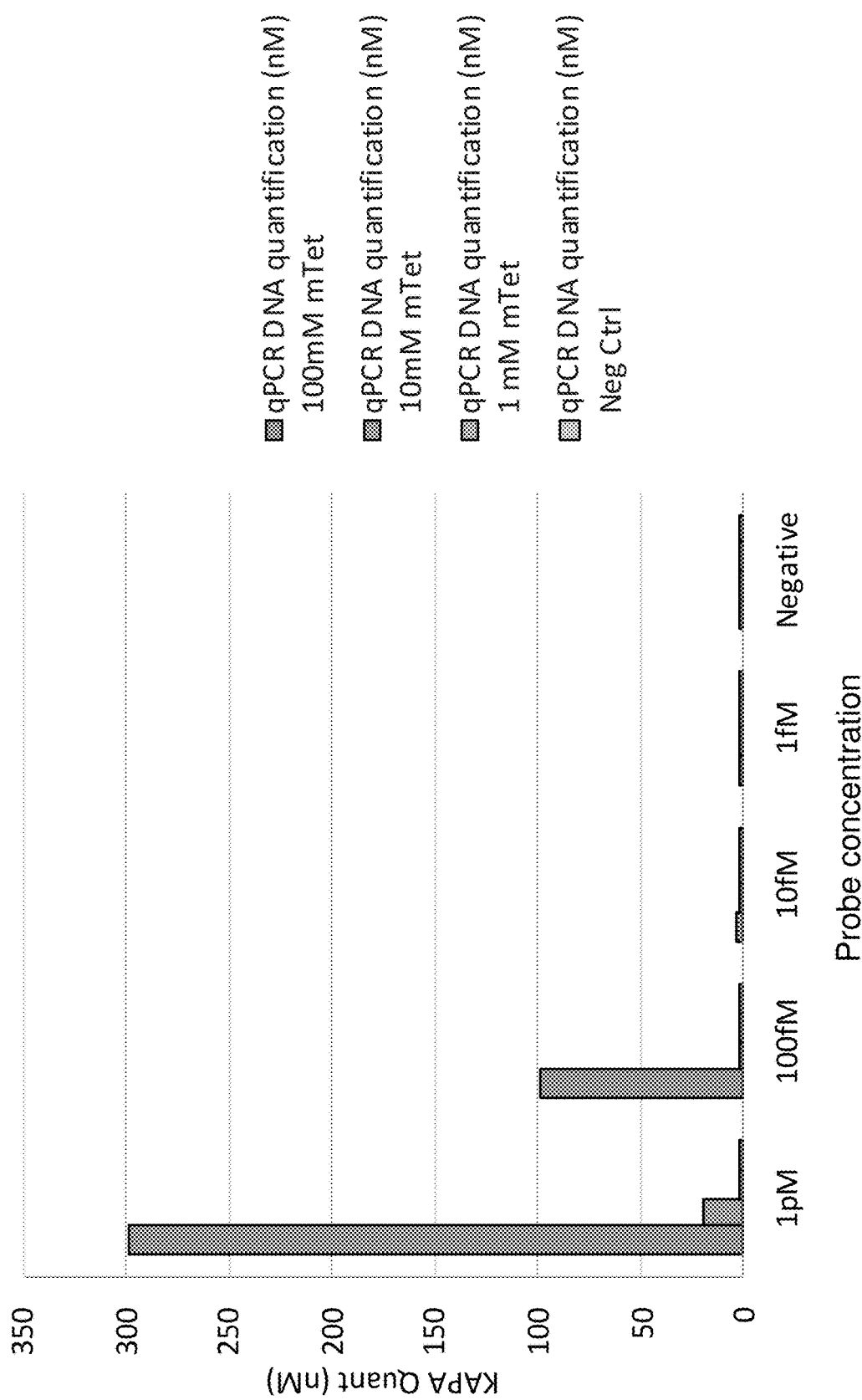

FIG. 16A-FIG. 16B. Exemplary "bridge" amplification of a cell barcode probe using a pair of primers attached to porous sepharose beads. FIG. 16A. Design of "bridge" amplification. FIG. 16B. Exemplary results of on-bead "bridge" amplification show amplified product quantification using variable P5/P7 primer density.

DETAILED DESCRIPTION

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

Definitions

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference. Unless the context requires otherwise, throughout the specification and claims which follow, the word "comprise" and variations thereof, such as, "comprises" and "comprising," are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the singular forms "a," "an" and "the" include plural referents unless the context clearly dictates otherwise. Thus, for example, reference to "a peptide" includes one or more peptides, or mixtures of peptides. Also, and unless specifically stated or obvious from context, as used herein, the term "or" is understood to be inclusive and covers both "or" and "and".

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

As used herein, the term "sample" refers to anything which may contain an analyte for which an analyte assay is desired. As used herein, a "sample" can be a solution, a suspension, liquid, powder, a paste, aqueous, non-aqueous or any combination thereof. In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. A biological sample may also be comprised of a tissue biopsy such as tissue section, a slide-mounted tissue section, an enriched fraction of cells of interest, etc.

The terms "level" or "levels" are used to refer to the presence and/or amount of a target, e.g., a substance or an organism that is part of the etiology of a disease or disorder, and can be determined qualitatively or quantitatively. A "qualitative" change in the target level refers to the appearance or disappearance of a target that is not detectable or is present in samples obtained from normal controls. A "quantitative" change in the levels of one or more targets refers to a measurable increase or decrease in the target levels when compared to a healthy control.

As used herein, the term "macromolecule" encompasses large molecules composed of smaller subunits. Examples of macromolecules include, but are not limited to peptides, polypeptides, proteins, nucleic acids, carbohydrates, lipids, macrocycles, or a combination or complex thereof. A macromolecule also includes a chimeric macromolecule composed of a combination of two or more types of macromolecules, covalently linked together (e.g., a peptide linked to a nucleic acid). A macromolecule may also include a "macromolecule assembly", which is composed of non-covalent complexes of two or more macromolecules. A macromolecule assembly may be composed of the same type of macromolecule (e.g., protein-protein) or of two or more different types of macromolecules (e.g., protein-DNA).

As used herein, the term "polypeptide" is used interchangeably with the term "peptide" refers to a molecule comprising a chain of two or more amino acid residues joined by peptide bonds. In some embodiments, a polypeptide comprises 2 to 50 amino acids. In some embodiments, a polypeptide does not comprise a secondary, tertiary, or higher structure. In some embodiments, the polypeptide is a protein. In some embodiments, a polypeptide comprises more than 50 amino acid residues. In some embodiments, in addition to a primary structure, a polypeptide comprises a secondary, tertiary, or higher structure. The amino acids of the polypeptides are most typically L-amino acids, but may also be D-amino acids, modified amino acids, amino acid analogs, amino acid mimetics, or any combination thereof. Polypeptides can be naturally occurring, synthetically produced, recombinantly expressed, isolated, or be produced by a combination of the described methodologies. Polypeptides may also comprise additional groups modifying the amino acid chain, for example, functional groups added via post-translational modification. The polypeptide macromolecule may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term "amino acid" refers to an organic compound comprising an amine group, a carboxylic acid group, and a side-chain specific to each amino acid, which serve as a monomeric subunit of a peptide. An amino acid includes the 20 standard, naturally occurring or canonical amino acids as well as non-standard amino acids. The standard, naturally-occurring (or natural) amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, R-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids. The term "amino acid residue" refers to an amino acid incorporated into a polypeptide that forms peptide bond(s) with neighboring amino acid(s).

As used herein, the term "post-translational modification" refers to modifications that occur on a peptide after its translation, e.g., translation by ribosomes, is complete. A post-translational modification may be a covalent chemical modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini. The term post-translational modification can also include peptide modifications that include one or more detectable labels.

The term "detectable label" as used herein refers to a substance which can indicate the presence of another substance when associated with it. The detectable label can be a substance that is linked to or incorporated into the substance to be detected. In some embodiments, a detectable label is suitable for allowing for detection and also quantification, for example, a detectable label that emitting a detectable and measurable signal. Examples of detectable labels include a dye, a fluorophore, a chromophore, a fluorescent nanoparticle (e.g. quantum dot), a radiolabel, an enzyme (e.g. alkaline phosphatase, luciferase or horseradish peroxidase), or a chemiluminescent or bioluminescent molecule.

As used herein, the term "linker" refers to one or more of a nucleotide, a nucleotide analog, an amino acid, a peptide, a polypeptide, a polymer, or a non-nucleotide chemical moiety that is used to join two molecules. A linker may be used to join a recording tag with a polypeptide, a polypeptide with a solid support, a recording tag with a solid support, etc. In certain embodiments, a linker joins two molecules via enzymatic reaction or chemistry reaction (e.g., a click chemistry reaction).

The term "ligand" as used herein refers to any molecule or moiety connected to the compounds described herein. "Ligand" may refer to one or more ligands attached to a compound. In some embodiments, the ligand is a pendant group or binding site (e.g., the site to which the binding agent binds).

As used herein, the term "barcode" refers to a nucleic acid molecule of about 3 to about 30 bases (e.g., 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a polypeptide, a binding agent, a set of binding agents from a binding cycle, a sample polypeptides, a set of samples, polypeptides within a compartment (e.g., droplet, bead, or separated location), polypeptides within a set of compartments, a fraction of polypeptides, a set of polypeptide fractions, a spatial region or set of spatial regions, a library of polypeptides, or a library of binding agents. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error-correcting or error-tolerant barcodes. Barcodes can be used to computationally deconvolute the multiplexed sequencing data and identify sequence reads derived from an individual polypeptide, sample, library, etc. A barcode can also be used for deconvolution of a collection of polypeptides that have been distributed into small compartments for enhanced mapping.

A "sample barcode", also referred to as "sample tag" identifies from which sample a macromolecule derives.

A "spatial barcode" which region of a 2-D or 3-D tissue section from which a macromolecule derives. Spatial barcodes may be used for molecular pathology on tissue sections. A spatial barcode allows for multiplex sequencing of a plurality of samples or libraries from tissue section(s).

As used herein, the term "solid support", or "substrate" refers to any solid material, including porous and non-porous materials, to which a macromolecule can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, a PTFE membrane, a silicon wafer chip, a flow through chip, a flow cell, a biochip including signal transducing electronics, a channel, a microtiter well, an ELISA plate, a spinning interferometry disc, a nitrocellulose-based polymer surface, a polymer matrix, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. For example, when solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a porous bead, a paramagnetic bead, a glass bead, a controlled pore bead, a silica-based bead, or any combinations thereof. A bead may be spherical or an irregularly shaped. In certain embodiments, beads range in size from about 0.2 micron to about 200 microns, or from about 0.5 micron to about 5 micron. In some embodiments, beads can be about 1, 1.5, 2, 3, 4, 5, 6, 7, 8, 9, 10, 15, or 20 µm in diameter. In certain embodiments, "a bead" solid support may refer to an individual bead or a plurality of beads. In some embodiments, the solid support is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, or between about 200 nm and about 500 nm in diameter.

As used herein, the term "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding. In some embodiments, the nucleic acid molecule or oligonucleotide is a modified oligonucleotide. In some embodiments, the nucleic acid molecule or oligonucleotide is a DNA with pseudo-complementary bases, a DNA with protected bases, an RNA molecule, a BNA molecule, an XNA molecule, a LNA molecule, a PNA molecule, or a morpholino DNA, or a combination thereof. In some embodiments, the nucleic acid molecule or oligonucleotide is backbone modified, sugar modified, or nucleobase modified. In some embodiments, the nucleic acid molecule or oligonucleotide has nucleobase protecting groups such as Alloc, electrophilic protecting groups such as thiranes, acetyl protecting groups, nitrobenzyl protecting groups, sulfonate protecting groups, or traditional base-labile protecting groups.

As used herein, "nucleic acid sequencing" means the determination of the order of nucleotides in a nucleic acid molecule or a sample of nucleic acid molecules. Similarly, "polypeptide sequencing" means the determination of the identity and order of at least a portion of amino acids in the polypeptide molecule or in a sample of polypeptide molecules.

As used herein, "analyzing" the macromolecule refers to identify, detect, quantify, characterize, distinguish, or a combination thereof, all or a portion of the components of the macromolecule. For example, analyzing a polypeptide includes determining all or a portion of the amino acid sequence (contiguous or non-continuous) of the polypeptide. Analyzing a polypeptide also includes partial identification of a component of the polypeptide.

As used herein "amplification" refers to any in vitro method for increasing the number of copies of a nucleotide sequence with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules.

The terms "hybridization" and "hybridizing" refers to the pairing of two complementary single-stranded nucleic acid molecules (RNA and/or DNA) to form a double-stranded molecule (nucleic acid duplex). As used herein, two nucleic acid molecules may be hybridized, although the base pairing is not completely complementary. Accordingly, mismatched bases do not prevent hybridization of two nucleic acid molecules provided that appropriate conditions, well known in the art, are used. In the present invention, the term "hybridization" refers particularly to hybridization of an oligonucleotide to a template molecule.

As used herein, the term "primer extension", also referred to as "polymerase extension", refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "recording tag" and term "coding tag" refer to a nucleic acid molecule or sequenceable polymer molecule (see, e.g., Niu et al., 2013, Nat. Chem. 5:282-292) that optionally comprises identifying information for a macromolecule to which it is associated. A recoding tag or coding tag may be directly linked to a macromolecule, linked to a macromolecule via a multifunctional linker, or associated with a macromolecule by virtue of its proximity (or co-localization) on a solid support. A recording tag or coding tag may further comprise other functional components, e.g., a universal priming site, unique molecular identifier, a barcode (e.g., a sample barcode, a fraction barcode, spatial barcode, a compartment tag, etc.), a spacer sequence that is complementary to a spacer sequence of a coding tag, or any combination thereof.

As used herein, the term "binding agent" refers to a nucleic acid molecule, a polypeptide, a carbohydrate, or a small molecule that binds to, associates, unites with, recognizes, or combines with a binding target, e.g., a macromolecule analyte or a component or feature of a macromolecule analyte. In some embodiments, a binding agent comprises a polypeptide. In some embodiments, a binding agent comprises an aptamer. In some embodiments, a binding agent does not comprise a polynucleotide. In some embodiments, a binding agent form a covalent association with the macromolecule analyte or component or feature of a macromolecule analyte. In other embodiments, a binding agent form a non-covalent association with the macromolecule analyte or component or feature of a macromolecule analyte. A binding agent may also be a chimeric binding agent, composed of two or more types of molecules. A binding agent may preferably bind to a chemically functionalized or modified amino acid (e.g., an amino acid that has been functionalized or modified by a functionalizing reagent) over a non-modified amino acid. For example, a binding agent may preferably bind to an amino acid that has been functionalized or modified over an amino acid that is unmodified. A binding agent may exhibit selective binding to a component or feature of a polypeptide (e.g., a binding agent may selectively bind to one of the 20 possible natural amino acid residues and bind with very low affinity or not at all to the other 19 natural amino acid residues). A binding agent may exhibit less selective binding, where the binding agent is capable of binding or configured to bind to a plurality of components or features of a polypeptide (e.g., a binding agent may bind with similar affinity to two or more different amino acid residues).

The terms "specific binding" generally refers to an engineered binding agent that binds to a particular functionalized amino acid residue more readily than it would bind to a random functionalized amino acid residue (e.g., there is a detectable relative increase in the binding of the binding agent to a specific or group of functionalized amino acid residues). The term "specificity" is used herein to qualify the relative affinity by which an engineered binding agent binds to a cognate functionalized amino acid residue. Specific binding typically means that an engineered binding agent binds to a cognate functionalized amino acid residue at least twice more likely that to a random, non-cognate functionalized amino acid residue (a 2:1 ratio of specific to non-specific binding). Non-specific binding refers to background binding, and is the amount of signal that is produced in a binding assay between an engineered binding agent and a non-cognate amino acid residue immobilized on a solid support. In some embodiments, specific binding refers to binding between an engineered binding agent and a cognate functionalized amino acid residue with a dissociation constant (Kd) of 500 nM or less.

Methods for Generating Barcoded Macromolecules from Single Cells.

Provided herein is a method for barcoding macromolecules from a sample comprising a population of cells, the method comprising the following steps:
  a. permeabilizing and optionally fixing cells, or nuclei of the cells, from the population of cells of the sample;
  b. optionally making genomic DNA of the permeabilized cells or nuclei at least partially accessible to nucleic acid hybridization;
  c. delivering cell barcode probes to the permeabilized cells and/or nuclei of the permeabilized cells, wherein a given cell barcode probe comprises a genome binding element shared among the cell barcode probes, and a cell barcode unique for a given cell barcode probe, and wherein the genome binding element hybridizes to a region in the genomic DNA, thereby forming a nucleic acid duplex between the genome binding element and the region of the genomic DNA in the cells and/or nuclei;
  d. removing cell barcode probes that are not bound to the genomic DNA from the cells or nuclei, whereby no more than a defined number of copies of the cell barcode probe remain in each cell or nucleus;
  e. partitioning the cells or nuclei into a plurality of compartments;
  f. amplifying the cell barcodes within compartments of the plurality of compartments, thereby forming amplified cell barcodes within the compartments; and
  g. attaching the amplified cell barcodes to the macromolecules within the compartments, thereby forming barcoded macromolecules.

In another embodiment, provided herein is a method for barcoding macromolecules from a sample comprising a population of cells, the method comprising the following steps:
  a. permeabilizing cells, or nuclei of the cells, from the population of cells of the sample;
  b. delivering reactive primers that are configured to be covalently attached to components of the permeabilized cells, thereby creating a plurality of attached primers;
  c. optionally making genomic DNA of the permeabilized cells or nuclei at least partially accessible to nucleic acid hybridization;
  d. delivering cell barcode probes to the permeabilized cells and/or nuclei of the permeabilized cells, wherein a given cell barcode probe comprises a genome binding element shared among the cell barcode probes, and a cell barcode unique for a given cell barcode probe, and wherein the genome binding element hybridizes to a region in the genomic DNA, thereby forming a nucleic acid duplex between the genome binding element and the region of the genomic DNA in the cells and/or nuclei;
  e. removing cell barcode probes that are not bound to the genomic DNA from the cells or nuclei, whereby no more than a defined number of copies of the cell barcode probe remain in each cell or nucleus;
  f. amplifying the cell barcodes using the plurality of attached primers, thereby forming amplified cell barcodes within the compartments; and
  g. attaching the amplified cell barcodes to the macromolecules within cells, thereby forming barcoded macromolecules.

In some embodiments of the disclosed methods, cells or nuclei are fixed with or before permeabilization. Exemplary methods of fixation are provided in Examples below.

In preferred embodiments of the disclosed methods, the genome binding element is the same for all CBPs delivered to the permeabilized cells and/or nuclei, so it hybridizes to the same region in the genomic DNA of the permeabilized cells and/or nuclei. In these embodiments, the permeabilized cells and/or nuclei share the same genome binding element.

In preferred embodiments of the disclosed methods, the cell barcode is unique for each CBP that is delivered to the permeabilized cells and/or nuclei, so different CBPs comprise different cell barcodes. When only one or two CBPs remain in a cell or nucleus after the removal step, unique cell barcodes of these CBPs are amplified and used to label cellular macromolecules of a given cell or nucleus, generating barcoded macromolecules. Unique cell barcodes of CBPs used in each cell or nucleus are preferred to ensure successful tracing of the barcoded macromolecules back to specific cells or nuclei after analysis of the barcoded macromolecules.

In a preferred embodiment of the disclosed methods, the CBP barcodes are comprised of a random nucleotide sequence (via oligonucleotide synthesis using a mixed base (e.g. N), much like a unique molecular identifier (UMI), but in this case the CBP contains a unique cellular identifier (UCI). In another embodiment, cellular barcode probes (CBPs) are comprised of UCI barcodes constructed through split-pool synthesis using chemical synthesis or enzymatic synthesis on beads and subsequent cleavage off of the beads (Delley and Abate. 2021. "Modular Barcode Beads for Microfluidic Single Cell Genomics." Scientific Reports 11 (1): 10857; Zilionis, et al., 2017. "Single-Cell Barcoding and Sequencing Using Droplet Microfluidics." Nature Protocols 12 (1): 44-73). In a preferred embodiment, cellular barcode probes (CBPs) constitute a library of unique barcodes such that the number of unique barcodes used in a given cellular labeling experiment exceeds the number of cells by at least tenfold or greater. In this way, "collisions" between cells with the same barcode are minimized effectively assigning most cells in the population (an associated analytes therein) to unique barcodes. In preferred embodiments, when barcodes are in excess of cells by ten-fold, there is roughly a 5% collision rate; and when in excess of cells by hundred-fold there is less than 0.5% collision rate. This can be explained by the statistics of the "birthday problem" with the resulting equation (Li and Humphreys. 2021. "Single Cell Technologies: Beyond Microfluidics." Kidney360 2 (7): 1196-1204):

$$P = \frac{N - D + D\left(\frac{D-1}{D}\right)^N}{N} \sim \frac{N}{2D} \text{ for large } N \text{ and } D,$$

where P=collision rate; N=number of cells; and D=number of unique barcodes. For D being tenfold greater than N, P is approximately 5%.

In preferred embodiments of the disclosed methods, the defined number of unique copies of CBP per cell is one or two copies; thus, after removing cell barcode probes that are not bound to the genomic DNA from the cells, only one or two copies of the cell barcode probe remain in each cell or nucleus. In some preferred embodiments of the disclosed methods, the defined number of copies is one copy.

As used herein, the defined number of copies is determined before delivering cell barcode probes (CBPs) to the permeabilized cells and/or nuclei, based on engineered binding of CBPs or specific genomic DNA-binding carriers comprising CBPs to gDNA of the permeabilized cells and/or nuclei. In one embodiment, specific genomic DNA-binding carrier carrying CBPs comprising CBPs binds to unique region of the gDNA that comprises a polymorphic sequence in one of the chromosomes; thus, only a single CBP copy will be bound to the gDNA via the carrier and remain in the permeabilized cells and/or nuclei after removing non-specifically bound or unbound copies (the defined number is one copy). In another embodiment, CBPs or specific genomic DNA-binding carriers comprising CBPs are engineered to bind to unique, non-repetitive region in the gDNA of the permeabilized cells and/or nuclei; in this embodiment, two CBP copies will be bound to the gDNA (due to duplicate chromosomes) and remain in the permeabilized cells and/or nuclei after removing non-specifically bound or unbound copies (the defined number is two copies). In yet another embodiment, CBPs or specific genomic DNA-binding carriers comprising CBPs are engineered to bind to a two-copy region in the gDNA of the permeabilized cells and/or nuclei; in this embodiment, four CBP copies will be bound to the gDNA (due to duplicate chromosomes) and remain in the permeabilized cells and/or nuclei after removing non-specifically bound or unbound copies (the defined number is four copies). Other embodiments include engineered CBPs or specific genomic DNA-binding carriers comprising CBPs that are bound to a repetitive region in the gDNA of the permeabilized cells and/or nuclei; in these embodiments, the defined number is 4, 6, 8, 10, 12, 14, 16, 19, 20, or more copies.

In the preferred embodiments of the disclosed methods, the sample can be any cellular sample from a biological organism or microorganism including tissue, blood cells, cell culture, microbial cells, etc. In some embodiments, these samples are fixed using any number of standard fixative procedures including formaldehyde-based fixation, Deep Eutectic Solvents (DESs), homo-bifunctional cross-linking agents, and others (disclosed in details below).

In preferred embodiments of the disclosed methods, the macromolecules being barcoded can be polypeptides, mRNA molecules or cDNA molecules. In preferred embodiments, the macromolecules being barcoded are components of cells from the sample, or derivatives of the components of cells from the sample (such as cDNA molecules are derivatives of cellular mRNA molecules).

In some embodiments of the disclosed methods, cell barcode probes are delivered to the permeabilized cells or nuclei, wherein a given cell barcode probe comprises a unique cell barcode and a common genome binding element shared among the permeabilized cells or nuclei, and wherein the genome binding element hybridizes to a region in the genomic DNA, thereby forming a nucleic acid duplex between the genome binding element and the genomic DNA in the cells or nuclei. In these embodiments, interaction between the region in the genomic DNA with the genome binding element does not induce single-strand breaks or double-strand breaks in the genomic DNA. In these embodiments, no cleavage of the genomic DNA is induced or triggered during delivering cell barcode probes to the permeabilized cells and/or nuclei of the permeabilized cells and during removing cell barcode probes that are not bound to the genomic DNA from the cells and/or nuclei, since nucleic acid hybridization does not require DNA cleavage. Also, in preferred embodiments, interaction between the region in the genomic DNA with the genome binding element occurs without exogenous enzymes, such as transposase.

In some embodiments, the disclosed methods further comprise releasing the barcoded macromolecules from the compartments. In one embodiment, compartments are formed by droplet emulsion, and after attaching the amplified cell barcodes to the macromolecules within the compartments, droplet emulsion is broken releasing the barcoded macromolecules. In some embodiments, released barcoded macromolecules are collected and used in a high-throughput macromolecule analysis assay, such as ProteoCode™ assay.

In some embodiments of the disclosed methods, the region in the genomic DNA used for attachment of CBPs is a non-repetitive region. In preferred embodiments, the non-repetitive region in the genomic DNA is a non-coding region. In other preferred embodiments, the non-repetitive region in the genomic DNA is a differentially methylated region that can be used for targeting of CBPs (more details provided below).

In the disclosed methods, removing cell barcode probes that are not bound to the genomic DNA from the cells and/or nuclei can be performed by various methods known in the art, for example, using post hybridization washing conditions developed for in situ hybridization methods. Exemplary non-limiting removal (washing) conditions are described in Examples 5-9. In some embodiments of the disclosed methods, the buffers used in post-hybridization washing and removal of CBPs that are not bound to the genomic DNA from the cells and/or nuclei are based on saline-sodium citrate (SSC) buffer (1×SSC buffer comprises 15 mM sodium citrate and 150 mM sodium chloride). The exact concentration of SSC in the post-hybridization washing solution may need to be optimized. Too much SSC in the washing solution will produce a poor washing effect of low stringency, while too little SSC will tend to wash all CBPs away from the cells and/or nuclei due to high stringency. Temperature and pH also influence the washing effect; increasing the temperature increases the stringency, and the pH determines the availability of the positive ions that counteract the repulsive negative force between the nucleic acid backbones of both the CBP and the genomic DNA. The inclusion of a mild non-ionic detergent, such as Tween-20, into the post-hybridization washing solution may increase washing efficiency. Some exemplary post-hybridization washing solutions based on SSC comprise 0.4×SSC at 72° C.; 2×SSC with 0.05% Tween at room temperature and solutions indicated in in Examples 5-9 below. Other (non-SSC-based) post-hybridization washing solutions can also be used that preferably comprise positively charged ions that counteract the repulsive negative force between the nucleic acid backbones of the CBP and the genomic DNA.

In the disclosed methods, partitioning of the cells or nuclei into the plurality of compartments can be performed by various methods known in the art, for example, disclosed in one of the following patent publications incorporated herein: US20180355348 A1, U.S. Ser. No. 11/441,179 B2, US20190040382 A1, US20210123103 A1, U.S. Ser. No. 10/774,370 B2. Methods of partitioning are also disclosed in Examples 13 and 14 below.

In the disclosed methods, amplification of the cell barcodes within compartments can be performed by various methods known in the art. A variety of known nucleic acid amplification techniques can be used to amplify cell barcodes of CBPs before attaching the amplified cell barcodes to the macromolecules within the cell. Exemplary non-limiting methods are described in Examples 14, 15, 17, 19 and 24. Other methods can be used as well, for example, disclosed in U.S. Ser. No. 10/428,326 B2, US20160257984 A1, US20180355348 A1 and U.S. Ser. No. 10/752,895 B2. In some embodiments of the disclosed methods, cell barcodes of CBPs can be amplified in situ within cells or nuclei (without compartmentalization). Such embodiments will be further discussed below.

In some embodiments of the disclosed methods, the genome binding element of each cell barcode probe comprises a PCR priming site adjacent to the cell barcode that is used to amplify the cell barcode at step (f).

In some embodiments of the disclosed methods, the sample is a spatial sample (e.g., a tissue slice), and wherein the sample is dissociated into a plurality of cells at step (e).

In some embodiments of the disclosed methods, when the sample is a spatial sample, each of the cell barcode probes further comprise a positional barcode different for at least some of the cell barcode probes.

In some embodiments of the disclosed methods, the cell barcode probes are delivered at step (c) from a spatially ordered array.

In some embodiments, the disclosed methods further comprise after step (b): (i) delivering a plurality of positional probes to the permeabilized cells or nuclei, wherein a given positional probe comprises a common targeting element configured to be attached to the macromolecules and a positional barcode different for each positional probes; and (ii) attaching positional probes from the plurality of positional probes to the macromolecules. In some embodiments, each of the amplified cell barcodes comprises a common region that is configured to hybridize (comprise complementary region(s) configured to form nucleic acid duplexes) to a region in the positional probes; and the method further comprises a step of performing a primer extension reaction to transfer the amplified cell barcodes to the positional probes attached to the macromolecules. In other embodiments, other ways of attaching amplified cell barcodes to positional probes are used. In some embodiments, the plurality of positional probes is delivered from a spatially ordered array.

In some embodiments of the disclosed methods, each compartment of the plurality of compartments comprises a compartment barcode configured to be attached to the macromolecules.

In some embodiments of the disclosed methods, during partitioning the cells or nuclei into the plurality of compartments at step (e), on average no more than one cell or nucleus comprising a cell barcode probe is comprised within a single compartment.

In some embodiments of the disclosed methods, attaching the amplified cell barcodes to the macromolecules within the compartments comprises: i) covalently attaching nucleic acid recording tags to the macromolecules or macromolecule derivatives of the cell; and (ii) attaching the amplified cell barcodes to the nucleic acid recording tags.

Barcoding methods presented herein can greatly improve the throughput of cells and genes detected during single cell RNA or protein sequencing. In some embodiments, cellular barcoding provides for a unique cellular barcode for all constituent analyte molecules within a single cell across a population of cells. Sample barcoding (indexing) allows for sample multiplexing, which provides certain advantages for single cell RNA or protein sequencing, such as increased sample throughput in a single assay, increased number of cells assayed, increased number of possible replicates in a single assay. Sample multiplexing refers to the labeling of a cell or nuclei sample with a sample barcode molecular tags and subsequently pooling the samples. This set of multiplexed samples can be processed together. Ideally or preferably, all macromolecules in the same cell are labeled with the same barcode, while distinct barcodes are used for different cells. After cell processing and macromolecule sequencing, molecular barcode information can be assigned to cells. Overall, barcoding and multiplexing can greatly reduce the processing time, technical batch effects, and library preparation costs, and lower the per-sample cost.

Cellular barcodes can be used to simultaneously tag a number of omic assays including scRNA-Seq assays to measure mRNA abundance, single cell protein assays such as CITE-Seq, AbSeq, or ProteoCode™ assays (scProt-Seq) to measure protein abundance and modifications, and scATAC-seq or scCut&Tag-seq (see Kaya-Okur, et al., 2019. "CUT&Tag for Efficient Epigenomic Profiling of Small Samples and Single Cells." Nature Communications 10 (1): 1930) to measure genomic DNA chromatin state. Various formats of these three Omic assays have been developed. Variations of scRNA-Seq include SMART-Seq, SMART-Seq2, STRT-seq, STRT-Seq-2i, SCRB-seq, mcSCRB-seq, Quartz-seq, Quartz-seq2, Cel-seq, Cel2, MARS-seq, Seq-Well, inDrops, Drop-seq, and other methods. These methods vary primarily in compartment format (plate, nanowell, droplets, etc.) and the single cell barcoding addition step (OligoT primer vs. tagmentation, vs. template switch oligo (TSO) (see Lafzi, Atefeh, et al., 2018. "Tutorial: Guidelines for the Experimental Design of Single-Cell RNA Sequencing Studies." Nature Protocols 13 (12): 2742-57). These difference affect whether full-length transcripts are sequenced and quantified, or just 5'/3' cDNA tag counting to measure abundance. Likewise, scATAC-seq and scCUT&Tag-seq also has various implementation architectures. Exemplary ProteoCode™ assays (scProt-Seq) are described in US 20190145982 A1.

In some embodiments of the disclosed methods, cell barcodes can be added at a late stage after macromolecule manipulation in which cells are processed individually at early steps (such as reverse transcription, preamplification and tagmentation). Preferably, cell barcodes are attached to macromolecules at an early stage after cell isolation. Then, all cells can be pooled into one single reaction for the following steps to save cost and labor. The current state-of-art method to label macromolecules in a massively parallel scale is to synthesize or load barcode molecules on beads such that one single bead carries up to a few million copies of the same barcode molecules, while the barcode sequences on different beads are different (Macosko, E. Z., et al. (2015) Highly Parallel Genome-wide Expression Profiling of Individual Cells Using Nanoliter Droplets. Cell, 161, 1202-1214).

Several DNA-based barcoding methods have been developed for sample multiplexing during single cell RNA sequencing (reviewed in Cheng J, et at., Multiplexing Methods for Simultaneous Large-Scale Transcriptomic Profiling of Samples at Single-Cell Resolution. Adv Sci (Weinh). 2021 September; 8(17):e2101229). The barcodes generated by the described methods take advantage of the following processing steps during single cell RNA sequencing. For example, such barcodes are polyadenylated at the 3' end and structurally similar to endogenous mRNA, so they can be captured by the poly(dT)-containing beads together with other mRNA molecules in single cell library construction. Alternatively, DNA barcodes are integrated with mRNA by PCR.

In some embodiments of the disclosed methods, the cellular barcode probe is comprised of a genomic binding sequence (GBS), a forward primer sequence, an optional sample hash barcode, a single cell barcode, and a reverse primer sequence (see FIG. 7A). The reverse primer sequence may also be appended with a "spacer" sequence for use in the ProteoCode NGPA or NGPS assay.

Figure 1:
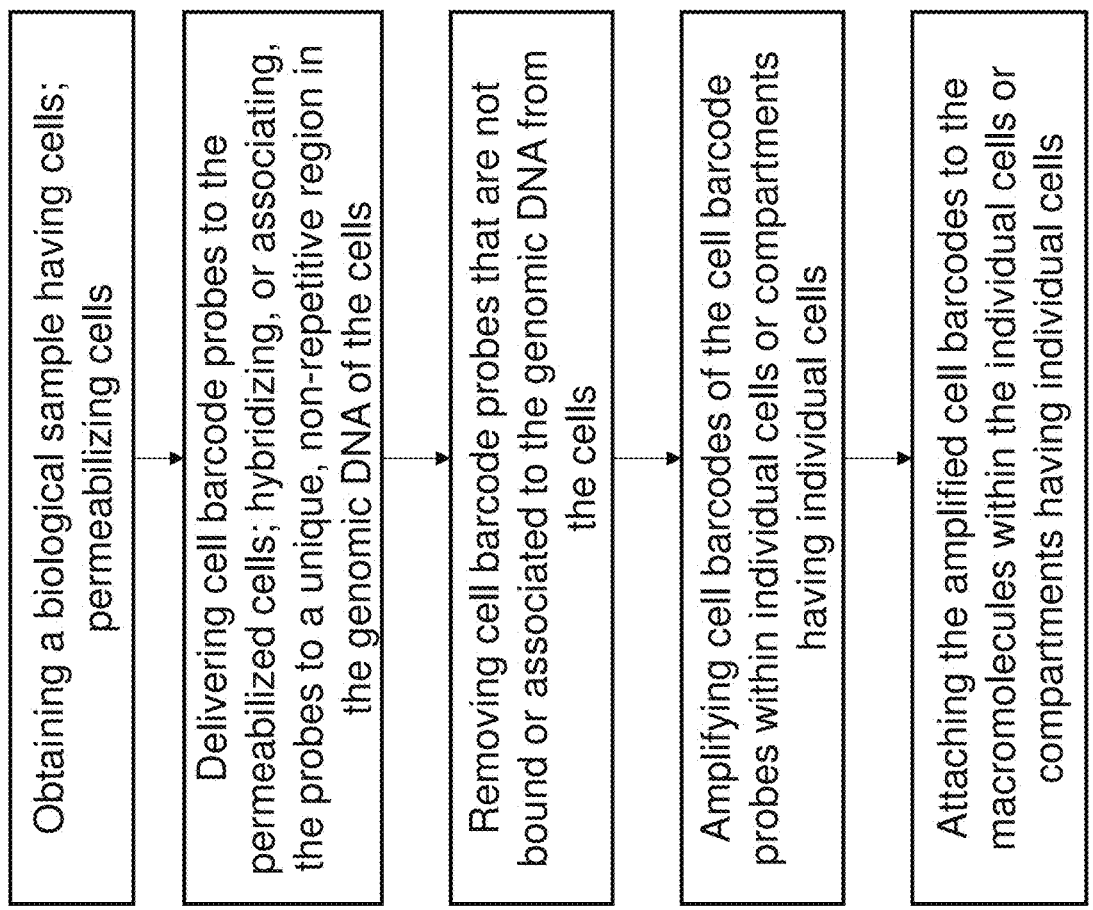
FIG. 1. Exemplary flow diagram for barcoding of macromolecules of individual cells showing key steps of the methods disclosed herein.

Exemplary flow diagram for barcoding of macromolecules of individual cells showing key steps of the disclosed methods is shown in FIG. 1.

Figure 2A:
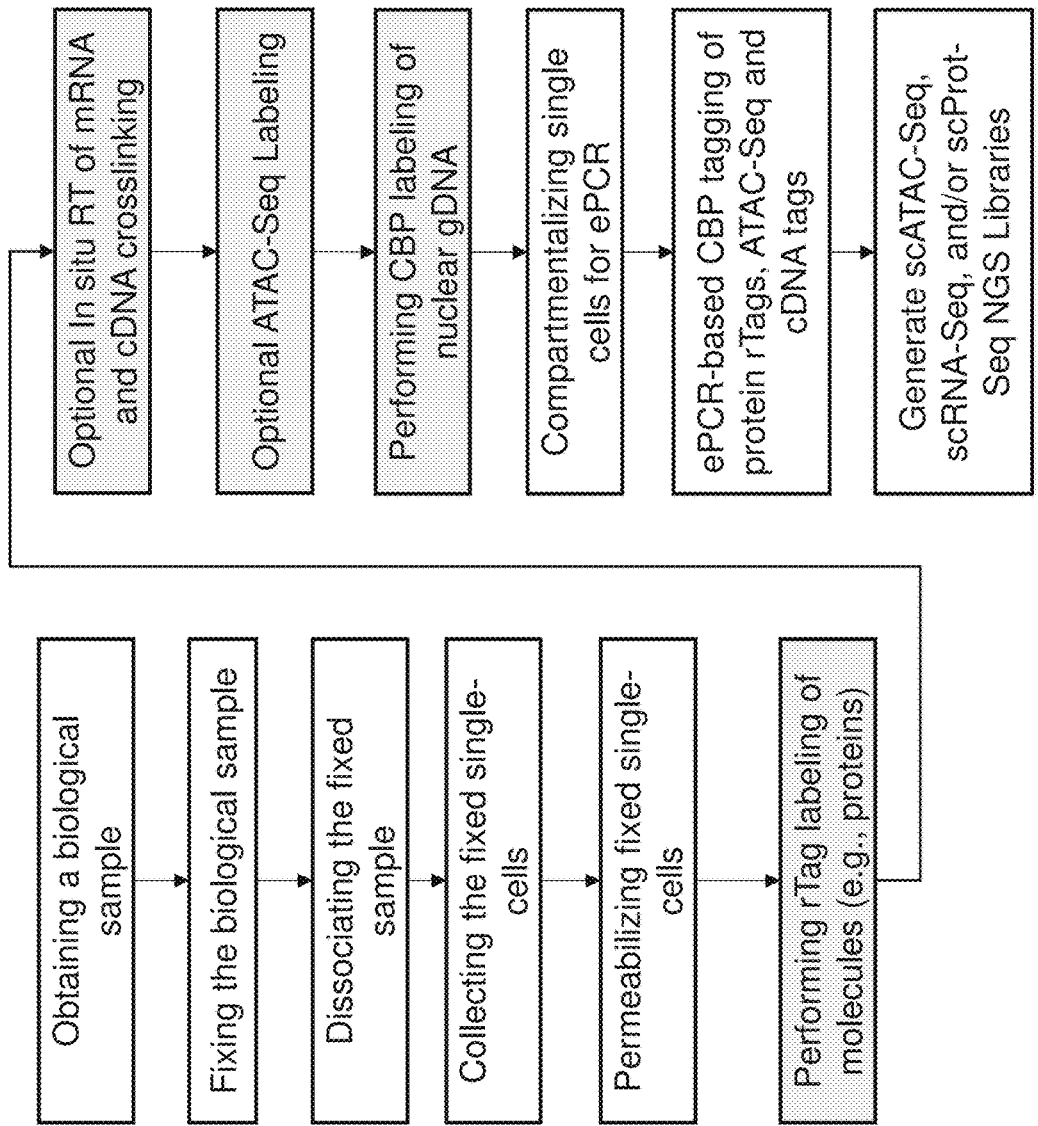
FIG. 2A-C. Exemplary flow diagrams for single cell multi-omics analysis using cellular barcoding.
Figure 2B:
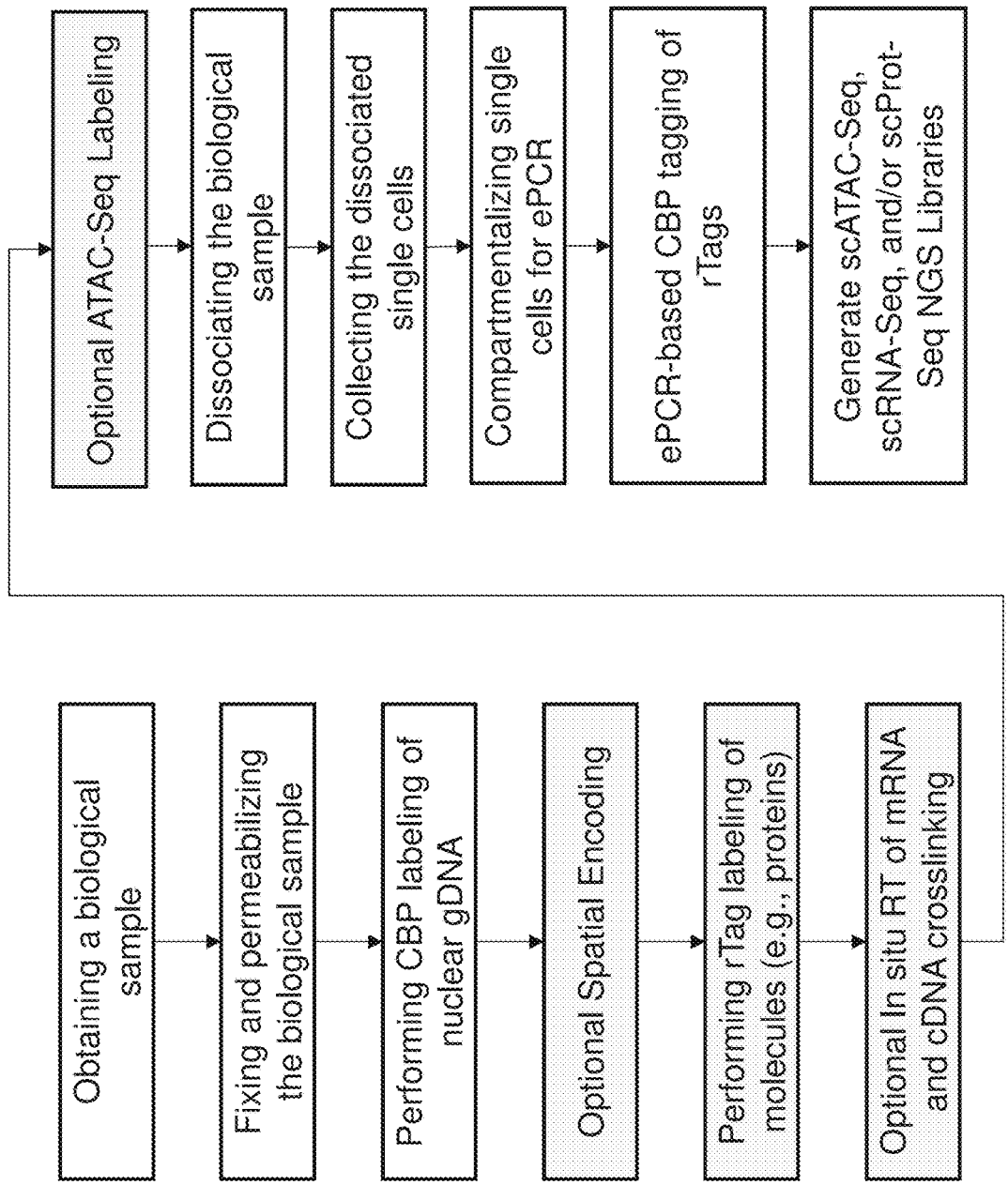
Figure 2C:
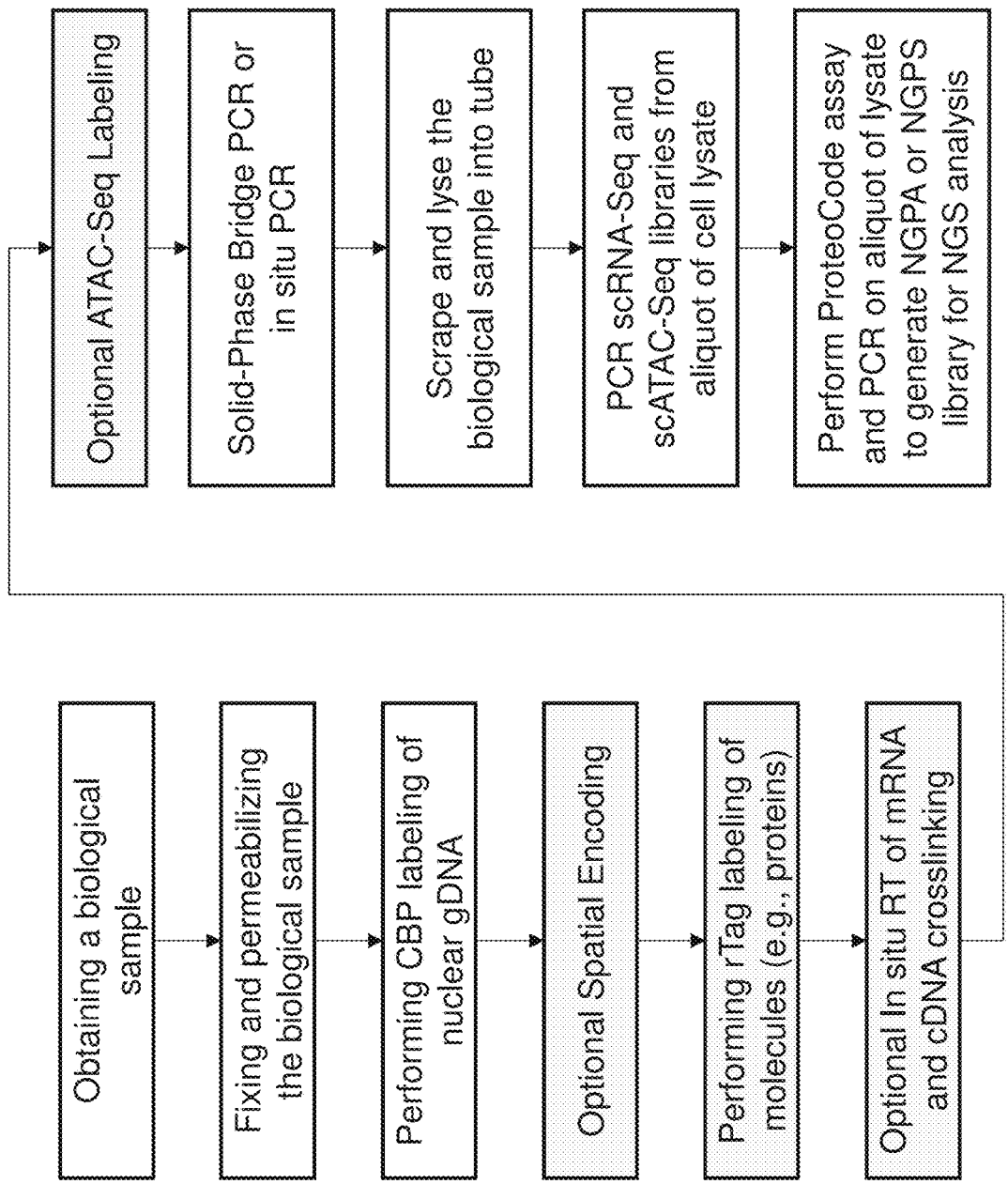

Another exemplary flow diagram for single cell multiomics analysis using nuclei cellular barcode tagging and ePCR is shown in FIG. 2A. In these embodiments, the cellular sample is dissociated using protease and/or DES treatment and sonication, or other methods known in the art. After collecting the disassociated single cells, the cells are permeabilized to enable "in situ" access to the cell and nuclear interior. The steps in grey can be performed in any order and include protein tagging with DNA recording tag stubs (rTag), in situ cDNA labeling, nuclear ATAC-Seq labeling, and nuclear labeling with a cellular barcode probe (CBP). FIG. 2B shows a similar workflow for a spatially arrayed biological sample, such as a tissue sample or adherent cells on a slide. An optional spatial encoding step can be implemented which attaches a spatial code to the CBP tag or DNA rTags. After spatial encoding, the single cells are dissociated and partitioned into compartments (e.g., emulsions, droplets, physical compartments, etc.). Emulsion PCR (ePCR) is used to incorporate the CBP tag to the ATAC-Seq, RNA-Seq, and Prot-Seq DNA tags. Finally, amplification primers are used to prepare scATAC-Seq, scRNA-Seq, and scProt-Seq libraries (for the following NGPA or NGPS assays). Other strategies to incorporate the CBP tag to macromolecules of individual cells can be used and some of them are disclosed below.

In some embodiments of the disclosed methods, the sample is a spatial sample, such as a tissue sample, and cells need to be dissociated from tissue sample for the following single cell analysis. A number of methods can be used to dissociate cells from tissue samples to create a population of dissociated cells. Papain treatment is used routinely on fresh tissues to dissociate the sample into discrete cells. A classic protocol by Huettner and Baughman is described in which tissues are incubated in Papain enzyme solution containing 116 mM NaCl, 5.4 mM KCl, 26 mM NaHCO, 1 mM NaHPO, 1.5 mM $CaCl_2$), 1 mM $MgSO2$, 0.5 mM ETDA, 25 mM glucose, 1 mM systeine, and 200 U papain (Cooper Biomedical, Malvern Pa.) for 1 hr at 37° C. (Huettner, J. E., and R. W. Baughman. 1986. "Primary Culture of Identified Neurons from the Visual Cortex of Postnatal Rats." The Journal of Neuroscience: The Official Journal of the Society for Neuroscience 6 (10): 3044-60). This reagent is provided in commercial form as the Worthington Papain Dissociation System (Worthington Biochemical Corporation). Other proteases of utility in assisting with tissue dissociation include: Liberases (Roche), Collagenase Type I, II, III, or IV, Trypsin, Proteinase K, Chymotrypsin, Elastase, Dispase, Pronase (Sigma).

In other embodiments of the disclosed methods, methods to simultaneously fix and dissociate cells can be employed. Rapid fixation maintains RNA and protein integrity. The ACME dissociation protocol is comprised of treating cells with a solution of acetic acid, methanol, and glycerol in water. Moreover, ACME-treated cells can be easily cryo-preserved in DMSO (10%) for later single cell processing. Additionally, ACME can be used to fix trypsin or papain dissociated cells as described above.

In some embodiments of the disclosed methods, tissue fixation can be achieved using Deep Eutectic Solvents (DESs) (U.S. Pat. No. 9,696,247 B2, included by reference), which can also can aid in tissue dissociation. DESs have the ability to uniquely fix cells and stabilize their molecular components such as RNA, DNA, proteins, carbohydrates, and metabolites. A commercial example of a DES-based fixation reagent is vivoPHIX (RNAssist, UK). In one embodiment, the first component is a quaternary ammonium or phosphonium compound such as choline chloride or N, N, N-trimethylglycine (betaine), and wherein the second component is a hydrogen bond donor, such as urea, trifluoroacetamide, or trifluoropropanamide. In a preferred embodiment, a deep eutectic solvent is comprised of choline chloride:3,3,3-trifluoroacetamide, optionally in a molar ratio of about 1:2; choline chloride:2,2-difluoro-2-phenylacet-amide, optionally in a molar ratio of about 1:1; choline chloride:trehalose, optionally in a molar ratio of about 1:1 and butyrylcholine iodide:urea, optionally in a molar ratio of about 1:2. In another embodiment, the addition of 1-33 mM, preferably ~10 mM of Zinc salts such as Zinc chloride, Zinc sulphate or Zinc citrate to the Choline chloride:Trifluoroacetamide improves cell fixation rates. In a preferred embodiment, the DES reagent also contains a detergent additive to aid in cell membrane permeabilization. Exemplar detergent additives include digitonin, saponin, TX-100, NP-40, and Tween-20. In another embodiment, the cells can be first cross-linked using exposure to a 1-6% paraformaldehyde solution for 10 min-1 hr at room temperature. Alternatively, the crosslinking can also be performed after DES treatment. In addition to fixing cells, DES solvents also weaken interactions between cells to facilitate dissociation of tissues into single cells in solution. In a preferred embodiment, cells or tissues are placed in a DES solvent and dissociated by sonication. In a preferred embodiment, tissues or cells that have been fixed with trimethylglycine:trifluoroacetamide (1:2) are dissociated into single cells under mild sonication preserving the integrity of macromolecules therein.

There are a variety of described methods to label a single copy locus within the genome using in situ hybridization (ISH) or fluorescence in situ hybridization (FISH) approaches (for example, disclosed in U.S. Pat. Nos. 5,447,841, 5,948,617; De Bau, L. E., and J. Gu. 1996. "IN SITU HYBRIDIZATION, IN SITU TRANSCRIPTION, AND IN SITU POLYMERASE CHAIN REACTION." Scanning Microscopy 10 (Article 3): 27-47; Beliveau, B. J., et al. 2015. "Single-Molecule Super-Resolution Imaging of Chromosomes and in Situ Haplotype Visualization Using Oligopaint FISH Probes." Nature Communications 6 (May): 7147). These methods typically employee nucleic acid probes which hybridize to a defined target region or regions within the genome. In some embodiments, hybridization of cellular barcode probes (CBPs) to target genomic sequences can be accomplished using standard ISH/FISH techniques. The key steps in ISH/FISH are generally as follows: 1) fixation and permeabilization of the cells or tissue (in solution or on a slide) to be analyzed; 2) pre-hybridization treatment of fixed/permeabilized cells or tissue to denature genomic DNA (gDNA) or render regions of the gDNA single stranded; 3) blocking of cells or tissue to minimize non-specific binding of FISH probes; 4) hybridization of FISH probes to the gDNA within the permeabilized cells/tissue; and 5) post-hybridization washes to remove non-specifically bound FISH probes. In some embodiments of described barcoding methods, the cell barcode of the CBP will be amplified and used to label constituent molecules within the cell for single cell applications.

Nucleic acid ISH/FISH probes are typically comprised of DNA, LNA, PNA, or RNA, and are designed to be complementary to the genomic sequence of interest. LNA-FISH and PNA-FISH can be used to generate probes exhibiting higher binding affinity, greater strand invasion properties, and shorter hybridization times than standard DNA probes with a resulting more intense FISH signal (Genet, M. D., et al., 2013. "Direct DNA and PNA Probe Binding to Telomeric Regions without Classical in Situ Hybridization." Molecular Cytogenetics 6 (1): 42).

A key challenge in ISH/FISH protocols is to efficiently hybridize the probe to intrinsically double stranded genomic DNA. A standard method to enable efficient hybridization genomic DNA is to denature the DNA to generate a ssDNA annealing site for the ISH/FISH probe (Shakoori, 2017, "Fluorescence In Situ Hybridization (FISH) and Its Applications." In Chromosome Structure and Aberrations, edited by Tariq Ahmad Bhat and Aijaz Ahmad Wani, 343-67. New Delhi: Springer India). This denaturation is typically accomplished using heat and chemical denaturants such a formamide or urea, or via the use of polar aprotic solvents such as ethylene carbonate (disclosed in U.S. Pat. No. 9,303,287 B2, U.S. Pat. No. 9,388,456 B2, U.S. Pat. No. 9,309,562 B2, U.S. Ser. No. 10/202,638 B2 all incorporated by reference). In one example, ethylene carbonate, a polar aprotic solvent, acts as an effective replacement for formamide in DNA hybridization buffers and improves both the rate of hybridization and reduces the background when included in hybridization and/or wash buffers (U.S. Pat. No. 9,309,562 B2, U.S. Ser. No. 10/202,638 B2, incorporated herein by reference).

In some embodiments of the disclosed methods, there is no need to separately denature the genomic DNA but rather the use of appropriate denaturing buffers (e.g., comprised of ethylene carbonate) or strand invading probes (e.g., PNA, recA-coated DNA) enables labeling of genomic DNA without using a specific denaturation step.

A large number of methods for more efficient labeling of genomic DNA within fixed/permeabilized cells or tissues have also been described (Genet, M. D., et al., 2013. "Direct DNA and PNA Probe Binding to Telomeric Regions without Classical in Situ Hybridization." Molecular Cytogenetics 6 (1): 42; Clyde, Dorothy. 2021. "Targeted Local DNA Denaturation with GOLD FISH." Nature Reviews. Genetics 22 (5): 267-267; Wang, et al., 2021, "Genome Oligopaint via Local Denaturation Fluorescence in Situ Hybridization." Molecular Cell 81 (7): 1566-1577.e8). These include physicochemical and enzymatic methods for creating localized regions of ssDNA at the locus of interest. Physicochemical methods include the use of strand invasion/displacement and D-loop formation tools such as using RecA coated probes, Bis-PNA strand openers, triple helix formation probes, and padlock probes to stabilize the invading probe structure (Matsunaga and Matsunaga, 2017, "FISH with Padlock Probes Can Efficiently Reveal the Genomic Position of Low or Single-Copy DNA Sequences." Cytologia 82 (4): 337-39; Yaroslavsky and Smolina, 2013, "Fluorescence Imaging of Single-Copy DNA Sequences within the Human Genome Using PNA-Directed Padlock Probe Assembly." Chemistry & Biology 20 (3): 445-53; Gruenig, et al., 2011, "Creating Directed Double-Strand Breaks with the Ref Protein: A Novel RecA-dependent Nuclease From Bacteriophage P1" The Journal of Biological Chemistry 286 (10): 8240-51). Improved bioinformatic probe design and alternative probe FISH probe architectures such as padlock probes have also improved signals from FISH assays (Yaroslavsky and Smolina, 2013, "Fluorescence Imaging of Single-Copy DNA Sequences within the Human Genome Using PNA-Directed Padlock Probe Assembly." Chemistry & Biology 20 (3): 445-53).

In some embodiments of the disclosed methods, CBPs are linear polynucleotides. In other embodiments, a padlock CBP can be employed. A padlock probe is a linear polynucleotide comprising complementary sequence arms to the target region; ligation (and optional extension) of the left and right arms upon target annealing generates a circularized padlock probe. Padlock probes combined with rolling-circle amplification enable fluorescence in situ hybridization (FISH) to reproducibly detect the genomic position of low or single-copy DNA sequences (Matsunaga and Matsunaga, 2017). The use of a padlock probe improves specificity during in situ hybridization by requiring ligation of the two arms of the padlock probe to create a circular construct.

In preferred embodiments of the disclosed methods, after delivering CBPs to the permeabilized cells and/or nuclei, and attaching the CBP to gDNA by forming a nucleic acid duplex or binding to a region in gDNA, excess of CBPs that includes unbound or nonspecifically bound CBPs are removed by washing. Some specific conditions for washing out excess of CBPs are disclosed in Examples 5, 8 and 12. In some preferred embodiments, the washing conditions post-CBP hybridization or binding to the gDNA, employ high-stringency washing conditions to removed mis-hybridized or non-specifically bound CBP complexes. Typical stringency parameters optimized in a wash optimization include the following: 1) salt concentration and type; 2) addition of denaturants such as formamide, ethylene carbonate, urea, DMSO, etc.; 3) temperature; and 4) presence and type of detergents employed. The choice of hybridization and wash stringency conditions will be inextricably linked to the probe design. In general, optimal hybridization stringency generally occurs at a temperature 10-25° C. lower than the probe melting temperature (Tm) in the hybridization buffer employed. Nucleic acid probe melting temperature is determined intrinsically by the nucleic acid composition and length of the probe, and extrinsically by the buffer composition and temperature.

Enzymatic methods of creating ssDNA regions include the use of restriction enzyme digestion (or CRISPER-Cas systems for targeted endonuclease digestion) combined with ExoIII to create ssDNA regions for hybridization, or restriction enzyme digestion combined with recA-mediated strand invasion at the ends of gDNA (Matsunaga and Matsunaga, 2017). CRISPER-Cas systems can also be used to target endonuclease cleavage at defined sites in the genome such as the ability to generate site-specific localized denaturation using a Cas9-topoisomerse fusion protein described in GOLD-FISH technique by Wang et al. (Wang, et al., 2021. "Genome Oligopaint via Local Denaturation Fluorescence in Situ Hybridization." Molecular Cell 81 (7): 1566-1577.e8).

The efficiency of probe annealing to gDNA during in situ hybridization is greatly enhanced by linearizing the gDNA in the region to which the probe anneals. A number of different methods have been employed to generate a ssDNA site for probe annealing. One method is to employ an exonuclease-based approach using site-specific restriction endonucleases to generate free dsDNA termini suitable as a substrate for exonuclease III (ExoIII) digestion of the 3' strand (Matsunaga and Matsunaga, 2017). These ExoIII-linearized regions can also be used as targets for both hybridization and ligation of CBPs appropriately designed. Namely, after endonuclease digestion, a given gDNA site can be targeted with a partially double stranded CBP having a 5' overhang such that CBP is ligated onto the nascent cleaved ss-gDNA sequence or is stably hybridized to the sequence (see FIG. 5). Alternative to exonuclease III digestion, the CBP can be coated with RecA to enable strand invasion of the 3' gDNA fragment at the blunt end of the digestion site.

Another method to locally expose a single strand region in the gDNA is to incubate the gDNA within the cells with Bis-PNA openers which will bind to the antisense strand to the probe and create an ssDNA region for linear or padlock probe annealing (Gyllborg, Daniel, et al., 2020, "Hybridization-Based In Situ Sequencing (HybISS): Spatial Transcriptomic Detection in Human and Mouse Brain Tissue." Nucleic Acids Research, Volume 48, Issue 19, Page e112).

More recently, methods of labeling genomic loci without the need to separately create ssDNA have also been described with the most prominent methods employing CRISPR-Cas based approaches using catalytically inactive Cas nucleases for locus-specific labeling, such as CASFISH, CAS-liveFISH, and CRISPR/Cas9-based RGEN-ISL. These approaches employ a catalytically inactive Cas nucleases (dCas) which serve as a gRNA-guided targeted binding proteins (see, for example, US 20190330678 A1, U.S. Ser. No. 10/767,168 B2, U.S. Ser. No. 11/124,782 B2, U.S. Ser. No. 10/858,639 B2 all incorporated by reference). The binding of the dCas-gRNA protein complex to the gDNA is quite stable (slow off-rate with dissociation half-life of more than 2 days), making it a suitable probe for in situ labeling approaches (Boyle, et al., 2017. "High-Throughput Biochemical Profiling Reveals Sequence Determinants of dCas9 off-Target Binding and Unbinding." *Proceedings of the National Academy of Sciences of the United States of America* 114 (21): 5461-66). In one example, inactive dCas9 nuclease is comprised of D10A and H840A endonuclease inactivating mutations relative to the *Streptococcus pyogenes* wildtype Cas 9 sequence; dCas9 (and various homologs) are available from several commercial sources such as Novateinbio, Applied Biological Materials (ABM), IDT, and New England Biolabs (NEB). The dCas9 variants are also commercially available with various N-terminal fusions to enable easy labeling with fluorophores or DNA tags including a dCas9 SNAP-tag version from NEB.

In some embodiments of the disclosed methods, other fusion proteins can also be attached to dCas9 such as a dCas9-SpyCatcher fusion that can be used to enable covalent labeling with a CBP-SpyTag conjugate. In some embodiments, CBP is directly attached to inactive dCas9 nuclease; in other embodiments, the gRNA can be labeled with CBP either by direct inclusion (e.g. gRNA comprises, or consists of CBP) or indirectly via hybridization. When the CBP is incorporated into the gRNA, the CBP can be annealed to a hybridization region on the gRNA or the gRNA can be comprised of the CBP RNA sequence. An exemplary resource for design of gRNAs for CRISPR targeting applications, including using dCas nucleases as specific gDNA-binding proteins, is the CHOPCHOP webtool and database (Labun, et al., 2021, "CRISPR Genome Editing Made Easy Through the CHOPCHOP Website." Current Protocols 1 (4): e46).

In some embodiments of the disclosed methods, a number of other catalytically inactive Cas9 variants and homologs can be employed for sequence-specific binding to gDNA, including more recently developed higher fidelity Cas9 variants with greatly reduced off-target activity including SpCas9-HF1(N497A, R661A, Q695A, Q926A) or eSpCas9-1.1 (N497A, R661A, Q695A, K848A, Q926A, K1003A, and R1060A) (Slaymaker, et al., 2016. "Rationally Engineered Cas9 Nucleases with Improved Specificity." *Science* 351 (6268): 84-88) and HypaCas9 (N692A/M694A/Q695A/H698A) (Kleinstiver, et al., 2016. "High-Fidelity CRISPR-Cas9 Nucleases with No Detectable Genome-Wide off-Target Effects." *Nature* 529 (7587): 490-95). Additionally, Cas9 variants with a relaxed PAM sequence requirement such as XCas9 variants may also be useful (Hu, et al., 2018. "Evolved Cas9 Variants with Broad PAM Compatibility and High DNA Specificity." *Nature* 556 (7699): 57-63). These gene variants are available from Addgene (Watertown, Mass.) and can be rendered catalytically inactive by porting D10A and H840A mutations or equivalent mutations (depending on homologue) to the respective Cas sequence. Cas9 nickases containing either D10A (coding strand) or H840A (non-coding strand) can also be employed for facilitating strand invasion.

In some embodiments of the disclosed methods, Cas9 homologues from different organisms can also be employed, including *Streptococcus pyogenes* (Sp), *Staphylococcus aureus* (Sa), *Neisseria meningitidis* (Nm or Nme), *Campylobacter jejuni (Cj), Streptococcus thermophilus (St), Treponema denticola (Td). These Cas9 homologues differ in their PAM sequence and gRNA requirement which needs to be considered in selection of the targeted sequence in gDNA. In other embodiments, the greater CRISPR-Cas nuclease systems (and inactive enzyme variants) can also be used for site-specific genomic DNA cleavage (or labeling via catalytically inactive engineered Cas nuclease). The CRISPR-Cas endonucleases systems are found among different species of bacteria, bacteriophages, and archaea and include Cas9, Cas12a, Cas12b, Cas14, CasX, CasPhi and others. Most of the Cas enzymes used for gene editing are classified as TypeII and are characterized by a single large Cas domain responsible for sgRNA binding and targeted endonuclease activity.

In other embodiments of the disclosed methods, in addition to catalytically inactive RNA-guided Cas9 proteins, other specific genomic DNA-binding carriers can be employed. Many different enzymes that recognize specific genomic DNA regions are known in the art and can be utilized in the disclosed methods to deliver CBPs to the permeabilized cells or cell nuclei. Some non-limiting examples of genome editing enzymes, such zinc finger nucleases, meganucleases and Transcription activator-like effector (TALE) nucleases (TALENs), are disclosed, in U.S. Pat. Nos. 9,695,432, 9,499,592, 9,393,257, 9,315,788, 9,187,758, 8,921,112, 8,906,607, 8,771,945, 8,697,853, 8,163,514, 8,119,381, 8,420,782, 8,440,432, 8,440,431, 7,888,121, 7,241,573, which can be appropriately modified and adopted for the barcoding methods disclosed herein.

In some embodiments of the disclosed methods, a nuclease-deficient Argonaute protein can be attached to a CBP to target specific genomic loci of individual cells as described by Chang et al in a technique called agoFISH (Chang, Lei, et al., 2019. "AgoFISH: Cost-Effective in Situ Labelling of Genomic Loci Based on DNA-Guided dTtAgo Protein." Nanoscale Horizons 4 (4): 918-23). In one embodiment, a guide DNA comprises a 5' phosphate and a CBP sequence that comprises a barcode and a target for dTtAgo protein. dTtAgo protein can specifically target (without cleavage) genomic DNA sequences using a ssDNA guide DNA of ~16-24 nt in length with a 5' phosphate moiety (Chang, Lei, et al., 2019). Attachment of CBP to dTtAgo can accelerate target finding compared to a naked CBP nucleic acid. Mutations in the catalytic aspartate residues of the Ago protein render it nuclease deficient, yet capable of target-specific binding of DNA in the presence of a guide DNA/ RNA. Exemplar engineered nuclease-deficient prokaryotic Argonaute proteins (pAgos) include engineered pAgos from thermophilic bacteria *Thermus thermophilus, Pyrococcus furiosus, Methanocaldococcus jannaschii*; and mesophilic bacteria *Clostridium butyricum, Limnothrix rosea, Synechococcus elongatus*, and *Kurthia massiliensis* (Kropocheva, Ekaterina, et al., 2021. "A Programmable pAgo Nuclease with Universal Guide and Target Specificity from the Mesophilic Bacterium *Kurthia Massiliensis*." Nucleic Acids Research 49 (7): 4054-65).

In some embodiments of the disclosed methods, Prime Editing (PE) can be adapted for inserting CBPs into a gDNA. In PE, a "nicking" Cas9 (H840A) fused to a reverse transcriptase employs a 3'-extended guide RNA, termed pegRNA, which enables targeted insertion of a region at the 3' end of the pegRNA copied onto the non-complementary nicked strand via its 3' flap acting as a primer for RT extension (Anzalone, et al., 2019, "Search-and-Replace Genome Editing without Double-Strand Breaks or Donor DNA." Nature 576 (7785): 149-57).

In some embodiments of the disclosed methods, after delivery of a CBP to permeabilized cells, the genome binding element of the CBP hybridizes to a non-repetitive region in the genomic DNA (gDNA) of the cells, thereby forming hybridization duplexes between the genome binding element and the gDNA in the cells.

In some embodiments of the disclosed methods, hybridization between the genome binding element of the CBP and gDNA within fixed/permeabilized cells is achieved using chemical denaturation or an enzymatic process to render target regions of gDNA at least partially accessible to nucleic acid hybridization. Partially accessibility to nucleic acid hybridization refers to a partial unfolding of double stranded gDNA, which exposes one of the strands to interaction with a portion of CBP and eventually to formation of nucleic acid duplex between the portion of CBP and one of the strands of gDNA. Exemplary methods to produce partially accessibility to nucleic acid hybridization are disclosed in Examples below, and other methods can also be used. gDNA of the permeabilized cells or nuclei can be made partially accessible to nucleic acid hybridization in a separate step of the disclosed barcoding methods, or it can be made during hybridization with CBPs. In preferred embodiments, partially accessibility to nucleic acid hybridization can be achieved by utilizing reaction conditions designed for nucleic acid hybridization, such as conditions described in Example 5.

In some embodiments of the disclosed methods, the CBPs are designed to hybridize to non-transcribed regions of the genome to prevent interaction with transcribed mRNA in the cell.

In some embodiments of the disclosed methods, hybridization of CBPs can be accomplished by in situ hybridization methods as described in U.S. Pat. Nos. 5,447,841 A and 5,948,617 A. Namely, the major steps involved in in situ hybridization are as follows: 1) cell fixation and permeabilization; 2) pre-hybridization treatment to at least partially denature gDNA and increase gDNA accessibility; 3) optional blocking step to reduce background; 4) hybridization of probe to gDNA within cells; 5) and post-hybridization washes to remove non-specifically bound probes. After in situ hybridization of the CBPs, the cells can be disassociated (e.g., tissue section on slide) and employed in single cell barcoding methods described below.

In some embodiments of the disclosed methods, the genome binding element of CBP comprises modified nucleotides or nucleotide analogs capable of hybridizing (forming multiple hydrogen bonds) with genomic DNA. In some embodiments, the genome binding element comprises a PNA (peptide nucleic acid) molecule (see e.g., Example 7 below). The advantage of using PNAs is reducing size of the genome binding element. In some embodiments, the genome binding element of CBP comprises between 5 and 100 nucleotides or nucleotide analogs. In some embodiments, the genome binding element of CBP comprises between 10 and 100, between 10 and 70, between 10 and 50, between 10 and 40, between 10 and 30, between 20 and 70, or between 20 and 50 nucleotides or nucleotide analogs.

In some embodiments of the disclosed methods, cell fixation is accomplished with exposure to formaldehyde/ para-formaldehyde which cross-links cellular proteins and anchors soluble proteins to the cytoskeleton to preserve cell structure. Additionally, formaldehyde fixation maintains cell morphology and enables generation of robust ISH signals. In some embodiments, permeabilization of intact cells can be achieved when formaldehyde is used in combination with a membrane solubilizing reagent such as nonionic detergents (e.g., Tween20) and alcohols (e.g., methanol). Alcohols fix cells by protein precipitation/denaturation and can be enhanced when used in combination with acetic acid (Carnoy's fixative or ACME fixative).

In some embodiments of the disclosed methods, ISH probe binding to a haploid imprinted loci or X-chromosome inactivated loci using MeFISH can be utilized for delivering a single copy of CBPs to gDNA of the permeabilized cells. In mammals, a small subset of genes and intergenic regions are differentially methylated between parental alleles leading to parent-of-origin-specific gene expression. Imprinted loci on the genome are comprised of symmetric CpG methylation of both strands of one parental allele and non-methylation at the other parental allele (Tucci, et al., and Erice Imprinting Group, 2019, "Genomic Imprinting and Physiological Processes in Mammals," Cell, 176 (5): 952-65). Using the fact that only one of the two parental alleles is imprinted or methylated, one can use MeFISH-like approaches to specifically hybridize and cross-link a CBP to the methylated locus enabling tagging of the genome with only a single copy of the CBP per cell.

MeFISH works by employing DNA probes designed with an adenine base labeled with a bipyridyl chelator moiety directly facing the cytosine base being queried with regard to its methylation status (see FIG. 10). An adenine base labeled with a bipyridyl moiety chelates osmium tetroxide and covalently attaches to opposing methyl cytosine bases (see Buchmuller, et al., 2021. "Programmable Tools for Targeted Analysis of Epigenetic DNA Modifications." *Current Opinion in Chemical Biology* 63 (August): 1-10). After probe hybridization, the cells are incubated with osmium tetroxide, which is chelated by the bipyridyl group on the probe and will form a covalent adduct with methyl cytosine, but not with unmethylated cytosine, effectively cross-linking the probe in place. Uncross-linked probe is washed away. In some embodiments, CBPs can be designed to label on a single locus with one copy of the CBP probe per cell.

Exemplar imprinted genes and genomic regions in humans which can be used as CBP probe targets for single copy genomic labeling are shown below (based on Tucci, et al., 2019, Cell, 176 (5): 952-65): DIRAS3, IL12RB2, RNU5D-1, AGO1, UTS2, THAP3, CACNA1E, CYP2J2, ACOT11, LRRTM1, TMEM247, THUMPD2, PAX8, PAX8-AS1, DNAH7, ICA1L, GPR1, GPR1-AS, ZDBF2, MRPL44, SPHKAP, USP4, SLC4A7, ZNF385D, EFCC1, RAB7A, MCCC1, FGF12, MFI2, GPR78, STX18-AS1, PDE6B, SH3BP2, NAP1L5, GRID2, SFRP2, FAM149A, FRG1, PLEKGH4B, RHOBTB3, NUDT12, VTRNA2-1, ZNF354C, CUL7, MDGA1, MOCS1, C6orf47, RNF144B, CD83, FAM50B, FAM50B-AS, AIM1, LIN28B, PHACTR2, HYMAI, PLAGL1, SLC22A2, SLC22A3, PLG, KIF25, GRB10, RAPGEF5, SCIN, THSD7A, CALCR, TFPI2, SGCE, PEG10, PDK4, CPA4, MEST, MESTIT1, COPG2IT1, KLF14, KLHDC10, AGBL3, PRKAG2, PTK2B, R3HCC1, CLDN23, DLGAP2, PKIA, ZFAT, ZFAT-AS1, PEG13, PSCA, NAPRT1, TRAPPC9, KCNK9, DENND3, GLIS3, PGM5P3-AS1, EXD3, PTCHD3, ITGA8, PROSER2, PROSER2-AS1, JMJD1C, AIFM2, USMG5, VWA2, INPP5F_V2, CPXM2, ACCS, ALKBH3, MAPK8IP1, WT1-Alt transcript, WT1AS, LINC00294, miR-675, IGF2, IGF2AS, INS, KCNQ1, KCNQ1OT1, KCNQ1DN, CDKN1C, PHLDA2, miR-483, SLC22A18, ZNF215, NAV2, ART5, OVCH2, RNF141, IRF7, ANO1, PAK1, VSTM5, ZC3H12C, SPA17, NTM, OPCML, TIGAR, CACNA1C, WIF1, N4BP2L1, RB1, RB2, LPAR6, DLEU7, KLHL1, FGF14, PCK2, PAPLN-AS1, DLK1, MEG3, MIR337, RTL1, MEG8, miR-134, PiRNAs, MKRN3, MAGEL2, NDN, NPAP1, SNURF, SNRPN, SNORD107, SNORD64, SNORD108, SNORD109A, SNORD116@, IPW, SNORD115@, SNORD109B, UBE3A-AS, UBE3A, PWRN1, SNHG14, H73492, RYR3, DNM1P35, RASGRF1, FAM174B, IRAIN, LRRK1, SIAH1, ZNF597, NAA60 isoform 1, PDPR, ZFP90, CLEC3A, NLGN2, SEPT4, ZNF714, AXL, DNMT1, SIPR2, ICAM1, FDX1L, ZNF833P, GNG7, ANO8, CACNA1A, C19MC, ZNF331, Anti-MIR371-MIR373, MIR512-1, ZIM2, PEG3, MIMT1, ZNF542P, CST1, PSIMCT-1, ACTL10, NNAT, BLCAP, ZHX3, L3MBTL, SGK2, CYP24A1, NESP55, GNASXL, Epxon-1A, GS-alpha, SANG, miR-296, miR-298, GDAP1L1, PRMT2, CBR1, TPTEP1, ARVCF, CACNA11, NHP2L1, SLC9A7.

In some embodiments of the disclosed methods, CBP probe binding using ISH protocols (via nucleic acids, DNA binding proteins, etc.) to an altered cancer-specific genomic lesion (variant or epigenetic modification) within the permeabilized cells enables targeted analysis of cancerous cells such as CTCs or other tumorous cells. Only cells with the genomic alterations will be labeled with CBPs and subsequently generate NGS multi-omic libraries for analysis. These cancer-specific probes can be designed to specific genetic lesions such as mutational variants, or in a preferred embodiment, be designed to bind in a methylation-dependent manner. Tumor suppressor genes such as p53, BRCA1/BRCA2, APC, PTEN, etc. are known to undergo hypermethylation, some in an allele-specific manner, during tumorigeneses forming a suitable target by CBP labeling.

In yet another embodiment, provided herein is a method for barcoding macromolecules from a sample comprising a population of cells, the method comprising the following steps:

a. permeabilizing cells, or nuclei of the cells, from the population of cells of the sample;

b. delivering a specific genomic DNA-binding carrier comprising a cell barcode probe to the permeabilized cells or nuclei, wherein a given cell barcode probe comprises a cell barcode unique for each cell or nucleus, and a priming site, and wherein the specific genomic DNA-binding carrier specifically binds to a region in the genomic DNA of the cells or nuclei;

c. removing specific genomic DNA-binding carriers that are not bound to the genomic DNA from the cells or nuclei, whereby no more than a defined number of copies of the cell barcode probe remain in each cell or nucleus;

d. amplifying the cell barcodes that were not removed from the cells or nuclei at step (c), thereby forming amplified cell barcodes; and e. attaching the amplified cell barcodes to the macromolecules, thereby forming barcoded macromolecules.

In some embodiments of the disclosed methods, the specific genomic DNA-binding carrier comprises a catalytically inactive Cas nuclease, a TALE protein or a zinc-finger protein.

In some embodiments of the disclosed methods, amplifying the cell barcodes at step (d) comprises providing conditions for hybridization between the cell barcode probes and a plurality of attached primers.

In preferred embodiments of the disclosed methods, the defined number of copies of CBP is one copy or two copies; thus, after removing specific genomic DNA-binding carriers that are not bound (or nonspecifically bound) to the genomic DNA from the cells, only one copy or two copies of the cell barcode probe remain in each cell.

In the disclosed methods, the macromolecules being barcoded can be polypeptides, mRNA molecules or cDNA molecules. In preferred embodiments, the macromolecules being barcoded are components of cells from the sample, or derivatives of the components of cells from the sample (such as cDNA molecules are derivatives of cellular mRNA molecules).

In some embodiments of the disclosed methods, the region in the genomic DNA used for attachment of CBPs is a non-repetitive region. In preferred embodiments, the non-repetitive region in the genomic DNA is a non-coding region. In other preferred embodiments, the non-repetitive region in the genomic DNA is a differentially methylated region that can be used for targeting of CBPs (more details provided below).

In some embodiments, each of the cell barcode probes further comprises a positional barcode different for at least some of the cell barcode probes.

In some embodiments, the specific genomic DNA-binding carrier(s) is/are delivered at step (b) from a spatially ordered array.

In some embodiments of the disclosed methods, step (d) further comprises the following steps: (i) partitioning the cells or nuclei into a plurality of compartments; and (ii) amplifying the cell barcodes within compartments of the plurality of compartments, thereby forming amplified cell barcodes within the compartments.

In some embodiments, during partitioning the cells or nuclei into the plurality of compartments, on average no more than one cell or nucleus comprising a cell barcode probe is comprised within a single compartment.

In some embodiments, at step (d) the cell barcodes are amplified in situ within cells or nuclei, and without partitioning the cells or nuclei into the plurality of compartments.

In some embodiments, the cell barcode probe is integrated in the genomic DNA of the cells or nuclei at step (b).

In some embodiments, the genome binding element of each cell barcode probe comprises a PCR priming site adjacent to the cell barcode that is used to amplify the cell barcode at step (d).

In some embodiments, the sample is a spatial sample (e.g., a tissue slice).

In some embodiments, each of the cell barcode probes further comprise a positional barcode different for at least some of the cell barcode probes.

In some embodiments, each compartment of the plurality of compartments comprises a compartment barcode configured to be attached to the macromolecules.

In some embodiments, attaching the amplified cell barcodes to the macromolecules within the compartments comprises: i) covalently attaching nucleic acid recording tags to the macromolecules or macromolecule derivatives of the cell; and (ii) attaching the amplified cell barcodes to the nucleic acid recording tags.

In some embodiments, programmable DNA binding proteins such as designed TALE (dTALE) or zinc-finger proteins can be used to bind a specific DNA locus within the genome. dTALE proteins are characterized by tandem 34-amino acid repeats which recognize one base pair each and direct sequence-specific DNA binding through designed concatenation of repeat variable di-residues (RVDs). The particular order and composition of the RVDs comprise a TALE DNA binding code' in which robust comprehensive rules of DNA recognition are known; A NI binds A, HD binds C, NN/NK binds G, and NG binds T. As such, sequence-specific DNA binding can be achieved by simple assembly of these 4 or 5 individual RVD repeats with desired base specificities. dTALE proteins comprised of NG, HD and NN RVDs bound their targets with high affinity (160 pM-2.4 nM) (Meckler, et al. 2013. "Quantitative Analysis of TALE-DNA Interactions Suggests Polarity Effects." *Nucleic Acids Research* 41 (7): 4118-28). dTALES can also be designed to be methylation specific enabling binding to a non-methylated allele and not to a methylated allele allowing haploid genome labeling (Tsuji, et al., 2018. "Sequence-Specific 5mC Detection in Live Cells Based on the TALE-Split Luciferase Complementation System." *The Analyst* 143 (16): 3793-97). Crosslinking of the dTALE proteins to the bound DNA will stabilize the complex. This can be accomplished using a psoralen cross-linker attached to the dTALE protein. Psoralen intercalates AT dinucleotides and crosslinks juxtaposed Ts' in an AT dinucleotide duplex (Bornet, et al., 1995. "Solution Structure of Oligonucleotides Covalently Linked to a Psoralen Derivative." *Nucleic Acids Research* 23 (5): 788-95). Exemplary methods for preparing Transcription activator-like effector (tale) libraries and determining a TALE that binds to a given nucleotide sequence are disclosed in US20160369268 A1 (incorporated herein).

In some embodiments, there is no partitioning of the cells or nuclei from the cells into a plurality of compartments before amplification of the cell barcodes. In these embodiments, CBPs can be amplified by in situ PCR (as described in Bagasra, Omar. 2007. "Protocols for the in Situ PCR-Amplification and Detection of mRNA and DNA Sequences." Nature Protocols 2 (11): 2782-95; Athman, et al., 2014. "Protocol: A Fast and Simple in Situ PCR Method for Localising Gene Expression in Plant Tissue." Plant Methods 10 (September): 29) or bridge amplification (see, for example, U.S. Pat. No. 7,115,400 B1). For example, for tissue section sample, the CBP hybridized to gDNA is amplified and subsequently attached to the constituent macromolecules containing a DNA recording tag using in situ PCR techniques as described in Bagasra, 2007, "Protocols for the in Situ PCR-Amplification and Detection of MRNA and DNA Sequences", Nature Protocols 2 (11): 2782-95. Namely, the recording tags ($CBP_F$) are attached to macromolecules (e.g. proteins) using standard bioconjugation techniques as described in Example 20. The rTag $CBP_F$ primer attached to the macromolecule acts a primer in the in situ PCR reaction comprised of solution phase $CBP_F$ and $CBP_R$ primers where $CBP_R$ is in excess. In a preferred embodiment, the UMIs are present on the rTag prior to writing of the CBP tag. In another preferred embodiment, the rTags are comprised of pseudo-complementary bases (e.g., 2-aminoadenine and 2-thiothymine) to minimize rTags non-specifically priming on each other (Lahoud, Georges, et al., 2008. "Properties of Pseudo-Complementary DNA Substituted with Weakly Pairing Analogs of Guanine or Cytosine." *Nucleic Acids Research* 36 (22): 6999-7008). In an alternate embodiment, the rTag tags are installed on analytes prior to CBP ISH labeling. Alternatively, both $CBP_F$ and $CBP_R$ primers can be attached to the macromolecules (e.g., proteins) and act as solid-phase primers in a classical bridge amplification or "cluster amplification" process to effectively transfer, in situ, the genomic CBP information to the macromolecules (see U.S. Pat. No. 7,115,400 B1) within the cell or nuclei. Essentially, a CBP cluster will be formed at the site of the cell, and if the cells are arrayed on a 2D surface such as in a tissue section on a slide, these clusters will grow out from the nuclear locations within the cells.

Feasibility of this approach is supported by the following approximate calculation of the density of recording tag primers within a cell. The average mammalian cell is about 20 um in size with an approximate average volume of 3000 um$^3$; within this volume are about 10 billion proteins and assuming each protein is labeled with ten recording tags, this yields $10^{11}$ recording tags per cell. This translates to a recording tag concentration of ~10 uM, a very high concentration of solid-phase primers. Even assuming a 1% efficiency, this is still 100 nM concentration of primers which is roughly an intra-probe distance of 10 nm (Milo, Ron, and Rob Phillips. 2015. Cell Biology by the Numbers. Garland Science).

In some embodiments, amplifying the cell barcodes comprises a) delivering reactive primers that are configured to be covalently attached to components of the permeabilized cells, thereby creating a plurality of attached primers; and b) amplifying the cell barcodes using the plurality of attached primers, thereby forming amplified cell barcodes.

In some embodiments, delivery of CBPs to the permeabilized cells and/or nuclei as a part of specific genomic DNA-binding carrier followed by specific binding to a region in the genomic DNA of the cells and/or nuclei using dCas9 or TALE protein, can be combined with in situ (bridge) amplification of CBPs using reactive primers that delivered to the cells and/or nuclei and are configured to be covalently attached to components of the permeabilized cells. In these embodiments, there are no partitioning of the cells and/or nuclei into a plurality of compartments (compartmentalization step is not present).

In some embodiments, both cDNA from transcribed mRNA and proteins are labeled with recording tags comprised of a $CBP_F$ a primer. In a preferred embodiment, the cDNA recording tag is distinguished from the protein recording tag by a sequence identifier. This sequence identifier can be used to enrich and separate the final recording tag NGS library elements derived from preparation and processing of cDNAs vs. proteins.

In some embodiments, CBP or cell barcode can comprise either single stranded or double stranded polynucleotide. In some embodiments, CBP or cell barcode can comprise either DNA or RNA polynucleotide. In some embodiments, CBP comprises a polynucleotide having between 20 and 30 nucleotides (nt), between 20 and 40 nt, between 20 and 50 nt, between 20 and 100 nt, between 20 and 200 nt, or between 50 and 200 nt. In some embodiments, CBP consists of a polynucleotide having between 20 and 30 nt, between 20 and 40 nt, between 20 and 50 nt, between 20 and 100 nt, between 20 and 200 nt, or between 50 and 200 nt. In some embodiments, a cell barcode contains between 5 and 20 nt, between 5 and 30 nt, between 10 and 20 nt, or between 5 and 100 nt.

Amplified CBPs can be attached to target macromolecules including mRNA/cDNA and proteins by a variety of methods known in the art. Amplified CBPs can be attached to target macromolecules covalently or non-covalently, such as via nucleic acid hybridization.

In some embodiments, DNA recording tag stubs (rTags) are joined to target macromolecules via a chemical bioconjugation reaction (e.g. using a heterobifunctional agent to attach click-reactive reactive handles to a native biopolymer and enable subsequent click chemistry addition of desired tags containing a cognate reactive handle). Exemplary reactions include click chemistry reactions, such as the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). In some embodiments, m-tetrazine or phenyl tetrazine (pTet) is used in an iEDDA click chemistry reaction. In one case, a target polypeptide is labeled with a bifunctional click chemistry reagent, such as alkyne-NHS ester (acetylene-PEG-NHS ester) reagent or alkyne-benzophenone to generate an alkyne-labeled polypeptide. In some embodiments, an alkyne can also be a strained alkyne, such as cyclooctynes including Dibenzocyclooctyl (DBCO).

In some embodiments, DNA recording tag stubs (rTags) comprise a first reactive handle and target macromolecules comprise a second reactive handle, so that attachment of rTags to the target macromolecules is a bioorthogonal reaction. In some embodiments, the first and/or second reactive handle comprises a bio-orthogonal reactive group (e.g., click chemistry reagent). In some embodiments, the bio-orthogonal reactive group is a reaction partner for an inverse electron demand Diels-Alder (IEDDA) reaction. Some examples of bioorthogonal reactions that can be utilized herein are disclosed, for example, in U.S. Pat. No. 8,236,949 B2, U.S. Pat. No. 9,169,283 B2, U.S. Ser. No. 10/611,738 B2, U.S. Ser. No. 10/442,789 B2, and in Fox J M, et al., "General, Divergent Platform for Diastereoselective Synthesis of trans-Cyclooctenes with High Reactivity and Favorable Physiochemical Properties. Angew Chem Int Ed Engl. 2021 Mar. 19".

In other embodiments, DNA recording tag stubs (rTags) are attached to target macromolecules indirectly, such as via a linker of various lengths and flexibility (e.g., PEG linker). In some embodiments, target macromolecules are polypeptide that are joined to a bait nucleic acid molecule which hybridizes with at least a portion of the amplified CBPs.

In a particular embodiment, proteins within permeabilized cells are labeled with short DNA recording tag stubs (rTags) comprised of a short CBP amplification primer, such as $CBP_F$ or $CBP_R$, or combination thereof (see FIG. 4A-E). These recording tag primers receive CBP information from the genomic CBP tag during a CBP amplification reaction such as via emulsion PCR, in situ PCR, or bridge amplification. In a preferred embodiment, the recording tags are coupled to proteins using an amine bioconjugation chemistry using a one- or two-step process. In a one-step process, activated DNA comprised of amine-reactive chemistries such as ethynyl moieties or N-hydroxysuccinimide (NHS) moieties are employed to label lysine amines on proteins; a number of other bioconjugation methods for lysine labeling are described by Hermanson (Hermanson, Greg. 2013. "Bioconjugate Techniques: Third Edition." Bioconjugate Techniques: Third Edition, August, 1-1146). In a two-step process, click-enabled heterobifunctional linkers comprised of an amine-reactive component and a click chemistry component are used to first activate the lysine amines on the constituent proteins, in a second step, a DNA tag is covalently attached using click chemistry. Exemplary click chemistries include CuAAC, SPAAC, iEDDA chemistrie (Oliveira, et al., 2017. "Inverse Electron Demand Diels-Alder Reactions in Chemical Biology." Chemical Society Reviews 46 (16): 4895-4950).

In some embodiments, barcoded macromolecules are polypeptide analytes; attaching the amplified cell barcodes to the polypeptide analytes can be achieved using different amino acid side-chain specific chemistries. In some embodiments, chemical coupling between the nucleic acid molecule and amino acid residues is achieved through amino acid-specific chemical modification methods known in the art; for example, lysine residues can be functionalized with NHS-ester chemistry and cysteine residues selectively interact with the maleimide group. Examples of amino-acid-specific chemical functionalization methods are disclosed in, for example, U.S. Ser. No. 10/697,974 B2 and in Zanon P R A, et al. "Profiling the Proteome-Wide Selectivity of Diverse Electrophiles". ChemRxiv; 2021. DOI: 10.26434/chemrxiv.14186561.v1. In some embodiments, once selective amino acid residues of the polypeptide analytes are functionalized, heterobifunctional linkers can be employed to connect newly installed functional groups on the polypeptide analytes with chemical moieties on the recording tag stubs.

In some embodiments, nucleic acid recording tags are attached to cellular constituents to be barcoded (such as proteins, mRNAs), and then CBP barcode information is copied from its unique genomic location to the nucleic acid recording tags using emulsion PCR or bridge amplification.

Figure 3:
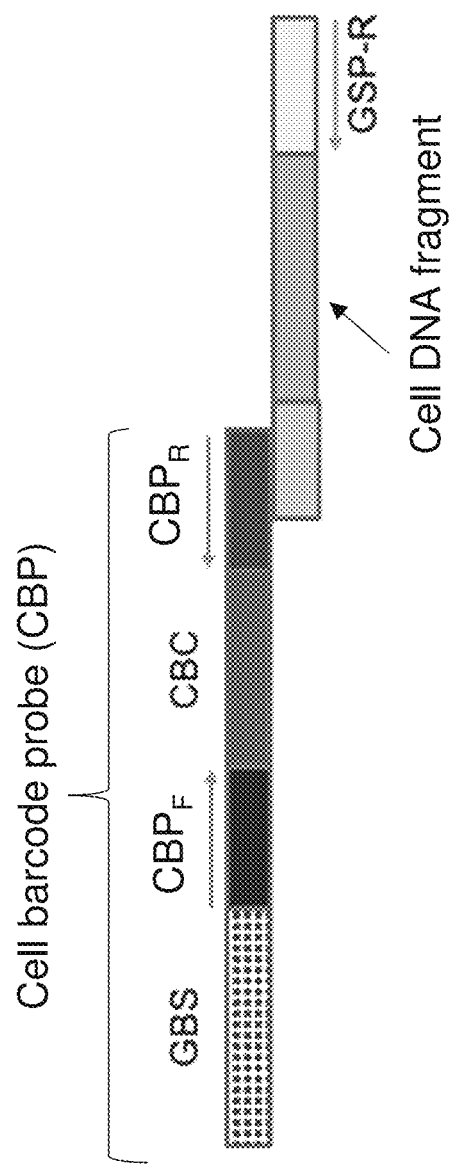
FIG. 3. Exemplary design of CBP and coupling of amplified CBP to DNA fragments (see also Example 15).

In some embodiments, a DNA recording tag stub can be attached to the 5' or 3' side of cDNA molecules by incorporating the $CBP'_F$ or $CBP_F$ into the reverse transcription primer or in template switch oligo (TSO), respectively, used in the cDNA "SMART" RT reaction (see, for example, FIG. 7A and FIG. 3). At the same time, the CBP can also be incorporated into proteins tagged with recording tag comprised of a $CBP_F$ primer.

In some embodiments of the disclosed methods, when partitioning of the cells or nuclei having CBPs into a plurality of compartments is employed, each compartment of the plurality of compartments comprises a compartment barcode configured to be attached to the macromolecules. In these embodiments, barcoding of macromolecules with unique cellular barcodes will improve macromolecule identification by following methods. For example, the cellular proteome can be partitioned into barcoded compartments. In one embodiment, this partitioning is accomplished using methods similar to those disclosed in US20190040382 A1, which is incorporated by reference in its entirety, by direct interaction of a DNA tag labeled polypeptide with the surface of a bead via hybridization to DNA compartment barcodes attached to the bead. A primer extension step transfers information from the bead-linked compartment barcode to the DNA tag on the polypeptide (see FIG. 13). In some embodiments, a protein molecule (optionally, denatured polypeptide) is labeled with DNA tags by conjugation of the DNA tags to F-amine moieties of the protein's lysine groups or indirectly via click chemistry attachment to a protein/polypeptide pre-labeled with a reactive click moiety such as alkyne (see FIG. 13). The DNA tag-labeled polypeptides are then partitioned into compartments comprising compartment tags (e.g., DNA barcodes bound to beads contained within droplets) (see FIG. 13), wherein a compartment tag contains a barcode that identifies each compartment. In one embodiment, a single protein/polypeptide molecule is co-encapsulated with a single species of DNA barcodes associated with a bead (see FIG. 13). In another embodiment, the compartment can constitute the surface of a bead with attached compartment (bead) tags similar to that described in US20190040382 A1, except as applied to proteins rather than DNA. The compartment tag can comprise a barcode (BC) sequence, a universal priming site (U1'), a UMI sequence, and a spacer sequence (Sp). Further, amplified cell barcodes can be attached to the compartment tag-labeled polypeptides via nucleic acid hybridization and primer extension. In one embodiment, concomitant with or after partitioning, the compartment tags are cleaved from the bead and hybridize to the DNA tags attached to the polypeptide, for example via the complementary U1 and U1' sequences on the DNA tag and compartment tag, respectively. For partitioning on beads, the DNA tag-labeled protein can be directly hybridized to the compartment tags on the bead surface. The spacer sequence (Sp) on compartment tags (FIG. 13) can be used for attachment of the amplified cell barcodes.

In some embodiments of the disclosed methods, cleavable linkers are used for controlled release of species from beads. Methods for generating barcodes that are releasably or reversibly attached to the beads are described, for example, in U.S. Ser. No. 10/428,326 B2, and can be utilized herein. These methods include using thermally cleavable bonds, disulfide bonds, UV sensitive bonds, other non-limiting examples of labile bonds that may be coupled to a bead, such as an a sulfone linkage (cleavable via a base), ester linkage (cleavable with an acid or a base), a vicinal diol linkage (cleavable via sodium periodate), or a glycosidic linkage (cleavable via an amylase).

The methods disclosed herein allow for generating barcoded macromolecules from single cells that can be used in a variety of downstream applications. Some examples of these applications include next generation protein analysis (NGPA) and next generation protein sequencing (NGPS) assays disclosed in US 20190145982 A1, US 20200348308 A1 and US 20220049246 A1; and various single cell sequencing techniques, such as scDNA-seq, scRNA-seq, ATAC-seq (see Examples). Barcoded macromolecules from single cells can be pooled and analyzed together to increase throughput and efficiency of the analysis. In addition, spatial information for single cells can also be preserved by using, for example, positional barcodes as a part of CBPs.

The methods disclosed herein can be used to generate barcoded macromolecules from single cells for further analysis, including detection, quantitation and/or sequencing, of a plurality of barcoded macromolecules (e.g., nucleic acids or polypeptides) simultaneously (multiplexing). Multiplexing as used herein refers to analysis of a plurality of barcoded macromolecules in the same assay. The plurality of barcoded macromolecules can be derived from the same cell or different cells. A plurality of barcoded macromolecules suitable for analysis includes 10 or more macromolecules, 100 or more macromolecules, 500 or more macromolecules, 1000 or more macromolecules, 10,000 or more macromolecules, 100,000 or more macromolecules, or more macromolecules. When 100 or more barcoded polypeptides are analyzed simultaneously in a single assay, it is referred herein as a high-throughput polypeptide analysis.

In some embodiments, 10 or more macromolecules, 100 or more macromolecules, 500 or more macromolecules, 1000 or more macromolecules, 10,000 or more macromolecules, or 100,000 or more macromolecules are barcoded by the methods disclosed herein. In some embodiments, 10 or more different macromolecules, 100 or more different macromolecules, 500 or more different macromolecules, 1000 or more different macromolecules, 10,000 or more different macromolecules, or 100,000 or more different macromolecules are barcoded by the methods disclosed herein.

In some embodiments, barcoded macromolecules produced by the methods disclosed herein are polypeptides, and these barcoded polypeptides are further analyzed by the following method: (a) contacting the barcoded polypeptides immobilized on a solid support with a plurality of binding agents capable of binding to the immobilized barcoded polypeptides; (b) following binding of a binding agent from the plurality of binding agents to an immobilized barcoded polypeptide, obtaining information regarding the binding agent, thereby analyzing the immobilized barcoded polypeptide. In some embodiments, each of the binding agents comprise a polypeptide (engineered binder) or an aptamer. In some embodiments, each of the binding agents is configured to bind specifically to a portion of the barcoded polypeptides. In some embodiments, each of the binding agents is configured to bind to one or more terminal amino acid residues of the barcoded polypeptides, or to one or more terminal amino acid residues modified with a modifying agent. In some embodiments, binding agents can be developed through directed evolution of affinity scaffolds using phage display techniques, as disclosed in U.S. patent application Ser. No. 17/539,033, filed on Nov. 30, 2021, WO 2022072560 A1, and in US patent publication US 2022/0283175 A1, incorporated herein. In some embodiments, a plurality of binding agents are a plurality of aptamers, wherein each aptamer from the plurality of aptamers exhibits binding specificity toward at least one N-terminal amino acid residue of a polypeptide immobilized on a solid support. Generation of such aptamers are disclosed in US 20210079557 A1, incorporated herein by reference.

In some specific embodiments, the barcoded polypeptides generated by the methods disclosed herein are further analyzed by the following method: (a) contacting a barcoded polypeptide covalently coupled to a solid support with a binding agent capable of binding to the polypeptide, wherein the binding agent comprises a nucleic acid coding tag comprising an encoder sequence that comprises identifying information regarding the binding agent; (b) transferring the encoder sequence or a complement thereof from the nucleic acid coding tag to the recording tag associated with the barcoded polypeptide analyte, wherein the transfer occurs through a primer extension reaction or ligation; (c) analyzing the recording tag extended after the transfer, wherein analyzing comprises a sequencing method, and obtaining the identifying information regarding the binding agent to provide information regarding the barcoded polypeptide, thereby analyzing the barcoded polypeptide.

The recited above methods for analysis of barcoded polypeptides provide opportunity for a highly parallel, high-throughput analysis of hundreds and thousands of macromolecules simultaneously in a single assay.

The methods described herein have a broad applicability, including the ability to characterize different aspects of individual cells. One example is introducing reagents to individual cells, and characterizing these cells in response to those reagents. These methods are particularly suitable for providing characterization of individual cells, cellular components, or macromolecular constituents of the cells, for research, diagnostic and other purposes. One particularly valuable application is sequencing and characterization of macromolecular constituents of a diseased cell, such as a cancer cell. Such cells can have altered morphological features, gene expression and/or metabolic properties. Exemplary diseases include cancer, inflammatory disorders, metabolic disorders.

EXEMPLARY EMBODIMENTS

Among the provided embodiments are:

1. A method for barcoding macromolecules from a sample comprising a population of cells, the method comprising the following steps:
   a. permeabilizing cells, and/or nuclei of the cells, from the population of cells of the sample;
   b. optionally making genomic DNA of the permeabilized cells and/or nuclei at least partially accessible to nucleic acid hybridization;
   c. delivering cell barcode probes to the permeabilized cells and/or nuclei of the permeabilized cells, wherein a given cell barcode probe comprises a genome binding element shared among the cell barcode probes, and a cell barcode unique for a given cell barcode probe, and wherein the genome binding element hybridizes to a region in the genomic DNA, thereby forming a nucleic acid duplex between the genome binding element and the region of the genomic DNA in the cells and/or nuclei;
   d. removing cell barcode probes that are not bound to the genomic DNA from the cells and/or nuclei, whereby no more than a defined number of copies of the cell barcode probe remain in each cell or nucleus;
   e. partitioning the cells and/or nuclei into a plurality of compartments;
   f. amplifying the cell barcodes within compartments of the plurality of compartments, thereby forming amplified cell barcodes within the compartments; and
   g. attaching the amplified cell barcodes to the macromolecules within the compartments, thereby forming barcoded macromolecules.

2. The method of embodiment 1, further comprising releasing the barcoded macromolecules from the compartments.

3. The method of embodiment 1 or embodiment 2, wherein the macromolecules being barcoded are polypeptides, mRNA molecules or cDNA molecules.

4. The method of any one of the embodiments 1-3, wherein the region in the genomic DNA is a non-repetitive region.

5. The method of embodiment 4, wherein the non-repetitive region in the genomic DNA is a non-coding region or a differentially methylated region.

6. The method of any one of the embodiments 1-5, wherein the genome binding element of each cell barcode probe comprises a PCR priming site adjacent to the cell barcode that is used to amplify the cell barcode at step (f).

7. The method of any one of the embodiments 1-6, wherein the defined number of copies is one copy.

8. The method of any one of the embodiments 1-6, wherein the defined number of copies is two copies.

9. The method of any one of the embodiments 1-8, wherein the sample is a spatial sample, and wherein the sample is dissociated into a plurality of cells at step (e).

10. The method of embodiment 9, wherein each of the cell barcode probes further comprise a positional barcode different for at least some of the cell barcode probes.

11. The method of embodiment 9, wherein the cell barcode probes are delivered at step (c) from a spatially ordered array.

12. The method of embodiment 9, further comprising, after step (b), (i) delivering a plurality of positional probes to the permeabilized cells and/or nuclei, wherein a given positional probe comprises a common targeting element configured to be attached to the macromolecules and a positional barcode different for each positional probes; and (ii) attaching positional probes from the plurality of positional probes to the macromolecules.

13. The method of embodiment 12, wherein each of the amplified cell barcodes comprises a common region that is configured to hybridize to a region in the positional probes; and the method further comprises a step of performing a primer extension reaction to transfer the amplified cell barcodes to the positional probes attached to the macromolecules.

14. The method of embodiment 12, wherein the plurality of positional probes is delivered from a spatially ordered array.

15. The method of any one of the embodiments 1-9, wherein each compartment of the plurality of compartments comprises a compartment barcode configured to be attached to the macromolecules.

16. The method of any one of the embodiments 1-15, wherein during partitioning the cells and/or nuclei into the plurality of compartments at step (e), on average no more than one cell or nucleus comprising a cell barcode probe is comprised within a single compartment.

17. The method of any one of the embodiments 1-16, wherein attaching the amplified cell barcodes to the macromolecules within the compartments comprises: i) covalently attaching nucleic acid recording tags to the macromolecules or macromolecule derivatives of the cell; and (ii) attaching the amplified cell barcodes to the nucleic acid recording tags.

18. A method for barcoding macromolecules from a sample comprising a population of cells, the method comprising the following steps:
a. permeabilizing cells, and/or nuclei of the cells, from the population of cells of the sample;
b. delivering reactive primers that are configured to be covalently attached to components of the permeabilized cells and/or nuclei, thereby creating a plurality of attached primers;
c. optionally making genomic DNA of the permeabilized cells and/or nuclei at least partially accessible to nucleic acid hybridization;
d. delivering cell barcode probes to the permeabilized cells and/or nuclei of the permeabilized cells, wherein a given cell barcode probe comprises a genome binding element shared among the permeabilized cells and/or nuclei, and a cell barcode unique for each cell or nucleus, and wherein the genome binding element hybridizes to a region in the genomic DNA, thereby forming a nucleic acid duplex between the genome binding element and the region of the genomic DNA in the cells and/or nuclei;
e. removing cell barcode probes that are not bound to the genomic DNA from the cells and/or nuclei, whereby no more than a defined number of copies of the cell barcode probe remain in each cell or nucleus;
f. amplifying the cell barcodes using the plurality of attached primers, thereby forming amplified cell barcodes within the compartments; and
g. attaching the amplified cell barcodes to the macromolecules within cells, thereby forming barcoded macromolecules.

19. The method of embodiment 18, wherein amplifying the cell barcodes at step (f) comprises providing conditions for hybridization between the cell barcode probes and the plurality of attached primers.

20. The method of embodiment 18 or embodiment 19, wherein the defined number of copies is one copy.

21. The method of any one of the embodiments 18-20, wherein the macromolecules being barcoded are polypeptides, mRNA molecules or cDNA molecules.

22. The method of any one of the embodiments 18-21, wherein the region in the genomic DNA is a non-repetitive region.

23. The method of embodiment 22, wherein the non-repetitive region in the genomic DNA is a non-coding region.

24. The method of any one of the embodiments 18-23, wherein each of the cell barcode probes further comprises a positional barcode different for at least some of the cell barcode probes.

25. The method of any one of the embodiments 18-24, wherein the cell barcode probes are delivered at step (d) from a spatially ordered array.

26. A method for barcoding macromolecules from a sample comprising a population of cells, the method comprising the following steps:
a. permeabilizing cells, and/or nuclei of the cells, from the population of cells of the sample;
b. delivering a specific genomic DNA-binding carrier comprising a cell barcode probe to the permeabilized cells and/or nuclei, wherein a given cell barcode probe comprises a cell barcode unique for each cell or nucleus, and a priming site, and wherein the specific genomic DNA-binding carrier specifically binds to a region in the genomic DNA of the cells and/or nuclei;
c. removing specific genomic DNA-binding carriers that are not bound to the genomic DNA from the cells and/or nuclei, whereby no more than a defined number of copies of the cell barcode probe remain in each cell or nucleus;
d. amplifying the cell barcodes that were not removed from the cells and/or nuclei at step (c), thereby forming amplified cell barcodes; and
e. attaching the amplified cell barcodes to the macromolecules, thereby forming barcoded macromolecules.

27. The method of embodiment 26, wherein amplifying the cell barcodes comprises the following steps:
(i) partitioning the cells and/or nuclei into a plurality of compartments; and
(ii) amplifying the cell barcodes within compartments of the plurality of compartments, thereby forming amplified cell barcodes within the compartments.

In an alternative embodiment, amplifying the cell barcodes comprises: a) delivering reactive primers that are configured to be covalently attached to components of the permeabilized cells, thereby creating a plurality of attached primers; and b) amplifying the cell barcodes using the plurality of attached primers, thereby forming amplified cell barcodes.

28. The method of embodiment 26, wherein the specific genomic DNA-binding carrier comprises a catalytically inactive Cas nuclease, a TALE protein or a zinc-finger protein.

29. The method of any one of the embodiments 26-28, wherein the cell barcode probe is integrated in the genomic DNA of the cells and/or nuclei at step (b).

30. The method of any one of the embodiments 27-29, wherein during partitioning the cells and/or nuclei into the plurality of compartments, on average no more than one cell or nucleus comprising a cell barcode probe is comprised within a single compartment.

31. The method of embodiment 26 or embodiment 28, wherein at step (d) the cell barcodes are amplified in situ within cells and/or nuclei, and without partitioning the cells and/or nuclei into the plurality of compartments.

32. The method of any one of the embodiments 26-31, wherein the defined number of copies is one copy.

33. The method of any one of the embodiments 27-30, further comprising releasing the barcoded macromolecules from the compartments.

34. The method of any one of the embodiments 26-33, wherein the macromolecules being barcoded are polypeptides, mRNA molecules or cDNA molecules.

35. The method of any one of the embodiments 26-34, wherein the region in the genomic DNA is a non-repetitive region.

36. The method of embodiment 35, wherein the non-repetitive region in the genomic DNA is a non-coding region.

37. The method of any one of the embodiments 26-36, wherein the genome binding element of each cell barcode probe comprises a PCR priming site adjacent to the cell barcode that is used to amplify the cell barcode at step (d).

38. The method of any one of the embodiments 26-37, wherein the sample is a spatial sample.

39. The method of any one of the embodiments 26-38, wherein each of the cell barcode probes further comprises a positional barcode different for at least some of the cell barcode probes.

40. The method of any one of the embodiments 27-30, wherein each compartment of the plurality of compartments comprises a compartment barcode configured to be attached to the macromolecules.

41. The method of any one of the embodiments 27-30, wherein attaching the amplified cell barcodes to the macromolecules within the compartments comprises: i) covalently attaching nucleic acid recording tags to the macromolecules or macromolecule derivatives of the cell; and (ii) attaching the amplified cell barcodes to the nucleic acid recording tags.

EXAMPLES

The following examples are offered to illustrate but not to limit the methods, compositions, and uses provided herein. Certain aspects of the present invention, including, but not limited to, methods of generating barcodes, methods of making nucleotide-polypeptide conjugates, embodiments for the Proteocode™ polypeptide sequencing assay, methods for attachment of nucleotide-polypeptide conjugates to a solid support were disclosed in earlier published application US 2019/0145982 A1, US 2020/0348308 A1, US 2020/0348307 A1, US 2021/0208150 A1, U.S. Ser. No. 11/427,814 B2, US 2022/0049246 A1, the contents of which are incorporated herein by reference in its entirety.

In the barcoding methods disclosed above and in Examples below, nuclei can be isolated from cells and utilized instead of cells; thus, cell barcode probes can be delivered for association or hybridization with a specific region (or regions) of gDNA to the permeabilized cells and/or permeabilized nuclei of the cells. In some embodiments, standard buffers to stabilize the permeabilized nuclei during steps of CBP association/hybridization, CBP amplification, compartmentalization can be employed.

Example 1. Exemplary Samples and Cell Types to be Used in the Barcoding Methods Disclosed Herein Barcoding methods applied during single cell analysis can be employed using various cell and tissue types both adherent cells and suspension cells. Cells can be barcoded in an adherent state and later be dissociated and optionally enriched (e.g., by magnetic-activated cell sorting (MACS), flow sorting, etc.) prior to downstream processing in emulsions. Examples of samples and cell types include: 1) Cultured adherent human cell lines (such as A549, SKBR3) or suspension cells (such as K562, Jurkat); 2) cultured mouse cell lines (such as NIH3T3); 3) adherent or suspension blood cells (PMBCs, T-cells, B-cells); 4) cell suspension from a dissociated tissue sample such as cells prepared from fixed tissue using vivoPHIX™ Dissociation Protocol (RNAssist); 4) isolated cell nuclei; 5) frozen tissue sections; 6) Formalin-Fixed Paraffin-Embedded (FFPE) tissue sections.

Example 2. Fixation and Permeabilization of Cells Before Delivering Cell Barcode Probes (CBPs) to the Permeabilized Cells Using a Formaldehyde-Based Protocol Formaldehyde cross-links macromolecules within cells and tissues for further analysis. Cells in suspension are washed with phosphate buffered saline (PBS) (pH=7.4) three times, and fixed for 10 min at room temperature (RT) in paraformaldehyde (1-4% in PBS). After fixation, cells are washed once with PBS supplemented with 10 mM glycine (PFA quenching), and then washed 2 times with PBS, 5 min each at RT. The amount of paraformaldehyde is optimized for each sample type to provide adequate fixation while minimizing RNA damaging as assessed by evaluating the RNA Integrity Number (RIN) based on comparing 28S to 18S rRNA using known protocols.

For permeabilization, fixed cells are resuspended in 0.5% Triton X-100 in PBS and incubated at RT for 5 min. After rinsing with PBS, cells are ready for hybridization. Alternatively, fixed and permeabilized cells can be stored at 4° C. for one day. Other detergents (such as NP40, Tween-20), or alcohol (such as methanol) can also be used for permeabilization.

Example 3. Fixation and Permeabilization of Cells Before Delivering CBPs to the Permeabilized Cells, Using RNA Preserving Protocols: A DSP-Based Protocol or an ACME-Based Protocol Dithio-bis(succinimidyl propionate) (DSP) is a reversible cross-linker of free amine groups that has previously been shown to preserve tissue integrity for histology (Attar, M., et al. (2018) A practical solution for preserving single cells for RNA sequencing. Sci Rep, 8, 2151). DSP stock solution is prepared by dissolving DSP in anhydrous DMSO to 50 mg/mL and stored at −80° C. The DSP stock solution was diluted to working concentration (1 mg/mL) with PBS immediately before used by adding 490 uL PBS to 10 uL DBS stock dropwise while vortexing. DSP working solution is filtered using 30 um filter (Miltenyi, Pre-Separation Filters; 30 μm) before use.

Cells or nuclei are centrifuged for 5 min at 200-500 g depending on cell/nuclei size and density, and washed twice with 200 uL 1×PBS. After the final wash, the cell pellet is resuspended gently in 200 uL DSP solution and incubated at room temperature for 30 min. The reaction is quenched by adding 4.1 uL of 1M Tris-HCl, pH=7.5. After DSP fixation, the cells are permeabilized as described in Example 2.

In addition to DSP, other bifunctional crosslinkers, such as $BS(PEG)_5$ (PEGylated bis(sulfosuccinimidyl)suberate) (Thermo Scientific, A35396), can also be used for cell fixation. Reversible cross-linkers, such as DSP, are useful for preserving RNA integrity by enabling reversal of disulfide crosslinks using reducing agents like dithiothreitol (DTT) or tris(2-carboxyethyl)phosphine (TCEP) prior to RNA reverse transcription.

As an alternate to formaldehyde fixation or reversible cross-linker fixation, an acetic acid/methanol (ACME) protocol can be employed, which better preserves RNA integrity than formaldehyde-based methods (Garcia-Castro, et al., 2021. "ACME Dissociation: A Versatile Cell Fixation-Dissociation Method for Single-Cell Transcriptomics." Genome Biology 22 (1): 89). Namely, cells are fixed and permeabilized by incubating with and ACME solution devoid of methanol (8.5 ml of ACME w/o methanol is comprised of 6.5 ml of 1×PBS buffer supplemented with 1% BSA, 1 ml glycerol, 1 ml of acetic acid, and 100 ul of 7.5% NAC). The cells are incubated for 20 min. at room temperature on a shaker at 40 rpm. After shaking, methanol is added to the cells in ACME buffer to a final concentration of 15% methanol ACME buffer. Methanol was added after initial acid treatment to allow partial fixation in acetic acid prior to permeabilization. After fixation in ACME solution, the cells were centrifuged at 1000 g for 5 min (4° C.) to remove the ACME solution. Cells were resuspended in 1×PBS buffer supplemented with 1% BSA for further processing.

Example 4. Fixation and Permeabilization of Cells Before Delivering CBPs to the Permeabilized Cells, a RNA Preservation Protocol In some applications, RNA integrity needs to be preserved. For this purpose, a fixation protocol based on methanol (MeOH) and ammonium sulfate solutions that precipitates proteins, inhibits enzymatic activity can be used (Katzenelenbogen, Y., et al. (2020) Coupled scRNA-Seq and Intracellular Protein Activity Reveal an Immunosuppressive Role of TREM2 in Cancer. Cell, 182, 872-885 e819). Cells ($1\times10^6$-$5\times10^6$) are resuspended in 100 uL of cold PBS supplemented with 0.4 U/uL RNasin Plus RNase Inhibitor (Promega). To avoid cell clumping, 900 uL of methanol (pre-chilled to −20° C.) are added dropwise, while gently mixing to achieve a final concentration of 90% methanol in PBS. Cells are fixed in methanol for 10 minutes on ice in the dark.

Fixed cells are pelleted at 900 g for 3 minutes right after fixation. Methanol-PBS solution is completely discarded. Cell pellet is washed (not resuspended) twice with ice-cold PBS supplemented with 0.4 U/uL RNasin Plus RNase Inhibitor without breaking the pellet, for complete removal of methanol leftovers. Cell pellet is resuspended in 100 uL of enzyme blocking buffer containing ammonium sulfate (Thermo Fisher) solution (0.05 M EDTA (Sigma), 0.8 U/uL RNasin Plus RNase Inhibitor, pH=5.2) and kept on ice for 10 minutes in the dark.

Example 5. In Situ Hybridization (ISH) of CBPs Using Heat and Formamide Denaturation In situ hybridization of CBPs is performed using an in situ hybridization protocol modified from Kapoor et al. (Kapoor and Telford, 2004). Cells are fixed and permeabilized according to any one of Examples 2-4, followed by washing the cells with 1×PBS supplemented with 0.1% bovine serum albumin (BSA). After washing, approximately $10^6$ cells are resuspended in 300 ul of hybridization buffer (70% Formamide, 2×SSC (saline-sodium citrate buffer; Ambion, AM9763), 1% BSA) supplemented with a cellular barcode probe (CBP) at 50-300 nM concentration (e.g., CBP_Ch11-344380, SEQ ID NO: 1). The cellular hybridization mix is incubated at 80° C. for 10 min, mixed, and then incubated 2 hours or overnight at 37° C. After the CBP hybridization, excess of the CBP is removed by washing cells three times in 1 ml wash buffer (2×SSC) at 40° C. for 10 min. Cells are spun down at 400 g between wash steps. After the final wash, cells are resuspended in 1×PBS buffer. A similar protocol can be applied to fixed/permeabilized tissues on slides.

Exemplar gDNA FISH Probe (iFISH; from Gelali, et al. 2019. "IFISH Is a Publicly Available Resource Enabling Versatile DNA FISH to Study Genome Architecture." Nature Communications 10 (1): 1636).

An exemplary gDNA FISH probe from the iFISH database is a follows: (a) CBP_Ch11-344380; TGGCCAGGAGGA-GACTCTTCCAGGTCTCCCTTCTGACACC (SEQ ID NO: 1). Target gDNA sequence: chr11, from 344380 to 344419. In a preferred embodiment, the GBS portion of the CBP probe has 35-50 bases of homology with single copy genomic loci, preferably a non-transcribed and non-repetitive region.

Another example of an iFISH probe is one containing a PmeI site: (b) Chr7 CBP: AAACCTTGCCAACCAT-GAGTTTCTGGGACTGACGGTGATG (SEQ ID NO: 2). Target gDNA sequence: chr7, from 63/367,821 to 63/367, 861.

Digestion by PmeI enables strand-displacement and optional ligation-based genomic tagging.

Example 6. Adaption of MERFISH for CBP Labeling of gDNA Loci

Using a protocol adapted from Su et al. (Su, et al., 2020. "Genome-Scale Imaging of the 3D Organization and Transcriptional Activity of Chromatin." Cell 182 (6): 1641-1659.e26), cells mounted on slides are fixed with 4% paraformaldehyde (PFA) in PBS for 10 minutes at room temperature and washed 3 times in 1×PBS buffer. Cells are then permeabilized by incubating with 0.5% v/v Triton-X100 (Sigma-Aldrich, T8787) in PBS for 10 minutes at room temperature followed by 0.1 M hydrochloric acid (HCl) treatment for 5 minutes at room temperature. The cells are then washed again 3 times in 1×PBS buffer. Following washing, cells are incubated in pre-hybridization buffer, consisting of 2× saline-sodium citrate buffer (SSC; Ambion, AM9763), 50% formamide (Ambion, AM9342) and 0.1% of Tween-20 (Sigma-Aldrich, P4916) for 30 minutes. Next, the cells are incubated in hybridization buffer (2×SSC, 50% formamide, 10% dextran sulfate (Sigma-Aldrich, D8906) containing a mixture of CBPs at ~20 nM total concentration with or without 10 µg Human Cot-1 DNA (ThermoFisher, 15279011). The cells are incubated at −90° C. for 3 minutes and incubated at 47° C. in a humidified chamber for at least 16 hours. After this incubation step with CBPs, they are washed in 2×SSC and 40% formamide for 30 minutes and post-fixed with 4% PFA in 2×SSC for 10 minutes at room temperature to lock the CBPs in place. The cells are subsequently washed 3 times in PBS buffer. An alternate hybridization buffer using ethylene carbonate in lieu of formamide can also employed: this alternate hybridization buffer is composed of 2×SSC, 10% (vol/vol) ethylene carbonate (Sigma-Aldrich, E26258), 0.1% (vol/vol) murine RNase inhibitor (NEB), 0.5% (vol/vol) Triton X-100 and 0.4% (vol/vol) Tween-20 in nuclease-free water. The pre and post hybridization washes employ a wash buffer comprised of 2×SSC, 10% (vol/vol) ethylene carbonate, and 0.5% Tween-20 in nuclease-free water.

Example 7. ISH of Sample Slides with PNA-DNA Chimeras

A chimeric CBP PNA-DNA probe is designed wherein the GBS portion of the CBP is comprised of PNA and the amplification and barcode portions are comprised of DNA. Slides are fixed in 4% paraformaldehyde in PBS for 10 min at room temperature, washed in 1×PBS, are then dehydrated in 70%, 85%, and 100% ethanol for two minutes each in an ice water bath. They are then placed in a 2×SSC 70% Formamide solution at 80° C. for 2 minutes, followed by an ethanol wash. The CBP PNA-DNA chimeric probe is hybridized to the denatured gDNA in 60% formamide Hyb buffer (60% of Formamide, 20 mM of Tris-HCl, 200 nM of CBP probe (GBS portion is ~16-20 bases)). This solution is denatured at 85° C. for 5 minutes, then cooled down to 37° C. before adding 30 µL to each slide. The probes are allowed to hybridize overnight at 37° C., and the slides are then washed in a high stringency condition comprised of washing with 2×SSC 70% Formamide solution for 15 minutes at 37° C., followed by post-hybridization washing under in 2×SSC for 4×5 min at 42° C. (Genet, M. D., et al., 2013. Molecular Cytogenetics 6 (1): 42).

Alternatively, fast hybridization buffer containing ethylene carbonate or similar polar aprotic solvents can be employed with the chimeric PNA-DNA CBP probe (Matthiesen and Hansen. 2012. PloS One 7 (7): e40675). The chimeric CBP is hybridized directly to the slide without prior denaturation of the gDNA. A fast hybridization buffer is composed of 15% ethylene carbonate, 20 mM of Tris-HCl, 200 nM of the chimeric CBP probe). This solution is denatured at 85° C. for 5 minutes, then cooled down to 37° C. before adding 30 µL to each slide. The CBPs are allowed to hybridize overnight at 37° C., and then the slides are washed under high stringency condition comprise of washes in 2×SSC and 15% ethylene carbonate solution for 15 minutes at 37° C., followed by post-hybridization washing in 2×SSC and 10% ethylene carbonate for 3×5 min at 42° C. Ethylene carbonate can also be used for fast hybridization of standard DNA-based CBPs as well.

Example 8. In Situ Hybridization of CBPs Using Restriction Endonuclease (RE) or Targeted CRISPR/Cas9 Digestion and ExoIII ssDNA Generation Using an in situ hybridization method modified from the protocol described by Larsson et al (Larsson, et al., 2004. "In Situ Genotyping Individual DNA Molecules by Target-Primed Rolling-Circle Amplification of Padlock Probes." Nature Methods 1 (3): 227-32), cells are prepared for hybridization with washing in 1×PBS. To initiate restriction digestion, a reaction mix of 1× rCutSmart™ Buffer (50 mM Potassium Acetate, 20 mM Tris-acetate 10 mM Magnesium Acetate, 100 µg/ml Recombinant Albumin (pH 7.9 at 25° C.)) supplemented with 0.5 U/ml MScI (NEB) or PmeI (NEB) is incubated for 37° C. for 30 min with the fixed/permeabilized cellular sample. The CBP is designed adjacent to the termini created in the gDNA by the described restriction enzyme digestion or Targeted Cas9 digestion as described below in Example 9. After endonuclease digestion, the cells are washed with 1× NEB Buffer 1 (10 mM Bis-Tris-Propane-HCl, 10 mM, MgCl2, 1 mM DTT, pH 7 at 25° C.). Next, the gDNA is made single stranded by resuspending the cells in 1× NEB Buffer 1 supplemented with 0.2 mg/ml BSA and 10% glycerol and incubating with 0.2 U/ml exonuclease III at 37° C. for 15 min. After incubation the slides were rinsed in buffer 1×PBS supplemented with 1 mM EDTA and 0.1% BSA.

After making gDNA regions single stranded within the cells, CBPs are hybridized to the ssDNA within the fixed/permeabilized cells by incubating with 50-300 nM probe concentration in hybridization buffer (30-50% Formamide, 2×SSC, 1% BSA) at 37-50° C. for 1 hr. After probe hybridization, excess of probe is removed by washing cells three times in 1 ml wash buffer (30-50% formamide in 2×SSC) at 37-50° C. for 5 min. Cells are spun down at 400 g between wash steps. Additional more stringent (high formamide and temperature) wash steps can be used as necessary to reduce background from unbound CBPs. After the final wash, cells are resuspended in 1×PBS buffer.

Example 9. In Situ Hybridization and Ligation or Gap-Fill Ligation of Padlock CBPs After linearization of and ssDNA formation within the genomic DNA, the padlock CBP is annealed and then circularized via ligation. Namely, the padlock probes are annealed to the fixed and permeabilized cells 100 nM probe concentration in 6×SSC buffer supplemented with 20% formamide at 37° C. for 4 hrs; after hybridization and washing twice with ligation buffer, the padlock probe arms are ligated by incubation with 0.1 U/ml T4 DNA ligase in ligation buffer (10 mM Tris-acetate pH 7.5, 10 mM magnesium acetate, 150 mM NaCl, 1 mM ATP, 0.2 mg/ml BSA) at 37° C. for 30 min. After ligation, the cells are washed in high formamide buffer to remove non-specifically bound padlock CBPs or unligated CBPs. Circularized CBP probe forms a very stable topological interlocking unit with the genomic DNA. Alternatively, padlock probes designed with an intervening gap between the two annealed ends can be gap-filled and ligated by a cocktail of non-strand displacing polymerase and ligase. Namely, the annealed padlock probe can be gap-filled and ligated using an enzyme mix containing 0.2 U/µl Phusion High-Fidelity DNA Polymerase (Thermo Fisher Scientific), and 0.5 U/µl Ampligase (Epicentre) in 1× Ampligase buffer (20 mM Tris-HCl, 25 mM KCl, 10 mM MgCl$_2$, 0.5 mM NAD, 0.01% Triton X-100) supplemented with 50 µM dNTP, and an additional 25 mM KCl. The reactions are incubated at 30 min at 37° C. followed by 45 min at 45° C. with a final 2× wash in PBST buffer.

Example 10. CRISPR-dCas9 In Situ Cellular Barcode Tagging of gDNA

A modified protocol from Ishii et al. using RGEN-ISL in situ FISH technique is used to label genomic DNA with CBPs (Ishii, et al., 2019. "RNA-Guided Endonuclease—in Situ Labelling (RGEN-ISL): A Fast CRISPR/Cas9-Based Method to Label Genomic Sequences in Various Species." The New Phytologist 222 (3): 1652-61). Namely, single copy genomic regions are targeted with a CRISPR-Cas9 system using either a single gRNA construct or bipartite gRNA construct. The bipartite gRNA is comprised of crRNA and tracrRNA that annealed prior to CRISPR-Cas9 loading (such as Alt-R® CRISPR-Cas9, Integrated DNA Technologies). Alternatively, a single gRNA can be employed; the advantage of the bipartite construct is that the tracrRNA portion can be appended with functional RNA elements that otherwise may make the gRNA tool long as a contiguous RNA construct.

In the bipartite system, the gRNA is assembled by annealing crRNA with tracerRNA as follows: a mix of 1 µL 100 µM crRNA+1 µL 100 µM CBP-labeled tracrRNA, and 8 µL annealing buffer is denatured for 5 min at 95° C. and slow cooled to room temperature to allow annealing between the crRNA with tracerRNA. The dCas9 ribonucleoprotein (RNP) complex is assembled by combining 1 µL 10 µM gRNA, 1 µL 6.25 µM dCas9 proteins (D10A and H840A; Novateinbio, PR-137213), 10 µL 10× Cas9 buffer (200 mM Hepes pH 7.5, 1 M KCl, 50 mM $MgCl_2$, 50% (v/v) glycerol, 10% BSA, and 1% Tween-20), 10 µL 10 mM DTT, and 80 µL double distilled water. The mix is incubated at 26° C. for 10 min, and stored at 4° C. For each slide processed, 100 µL of 1× Cas9 buffer/1 mM DTT is added and incubated for 2 min at room temperature. The buffer is removed and 25 µL RNP complex per slide is applied. The slides are covered with parafilm and kept in a humid chamber at 26° C. for 2-4 h. After incubation, the slides are washed in ice-cold 1×PBS for 5 min. To prevent the dissociation of the RNP complex, an optional post-fixation step is performed with 4% formaldehyde in 1×PBS for 5 min on ice. Finally, the slides are washed with 1×PBS for 5 min on ice and dehydrated in ethanol (70, 90, and 96% of ethanol; 2 min each) at room temperature.

Example 11. In Vitro Prime Editing of Fixed/Permeabilized Cells Inserting CBPs into gDNA In a protocol adapted from Anzalone et al., a Prime Editing system is constructed by assembling a pegRNA with a CRISPR nCas9 (H840A) nickase fused via its C-terminus to an M-MLV RT variant reverse transcriptase (RT) (Anzalone, et al. 2019. "Search-and-Replace Genome Editing without Double-Strand Breaks or Donor DNA." Nature 576 (7785): 149-57). The nCas9-RT ribonucleoprotein (RNP) complex is assembled by combining 1 µL 10 µM pegRNA, 1 µL 6.25 µM nCas9-RT protein, 1 µL of 0.5 mg/ml FEN1 (MCLABS), and 20 µL 5× M-MLV RT buffer (250 mM Tris-Cl pH 8.3, 275 mM KCl, 15 mM $MgCl_2$, 50 mM DTT, 25% (v/v) glycerol, 5% BSA, and 0.5% Tween-20), 10 µL of 10 mM dNTPs, and 70 µL ddH2O. The mix is incubated at 37° C. for 5 min, and stored at 4° C. For each slide processed, 100 µL of 1×M-MLV RT buffer mix is added and incubated for 2 min at room temperature. The buffer is removed and 25 µL nCas9-RT RNP mix is applied per slide. The slides are covered with parafilm and kept in a humid chamber at 37° C. for 2-4 h. After incubation, the slides are washed with 1×PBS for 5 min at room temperature.

Example 12. MeFISH Technique to Attach a Single Copy of CBP to Methylated Genomic DNA Using a protocol adapted from Shiura et al. (Shiura, et al., 2014. "Whole-Mount MeFISH: A Novel Technique for Simultaneous Visualization of Specific DNA Methylation and Protein/RNA Expression." PloS One 9 (4): e95750), permeabilized cells are washed with 2×SSCT (2×SSC with 0.1% Triton X-100) for 10 min, and washed twice with 2×SSCT and 50% formamide for 10 min. After washing the cells with hybridization buffer (2×SSCT, 50% formamide, and 2 mg/ml BSA) for 20 min, the cells are placed in a 10 nM solution dipyridyl-labeled CBP probe in hybridization buffer. The genomic DNA is denatured by heating at 98° C. for 5 min, and hybridization is performed for ~16 hrs at room temperature. The cells are washed three times with 2×SSCT at room temperature for 5 min. The CBP probe comprised of a GBS sequence containing a bipyridine-attached adenine derivative, designed to be opposite of a methylated cytosine residue, is cross-linked to methylated cytosines by incubating in freshly made cross-link solution (25 mM K2OsO4N2H2O, 100 mM Tris-HCl (pH 7.4), 1 mM EDTA, 2 M NaCl, and 0.1% Triton X-100) at 30° C. for 10 min. Non-cross-linked probes are removed by denaturation in 90% formamide/2×SSCT followed by washing in PBST (1× Phosphate-Buffered Saline, 0.1% Tween-20).

Example 13. Partitioning the Cells Having Defined Copy Numbers of CBPs into a Plurality of Compartments, Flow Cytometry-Based Protocol Cells are partitioned into 96-well or 384-well plates using a FACS instrument (Cao, J., et al. (2017) Comprehensive single cell transcriptional profiling of a multicellular organism. Science, 357, 661-667). First, cells or nuclei are stained with 4',6-diamidino-2-phenylindole (DAPI, Invitrogen) by adding 1.5 uL of 0.1 mg/mL DAPI solution to 600 uL cells that are resuspended in 1×PBS with 0.5% BSA. Other DNA staining dyes, such as propidium iodide (PI) or SYBR Green, can also be used instead of DAPI. After staining, the cells are sorted with FACSAria III cell sorter (BD Biosciences) using the optimized parameters of FSC, SSC, DAPI channels. One DAPI-positive cell/nucleus is placed in each well of 96-well or 384-well plates. After sorting single cells, 10 uL of PCR reaction mix that contains 1× Phusion master mix (Thermo Scientific), 1 mg/mL BSA, and PCR primers are added to each well.

Example 14. Partitioning the Cells Having Defined Copy Numbers of CBPs into a Plurality of Compartments, Droplet-Based Methods Single cells, together with the aqueous phase containing reagents needed for the following amplification reaction, are encapsulated into droplets using shaking or repetitive pipetting techniques (Redin, D., et al., (2017) Droplet Barcode Sequencing for targeted linked-read haplotyping of single DNA molecules. Nucleic Acids Res, 45, e125). The aqueous phase of each assay reaction is consisted of 50 uL PCR reagents containing 1× Phusion master mix (Thermo Scientific), 1 mg/mL BSA, and PCR primers. Single cells, together with hybridized barcode template, are also added to the aqueous phase. The numbers of cells are adjusted based on the anticipated cell doublet rate. The aqueous phase is then added on top of 100 uL HFE-7500 oil with 5% (w/v) 008-Flourosurfactant (Ran Biotechnologies, MA, USA), and the two phases are emulsified by shaking for 8 min at 15 Hz in a Qubit™ tube (Life Technologies), using a Tissuelyser instrument (Qiagen, MD, USA).

Alternatively, repetitive pipetting can be used to generate droplets. After adding 50 uL aqueous phase to 100 uL oil, a 200 uL pipette setting at 120 uL, is used to mix the aqueous phase and oil. After 40-60 times of repetitive pipetting, the droplets with encapsulated cells are ready for PCR reaction.

Commercial droplet generating systems, such as 10× Genomics Chromium, Mission Bio Tapestri, or Dolomite Bio Nadia can also be used to encapsulate cells together with PCR reaction reagents in droplets. When using these commercial droplet generation systems, cell barcode beads are not needed. Instead, CBPs in the cells will be encapsulated in the droplets together with the PCR reagents, followed by in-droplet amplification of CBPs, followed by coupling of CBPs to the desired macromolecules (such as cell DNA fragments, polypeptides or mRNA molecules).

In another method, emulsion PCR droplets are created using a bead-templated or microparticle-templated emulsion ("dropsicles") process as described in Hatori et al. and Wu et al. (Hatori, et al., 2018. "Particle-Templated Emulsification for Microfluidics-Free Digital Biology." *Analytical Chemistry* 90 (16): 9813-20), (Wu, et al., 2020. "Monodisperse Drops Templated by 3D-Structured Microparticles." *Science Advances* 6 (45): eabb9023), and in US patent application US20200261879 A1. In US20200261879 A1, the use of bead-templated emulsion in combination with cell encapsulation is described. The beads are in at least ten-fold excess over cells to ensure single cell loading per droplet. The bead size is larger than the average cell size to favor compartmentalization of cells along with beads in a compartment where the bead serves primarily a templating vehicle. These droplets can be loaded with PCR reagents to enable an ePCR reaction.

Alternatively, emulsion PCR droplets are created directly from fixed cells, and particularly fixed cells that have been intracell hydrogelated in which the interior of the cell has been filled with cross-linked hydrogel polymer (Lin, et al., 2019. "Intracellular Hydrogelation Preserves Fluid and Functional Cell Membrane Interfaces for Biological Interactions." *Nature Communications* 10 (1): 1057). The elastic modulus of the cell renders is sufficiently robust to enable templated emulsions directly from the cell itself. Once in the droplet, the hydrogel matrix can be dissociated by using a cleavable crosslinker such as a disulfide containing crosslinker. In brief, using a protocol adapted from Lin et al., hydrogelated cells are generated post-genomic CBP labeling and rTagging process, by incubating with cells with a gelation mix comprising a 1 wt % of the photo crosslinker 2-hydroxy-4'-(2-hydroxyethoxy)-2-methylpropiophenone (Irgacure D-2959; Sigma-Aldrich), and the dissolvable polymer poly(ethylene glycol)-SS-diacrylate (the PEGSSDA reagent; Advanced Biomatrix, CA) ranging from 4 to 40 wt % in 10 mM phosphate buffer. Cells in suspension is pelleted at 200 g and resuspended in designated gelation mix. For cross-linking adherent cells, cells grown on a tissue culture plate or slides are washed with PBS and immersed in the designated gelation mix. The suspension cells are pelleted at 200×g and resuspended in PBS on a tissue culture plate, whereas adherent cells are washed with PBS twice. The tissue culture plates are then placed in an ice bath, and the cells are crosslinked with 365 nm UV wavelength for 10 min using a UV lamp (UVP UVLMS-38 EL Series) placed 2 in. above the tissue culture plate. The resulting cells are washed twice in PBS for further processing.

After templated emulsion generation, the hydrogel is dissolved by incubation in 1 mM DTT at 30° C. for 10 min. After cell hydrogelation, 100 ul of hydrogelated cells (per volume) are combined with 200 ul 2× PCR Master Mix, 18 ul of 1 uM $CBP_F$ and 18 ul 10 uM $CBP_R$ primer, 8 ul 10% TX-100, and 38 ul water. The mix is incubated at room temperature for 15 min under gentle agitation (10 rpm) using a tube rotator to ensure homogenous distribution of the PCR components within the cell. The disperse phase is centrifuged at 600 g for 1 min and the supernatant is removed. A volume of 200 µL 2% fluorosurfactant in HFE-7500 oil (008-Fluoro-surfactant, RAN Biotechnologies) is added to the tube as the insoluble continuous phase for emulsification. The hydrogelated cell pellet is dislodged by pipetting or tapping/flicking the tube. The sample is then vortexed at 2000-3000 rpm for 30 sec. The emulsion is allowed to settle for 1 min. A volume of 100 µL of the bottom oil phase is removed and replaced with an equal volume of fresh 2% fluorosurfactant in HFE oil. The tube is gently inverted several times to mix. This step is repeated 3-5× or until small satellite droplets have been removed. After emulsification, the hydrogel within the cells is dissolved by exchanging the 2% fluorosurfactant in oil mix with fluorosurfactant pre-saturated with DTT effectively dissolving the hydrogel by reducing the disulfide bonds of the hydrogel from the PEGSSDA reagent. This hydrogel dissolution should improve the ePCR efficiency.

Extraction of macromolecules after ePCR is accomplished by adding 1% SDS in TK buffer (20 mM Tris-HCL, pH 7.5, 60 mM KCl, 10 mM DTT) to cells extracted from the emulsion and incubating at 95° C. for 5 min. Cysteines are alkylated by incubating with 40 mM iodoacetamide for 1 h at 37° C. in dark. Samples are diluted 10-fold in TK buffer and incubated with 20 ng/µL porcine trypsin (1:50 trypsin:protein ratio) for 3 h at 37° C. Following treatment, lysate is again centrifuged and resuspended in 1×TK buffer for downstream processing and library preparation.

Example 15. Amplification of CBPs within Compartments and Coupling of Amplified CBPs to DNA Fragments In this Example, the aqueous phase enclosed in the droplets comprises 1× Phusion High-Fidelity PCR Master Mix (Thermo Fisher) and 1.0 mg/mL recombinant BSA (New England Biolabs). A pair of barcode primers ($CBP_F$ at 1 uM and $CBP_R$ at 0.05 uM) are designed to amplify the cell barcode sequence within the droplet, as shown in FIG. 3. A single primer (GSP-R at 0.2 uM) is used to linearly amplify the cell DNA fragments. There is a 10 bp overlap region between $CBP_R$ and 5'-end of cell DNA fragment to facilitate the coupling reaction to link two fragments together (FIG. 3). Because all copies of the cell barcode (CBC) present in CBP in the same droplet are originated from a single barcode sequence, after coupling reaction all cell DNA fragments from the same droplet representing a single cell will be labeled with the same CBC. With a large pool of degenerate CBC sequences ($4^{14}=2.68*10^8$), the chances that cell DNA fragments from different droplets receive the same CBC sequences are low.

The PCR program is separated into two stages. The first stage uses a higher annealing temperature (65° C.) to amplify both the cell barcode and cell DNA fragments. The second stage uses a lower annealing temperature (48° C.) to allow the 10 bp overlap region between $CBP_R$ and 5'-end cell DNA fragment to anneal and extend to form coupling products. The complete PCR program is as following: 98° C. initial denaturation for 1 min, 22 cycles of stage one (98° C. for 10 sec, 65° C. for 40 sec, 72° C. for 30 sec), 5 cycles of stage two (98° C. for 10 sec, 48° C. for 2 min, 72° C. for 40 sec), and a final extension at 72° C. for 2 min.

After the completion of PCR amplification and coupling reaction, 15 uL of Ethylenediaminetetraacetic acid (EDTA, 100 mM) (Invitrogen) is added and the entire emulsion reaction is transferred to a DNA LoBind tube (Eppendorf). To break the droplets and recover the coupling product, 200 uL of 1H,1H,2H,2H-Perfluoro-1-octanol (Sigma) is added. The mixture is then vortexed for 10 s at maximum speed, followed by centrifuging for 5 min at 20,000×g. After phase separation, the aqueous phase on the top that contains the coupling product is transferred to a fresh LoBind tube for downstream purification (Redin, D., et al., (2017) Droplet Barcode Sequencing for targeted linked-read haplotyping of single DNA molecules. Nucleic Acids Res, 45, e125).

Example 16. In Silico Merging Macromolecules from the Same Droplet Barcoded by Two or More Barcode Sequences for Further Analysis In some embodiments of the disclosed barcoding methods, after removing cell barcode probes (CBPs) that are not bound to the genomic DNA (gDNA) from the cells, two or more CBPs remain bound to gDNA inside cells, which results in two or more cell barcode sequences being encapsulated and amplified in the same droplet, and subsequently used to label the desired macromolecules originated from the same cell. To avoid mis-interpretating these barcodes to multiple cells, these barcodes need to be merged in silico. One strategy to accomplish this is to utilize Unique Molecular Identifier (UMI) sequences incorporated in the macromolecules, such as cell DNA fragments. The cell barcodes from the same droplets will share UMI sequences at a rate exceeding that may be expected by chance (Lareau, C. A., et al. (2019) Droplet-based combinatorial indexing for massive-scale single cell chromatin accessibility. Nat Biotechnol, 37, 916-924; Lareau, C. A., et al., (2020) Inference and effects of barcode multiplets in droplet-based single cell assays. Nat Commun, 11, 866). For each pair of cell barcodes, the Jaccard index is computed over the UMI sequences, providing a measure of how similar the UMI sequences are for any pair of cell barcodes (FIG. 11A). From these pairwise Jaccard index statistics, a knee plot is generated to determine pairs that are likely to have originated from the same droplet, and a Jaccard index cutoff value can be used to determine barcode pairs that need to be merged (FIG. 11B).

Example 17. Amplification of Padlock CBP by Rolling-Circle Amplification (RCA)

A padlock CBPs are circularized oligonucleotides (Nilsson, M. 2006. Lock and roll: single-molecule genotyping in situ using padlock probes and rolling-circle amplification. Histochem. Cell Biol. 126: 159-164). Before circularizing, linear CBPs are designed to include the complementary nucleotide sequences of the target sequence of gDNA in both terminal regions, and unique cell barcodes in the middle region. When the linear CBP is in close proximity with the target sequence of gDNA, the terminal regions of the CBP hybridize with the target sequence of gDNA and form the double strands, while the middle region remains as a single strand without hybridization. After the hybridization, the two ends can be connected by DNA ligase to form a circularized oligonucleotide as a padlock for the target gDNA sequence (FIG. 6). Next, DNA polymerase having strong strand displacement activity can be utilized amplify the cell barcode sequence of the padlock CBP by rolling-circle amplification (RCA). Examples of such DNA polymerase enzymes include, but not limited to, Klenow exo-, Bsu large fragment, phi29 the large fragment of Bst DNA polymerase, an engineered thermostable polymerase having a strong strand displacement activity, such as, for example, Taq DNA polymerase mutant (Ignatov K B, et al., A strong strand displacement activity of thermostable DNA polymerase markedly improves the results of DNA amplification. Biotechniques. 2014 Aug. 1; 57(2):81-7).

Example 18. In Situ cDNA Synthesis and Crosslinking

Using a protocol adapted from Lee et al. (Lee, Je Hyuk, et al., 2014. "Highly Multiplexed Subcellular RNA Sequencing in Situ." Science 343 (6177): 1360-63), the mRNA within fixed and permeabilized cells are in situ reverse transcribed using the following protocol: a 200 uL mixture containing 4,000 U M-MuLV reverse transcriptase (Enzymatics), 250 uM dNTP (Enzymatics), 40 uM aminoallyl dUTP (Anaspec), 50 U RNase inhibitor (Enzymatics), and 100 pmol phosphorylated $CBP_F$-oligo dT primer prepared on ice is added to cells at 25° C. for 10 minutes. The concentration of aminoallyl dUTP is varied depending the cell type and the application. Generally, a high incorporation rate of aminoallyl dUTP results in better cross-linking and reduced cDNA diffusion but a lower amplicon density. The sample is then incubated overnight in a humidified 37° C. chamber. The sample is washed using 1×PBS and cross-linked using BS(PEG)9 (Thermo Scientific), diluted to 50 mM in PBS, for 1 hour at 25° C. 1 M Tris (G Biosciences) is added to quench the reaction for 30 minutes at 25° C. A mixture of DNase-free RNases (Roche Diagnostics) and RNase H (Enzymatics) is added to degrade residual RNA for 1 hour at 37° C.

Example 19. RCA Pre-Amplification of CBP

Using a protocol adapted from Lee et al., 2014, an optional rolling circle amplification (RCA) reaction can be used to pre-amplify the CBP tags within the nucleus prior to emulsion or droplet compartmentalization followed by emulsion PCR. The initial CBP pre-RCA probe is comprised of a 5' GBS and a 3' $CBP_F$ primer sequence that can anneal to a pre-circularized cellular barcode probe via a complementary $CBP_F$ sequence. An architecture for the primer suitable for this process is shown in FIG. 7C except the barcodes are inserted during the RCA step. The annealing reaction is initiated by adding 200 uL mixture containing 100 nM pre-circularized CBP construct in 2×SSC and 30% formamide for 15 minutes at 60° C. The sample is washed using 2×SSC, and a 200 uL RCA amplification mixture containing 500 U Phi29 DNA polymerase (Enzymatics), 250 uM dNTP is added. The sample is incubated in a dry 30° C. chamber overnight and cross-linked using BS(PEG)9 diluted to 50 mM in PBS for 1 hour at 25° C. After a rinse with PBS, 1 M Tris is added to quench the reaction for 30 minutes. At this point, the sample can be stored in nuclease-free 1×PBS at 4° C.

Example 20. Attaching Positional Barcodes to Macromolecules (Such as Polypeptides) to Preserve Spatial Information in a Spatial Sample (e.g., Tissue Section)

Positional barcodes are introduced into a mounted tissue section (fresh frozen or paraffin embedded) by overlaying and assembling DNA barcoded beads used as spatial probes on the surface of the mounted tissue section on the slide (Fischer et al., *CSH Protoc* (2008) pdb prot4991; Fischer et al., *CSH Protoc* (2008) pdb top36; Fischer et al., CSH Protoc. (2008) pdb.prot4988). Fresh-frozen tissue cryo-sections (e.g., about 5 to about 100 µm thickness, such as 10 µm thickness) are transferred onto the slide surface and undergo 4% formaldehyde fixation for about 20 minutes. The tissue section slides are dried with forced nitrogen air before the barcode bead overlay. Barcoded beads are brought into contact with the tissue section by incubating beads with the slides and spinning down the beads to form a monolayer on the slide surface. The tissue surface is covered with beads attached non-specifically to the tissue surface through adhesive forces such as charge interactions, DNA hybridization, or reversible chemical coupling. In another embodiment, the beads are embedded in a hydrogel coated over the tissue section surface. In one embodiment, the beads are porous to accommodate a higher loading of barcodes on a bead (a porous 5 um bead can be loaded with >$10^{10}$ DNA barcodes, e.g. Daisogel SP-2000-5 porous silica beads). Positional barcodes are attached to the beads via a photocleavable linker enabling easy removal and subsequent diffusive transfer of the barcodes to the tissue section. Positional barcodes can be released by enzymatic, chemical, or photo-cleavage of a cleavable linker. These barcodes permeate the tissue slice and anneal to the DNA stubs (e.g., recording tags) attached to polypeptides within the tissue slice. A polymerase extension step is used to write the positional barcodes to the DNA recording tags on the proteins, generating an extended recording tag.

In alternative embodiments, positional barcodes are provided as a part of the CBPs (see, for example, FIG. 4A, where exemplary CBS comprises SpBC).

Further details for attaching positional barcodes to macromolecules are provided as follows:

Tissue Section Permeabilization

For fresh frozen samples, the tissue section is permeabilized using standard methods such a 0.1%-1% TX-100 incubation prior to chemical activation of protein molecules (Fischer et al., CSH Protoc (2008) pdb top36). For FFPE tissue sections, the embedding media is removed (e.g., dewaxed in the case of paraffin), and the sections are permeabilized using standard methods (Ramos-Vera et al., J Vet Diagn Invest. (2008) 20(4):393-413). Standard conditions for tissue permeabilization include incubation in 0.1%-1% TX-100 or NP-40 for 10-30 min at 0.1 to 1%. Tween-20, Saponin, Digitonin can also be used at 0.2%-0.5% for 10-30 min (Fischer et al., CSH Protoc (2008) pdb top36).

Chemical Activation and DNA Tagging

After tissue section permeabilization and protein denaturation, in a preferred embodiment, proteins are chemically activated by incubation with an amine bifunctional bioconjugation reagent such as methyltetrazine-sulfo-NHS ester (Click Chemistry Tools); other bifunctional amine reactive bioconjugation reagents can also be employed (Hermanson, Greg. 2013. "Bioconjugate Techniques: Third Edition." Bioconjugate Techniques: Third Edition, August, 1-1146). The density of DNA tagging can be controlled by titrating in non-activated amine modifying reagent such as mPEG-NHS ester. An exemplar activation condition includes incubating slides with 1 mM NHS-mTet for 30 min in PBS buffer (pH 7.4) to label epsilon-amine on lysines. Wash 3× in PBS supplemented with 5 mM ethanolamine for 10 min each to quench reaction. After activation and washing, a common DNA tag (comprising a suitable architecture for a recording tag) containing an iEDDA coupling label such as trans-cyclooctene (TCO), norbornene, or vinyl boronic acid is incubated with the tissue section to "click on" the DNA tags to the mTet moieties on the activated protein molecules (Knall et al., Tetrahedron Lett (2014) 55(34): 4763-4766). An exemplar coupling condition includes incubating the slide with 1 mM TCO-DNA stub for 1 h in PBS buffer (pH 7.4). Excess TCO-DNA is washed away using PBS buffer washes. The DNA stub is comprised of a priming sequence present on the final amplified CBP sequence enabling primer extension to copy the CBP sequence to each DNA-tagged protein analyte within the cell or cellular compartment. In addition, the DNA stub may be comprised of a amplification region, a barcode region (e.g. sample barcode), and a primer region capable of annealing to the CBP to facilitate a primer extension step (Fig. ?).

DNA Barcoded Bead Distribution Over Tissue Section.

In a preferred embodiment, DNA barcoded beads are generated through a split-pool synthesis strategy described in (Klein et al., Lab Chip (2017) 17(15): 2540-2541) or in (Delley and Abate. 2021. "Modular Barcode Beads for Microfluidic Single Cell Genomics." Scientific Reports 11 (1): 10857). Each bead has a single population of positional barcodes. In one embodiment, the beads are 0.5-10 um in diameter and contain a positional barcode flanked by an upstream spacer sequence and a downstream primer extension sequence complementary to the DNA tag sequence attached to the proteins. In a preferred embodiment, the DNA barcodes are attached to the bead with a photocleavable linker, such as PC linker (PC Linker-CE Phosphoramidite, Glenn Research). In another embodiment, tissue section slides are assembled in a capillary gap flow-cell (~50 um gap) such as the Te-Flow system from Tecan (Gunderson, Methods Mol Biol (2009) 529: 197-213). This provides a format for easily exchanging solutions on the slide surface.

In one embodiment, DNA barcoded beads are distributed across the surface of the tissue section, using the capillary gap flow cell system. The DNA barcode beads contain complementary sequences to the DNA tags on the proteins. This creates a "stickiness" of the barcoded beads to the surface of the tissue section with exposed DNA tags. In another embodiment, the beads are 0.5-10 um in diameter and contain both DNA barcodes and free amines on their surface. These free amine groups enhance adhesion to tissue surfaces since most tissues are slightly negatively charged (this is the mode to mount tissue slices on positively-charged slides for IHC). The barcoded beads can be covalently cross-linked to the tissue using standard fixation chemistry with glutaraldehyde.

Transferring Positional Barcodes from Beads to DNA Tagged Proteins

After assembling barcode beads on the surface of the tissue section, the positional barcodes are photo-cleaved from the bead (via long wavelength UV exposure, e.g. 365 nm UV). A majority of linkages are cleaved, but not all, since photo-cleavage is generally only 70-90% efficient and can be adjusted by UV intensity and exposure time (3-100 mW/cm2 @ 340-365 nm for 1-60 min) (Bai et al., Proc Natl Acad Sci USA 100(2): 409-413). The cleaved positional barcodes diffuse into the tissue section and hybridize with their complement on DNA tags (e.g., recording tags) previously attached to proteins. After incubation for about 30 min, the tissue section is exposed to a polymerase extension mix to transfer positional barcode information from the hybridized positional barcode to the polypeptide DNA recording tag.

Example 21. Preparing Spatially Ordered Array of Positional Barcode Probes (PBPs) on Glass Slides The protocol is adapted from (Srivatsan, S. R., et al. (2021) Embryo-scale, single-cell spatial transcriptomics. Science, 373, 111-117) with modifications. A thin membrane of dried agarose is fabricated on the surface of microscope slides (Superfrost Plus, Thermofisher) to absorb and retain an array of spotted PBPs (see below for PBP spotting procedure). Nuclease-free agarose is prepared by adding 3% w/v low melting temperature agarose powder (SeaPlaque, Lonza, Bend, Oreg.) to deionized water containing 0.1% v/v diethyl pyrocarbonate. The mixture is incubated for 2 hr at room temperature, and autoclaved for 15 min. The uniform thickness of the layer of agarose across the slide surface is patterned using spacers of two stacked 22×22 mm, number one thickness (0.15±0.02 mm each) coverslips overhanging either end of the slide. Molding of the agarose is performed by pipetting a 300 uL volume of heated agarose solution into the center of the slide and slowly placing a second slide onto the agarose solution avoiding the formation of bubbles. The agarose is solidified by putting on ice for 30-60 min. The resulting thin layer of agarose gel is dried onto the bottom slide overnight in a biosafety cabinet. All agarose slides are UV-treated for 20-30 min prior to spotting to further protect against nuclease activity.

The space-grid array of PBPs is spotted onto agarose-coated slides using a QArray2 microarray scanner (Genetix, New Milton, Hampshire, GB). A series of 384-well high sample recovery plates (Molecular Devices, San Jose, Calif., X7020) is prepared containing PBPs (Integrated DNA Technologies, Coralville, Iowa), and 0.5% v/v glycerol to achieve the predetermined PBP layout. In an 18 mm by 1.8 mm area, 7,056 of unique PBP can be spotted (mean radius of 73.2±14.1 um; mean spot-to-spot center distance of 222±7.5 um).

Example 22. Barcoding Macromolecules with Positional Barcodes in Tissue Sections to Record Spatial Information Single-stranded DNA (ssDNA) can label the nuclei of permeabilized cells (Srivatsan, S. R., et al. (2020) Massively multiplex chemical transcriptomics at single-cell resolution. Science, 367, 45-51). PBPs are prepared as in Example 21 and transferred in their arrayed pattern from the space-grid slides to fresh-frozen sections by diffusion through cell permeabilization buffer. First, the tissue section slide is placed so that it rested (tissue facing up) with the tissue section between two transfer clips. Subsequently, 500 μL of nuclei permeabilization buffer [10 mM Tris/HCl pH 7.4, 10 mM NaCl, 3 mM MgCl2 with 1% v/v superase inhibitor (Invitrogen) and 0.1% v/v IGEPAL CA-630 (Sigma Aldrich)] is pipetted gently onto the tissue section. A space-grid array slide is then positioned (agarose surface facing the tissue section) so that the arrayed PBPs are aligned between the two transfer clips and spanned the tissue section's extent. After transferring PBPs to cell nuclei, cells of the tissue section are scraped using a cell scraper (Fisherbrand, GDPC240) into a 4% paraformaldehyde fixing solution. After fixation for 15 minutes on ice, cells are spun down in 1.5 mL tubes in a chilled benchtop centrifuge at 800 g for 10 minutes. The supernatant in each tube is removed and cells are pooled in 1 mL of NSB [Nuclei Suspension Buffer (10 mM Tris/HCl pH 7.4, 10 mM NaCl, 3 mM MgCl2) with 1% v/v superase inhibitor (Invitrogen) and 1% v/v BSA (New England Biolabs)] and subjected to barcode amplification and macromolecule labeling as described in Examples 15 and 20.

Example 23. Next Generation Protein Analysis (NGPA) and Next Generation Protein Sequencing (NGPS) Assays Macromolecules barcoded with CBPs can be pooled together from individual cells and further analyzed by a variety of methods. For peptide macromolecules, either NGPA or NGPS assays can be used (see US 20190145982 A1).

In these assays, peptide molecules are attached to nucleic acid recording tags (each recording tag includes a cellular barcode from CBP and, optionally, a positional barcode) and recording tag-peptide conjugates are immobilized on a solid support, such as beads. For example, recording tag-peptide conjugates are joined to immobilized bead-attached capture DNAs via nucleic acid hybridization, as described in US 2020/0348308 A1. Briefly, conjugates (20 nM) are annealed to the capture DNAs attached to beads in 5×SSC, 0.02% SDS, and incubated for 30 minutes at 37° C. The beads are washed once with PBST and resuspended in 1× Quick ligation solution (New England Biolabs, USA) with T4 DNA ligase. After a 30-minute incubation at 25° C., and the beads are washed with PBST, two times of 0.1M NaOH+ 0.1% Tween-20 and twice of PBST.

Immobilized recording tag-peptide conjugates are analyzed by incubation with one or more binding agents that are capable of specifically binding to the peptide (or a component of the peptide, such as one or more amino acid residues, or post-translational modification of the peptide) of one of recording tag-peptide conjugates. Each binding agent is conjugated with a nucleic acid coding tag that comprises barcode comprising identifying information regarding the associated binding agent. If affinity of the binding agent to the immobilized peptide is strong enough (typically, Kd should be less than 500 nM, and preferably, less than 200 nM), the coding tag associated with the binding agent and the recording tag associated with the peptide form hybridization complex via hybridization of the corresponding spacer regions to allow transfer of identifying information from the coding tag to the recording tag via a primer extension reaction (encoding reaction), generating extended recording tag. This can be performed in parallel for multiple immobilized peptides and for multiple binding agents. If more than one binding agent bind specifically to the peptide, history of binding events is recorded in the extended recording tag associated with the peptide. Sequencing of extended recording tags after one or more encoding cycles is used to identify binding agent(s) that was(were) bound to the immobilized peptide. At the same time, estimating fractions of the recording tags being extended (encoded) during primer extension reaction provides estimate of efficiency of the encoding reaction, which directly correlates with binding affinity of the binder to the peptide.

In NGPA assay, specific antibodies recognizing peptide epitopes are employed as binding agents, which provides high throughput protein characterization based on epitope mapping (by associating identifying information of the binding agents having known specificities extracted from the extended recording tags with sequences of proteins). In NGPS assay, a set of binding agents (5-20 binding agents) are employed that specifically recognize different modified N-terminal amino acid (NTAA) residues of peptides. After one cycle of binding and encoding, the modified NTAA residues are removed (chemically or enzymatically), exposing new NTAA residues of peptides. New NTAA residues are modified with a functionalizing reagent, followed by incubating modified immobilized peptides with the set of binding agents, and the second cycle of binding and encoding occurs. Thus, full cycle of NGPS consists of NTAA modification, binding, encoding and NTAA cleavage. This cycle can be repeated 2-15 times, which results in generation of long extended recording tags associated with immobilized peptides and bearing identifying information regarding all binding agents that were bound to the particular peptide. Since specificity of the binding agents is known, it can be used to decode sequence of the peptide in high throughput manner.

Example 24. Single-Cell Protein Detection Based on NGPA Assay Using In-Droplet Amplified Cell Barcodes Cells are fixed and permeabilized as described in Example 2. Recording tags (R-tag) are attached on cellular proteins via a one-pot, two-step reaction by combining cell samples with methyltetrazine-activated DNA (MTZ-DNA) oligonucleotides and the amine-reactive cross-linker NHS-trans-cyclooctene (NHS-TCO) (see US20190276818 A1, incorporated herein, and Gehring, J., et al. (2020) Highly multiplexed single-cell RNA-seq by DNA oligonucleotide tagging of cellular proteins. Nat Biotechnol, 38, 35-38). The cells are then undergone two cycles of NGPA reaction each consisted of six steps: 1) incubate cells for 30 min at room temperature with antibody mix conjugated with coding tag (C-tag). 2) wash cells with PBST. 3) Information transfer from C-tag to R-tag using an extension mix containing 0.2 U/uL Klenow Exo- and 0.125 mM dNTP. The extension reaction was conducted at 37° C. for 10 min. 4) wash cells with PBST, 5) SHT buffer (1% Tween20, 0.1M NaOH) was applied to denature double stranded DNA formed during extension and strip antibodies off their respective target proteins. 6) wash cells two more times with PBST. The antibody mixtures were consisted of C-tag-conjugated antibodies targeting different proteins. To distinguish different protein targets, C-tags on different antibodies were assigned with different barcode sequences (antibody barcodes). Two cycles of sequential NGPA reactions are used to improve the specificity.

After the NGPA reaction, C-tag identifying information from cycle 1 and cycle 2 antibodies are recorded on R-tag to form a composite oligo (R-C1-C2) that reflects both the identity and quantity of the protein targets. These composite oligos are still confined in fixed cells because R-tag are anchored on the cellular proteins. The cells are then incubated with CBPs as described in any one of Examples 5, 6, 8-12 to incorporate 1-2 unique CBPs into each individual cell followed by encapsulating cells with CBPs into droplets for CBP amplification and R-C1-C2 barcoding.

Example 25. Single-Cell ATAC-Seq Using In-Droplet Amplified Cell Barcodes

The first step of single-cell ATAC-seq protocol is to prepare nuclei according to Corces, M. R., et al. (2017) An improved ATAC-seq protocol reduces background and enables interrogation of frozen tissues. Nat Methods, 14, 959-962. Cells grown in tissue culture are pretreated with 200 U/ml DNase (Worthington) for 30 min at 37° C. to remove free-floating DNA in the media. The cells are then collected and resuspended in cold PBS. After the cells are counted, 50,000 cells are resuspended in 1 ml of cold ATAC-seq resuspension buffer (RSB; 10 mM Tris-HCl pH 7.4, 10 mM NaCl, and 3 mM $MgCl_2$ in water). Cells are centrifuged at 500 g for 5 min in a pre-chilled (4° C.) fixed-angle centrifuge. After removing supernatant, cell pellets are resuspended in 50 µl of ATAC-seq RSB containing 0.1% NP40, 0.1% Tween-20, and 0.01% digitonin. The cell lysis reaction is carried out on ice for 3 min. After lysis, 1 ml of ATAC-seq RSB containing 0.1% Tween-20 (without NP-40 or digitonin) is added, and the tubes are inverted to mix. Nuclei are then centrifuged for 10 min at 500 g in a pre-chilled (4° C.) fixed-angle centrifuge. For transposition reaction, nuclei are resuspended in 50 µl of transposition mix (25 µl 2×TD buffer, 2.5 µl transposase (Illumina), 16.5 µl PBS, 0.5 µl 1% digitonin, 0.5 µl 10% Tween-20, and 5 µl water) and incubated at 37° C. for 30 min.

The tagmented nuclei are then labeled with CRISPR/CAS CBP as described in Example 10 to assign 1-2 cell barcodes to individual cell nuclei. Then, the nuclei are encapsulated in droplets together with PCR reagents for cell barcode amplification and ATAC fragment barcoding.

Example 26. Enabling scATAC-Seq with CBP Nuclei Labeling

In situ ATAC-seq protocols are adapted to enable generation in situ ATAC-Seq protocols compatible with cellular barcode (CBP) and Spatial barcode labeling. Namely, using methods described in US 2019/0032128A1 and by Mimitou et al, scATAC-Seq incorporating CBP labels can be performed concomitantly with scRNA-Seq and scProt-Seq.

Example 27. Sample Pre-Indexing Allows More than One Cell to Load in One Droplet During Compartmentalization Step The typical single-cell platforms require no more than one cell encapsulated in one droplet. Data from droplets containing two or more cells are discarded. However, multiple cells can be loaded in one droplet if they are pre-indexed before droplet encapsulation and can be demultiplexed after sequencing. One strategy is to split the cell sample into multiple pools and label cell transcriptomes in each pool with primers containing sample barcodes during reverse transcription (Datlinger, P., et al. (2021) Ultra-high-throughput single-cell RNA sequencing and perturbation screening with combinatorial fluidic indexing. Nat Methods, 18, 635-642). Alternatively, cell hashing, as described by Stokeus et al., can be employed to add sample "hashing" barcodes to the cell via barcoded antibodies that bind cell surface markers such as CD45, CD98, CD44, and CD11a (Stoeckius, et al., 2018. "Cell Hashing with Barcoded Antibodies Enables Multiplexing and Doublet Detection for Single Cell Genomics." Genome Biology 19 (1): 224). During later stage emulsion PCR, these sample "hash" barcodes can be fused to the CBP sequences to enable identification of the single cell and it sample of origin. Next, cells containing sample indexed macromolecules or cells with sample hash barcoded antibodies bound to surface markers are pooled, randomly mixed, and encapsulated using a standard microfluidic droplet generator, such that most droplets are filled, and multiple cells could occupy the same droplet. The numbers of cells encapsulated in individual droplets are controlled so that chances of two cells carrying the same sample barcode are small. Inside the droplets, macromolecules (such as RNA transcripts) are labeled with the amplified cell barcodes. Although cells in the same droplet share the same cell barcode, the sample barcodes incorporated during the reverse transcription are distinct. As a result, the combination of the cell barcode and sample barcode uniquely identifies single cells.

During the NGPA workflow for analysis of polypeptide macromolecules, the recording tag (R-tag) containing sample barcode is employed to label different sample pools. The barcoded samples are then pooled and processed as a single sample. After antibody binding and coding tag (C-Tag) information transfer (see Example 24), the cells carrying protein identity and quantitation information are encapsulated and labeled with cell barcodes in droplets as described above. In this situation the sample barcode introduced in the R-tag is used to distinguish cells in the same droplets.

Example 28. DNA-Binding Protein Design and Use for CBP Labeling in Fixed and Permeabilized Cells A designed TALE protein (dTALE) is designed to bind to the human genomic target region from chr7 at chromosomal location: 63367837 to 63/367,857 (AT-GAGTTTCTGGGACTGACGGT, SEQ ID NO: 3). The AT sequence lies outside binding region but serves as an AT dinucleotide region for downstream psoralen crosslinking. The sequence of the dTALE protein is based on AvrXa10 (Cuculis, et al., 2020. "Divalent Cations Promote TALE DNA-Binding Specificity." Nucleic Acids Research 48 (3): 1406-22). The CBS sequence is attached to dTALE via a SpyCatcher Fusion which links to a SpyTag-CBP sequence (see FIG. 8C, where dCas9 is replaced with dTALE). The psoralen moiety is comprised of psoralen-TEG-azide (Biosearch Technologies), and attached to synthetic alkyne lysine amino acid (z N6-((Prop-2-yn-1-yloxy)carbonyl)-L-lysine hydrochloride) on the SpyTag peptide using standard click chemistry bioconjugation techniques.

The dTALE is designed to target 20-mer sequence from human chr7 using a tandem series of 19.5 RVD repeats. SpyCatcher can be appended to the N or C terminus of the dTALE. The core sequence of the dTALE is (RVD dipeptides shown in bold code for binding to the DNA sequence GAGTTTCTGGGACTGACGGT, SEQ ID NO: 3):

SEQ ID NO: 4
MGPLCTPSRSSHHHHHHSSGLVPRGSHMLDTS

LLDSMPAVGTPHTAAAPAECDEVQSGLRAA

DDPPPTVRVAVTAARPPRAKPAPRRRAAQPSD

ASPAAQVDLRTLGYSQQQQEKIKPKVRSTVAQ

TYQDIIRALPEATHEDIVGVGKQWSGARALEA

LLTEAGELRGPPLQLDTGQLLKIAKRGGVTAV

EAVHAWRNALTGAPLNLTPDQVVAIASNIGG

KQALETVQRLLPVLCQDHG

LTPDQVVAIASNNGGKQALETVQRLLPVLCQDHG

LTPDQVVAIASNIGGKQALETVQRLLPVLCQDHG

LTPDQVVAIASNNGGKQALETVQRLLPVLCQDHG

LTPDQVVAIASNGGGKQALETVQRLLPVLCQDHG

LTPDQVVAIASNGGGKQALETVQRLLPVLCQDHG

LTPDQVVAIASNGGGKQALETVQRLLPVLCQDHG

LTPDQVVAIASHDGGKQALETVQRLLPVLCQDHG

LTPDQVVAIASNGGGKQALETVQRLLPVLCQDHG

LTPDQVVAIASNNGGKQALETVQRLLPVLCQDHG

LTPDQVVAIASNNGGKQALETVQRLLPVLCQDHG

LTPDQVVAIASNNGGKQALETVQRLLPVLCQDHG

LTPDQVVAIASNIGGKQALETVQRLLPVLCQDHG

LTPDQVVAIASHDGGKQALETVQRLLPVLCQDHG

LTPDQVVAIASNGGGKQALETVQRLLPVLCQDHG

LTPDQVVAIASNNGGKQALETVQRLLPVLCQDHG

LTPDQVVAIASNIGGKQALETVQRLLPVLCQDHG

LTPDQVVAIASHDGGKQALETVQRLLPVLCQDHG

LTPDQVVAIASNNGGKQALETVQRLLPVLCQDHG

LTPDQVVAIASNNGGKQALETVQRLLPVLCQDHG

LTPDQVVAIASNGGGKQALESIVAQLSRPDPALA

ALTNDHLVALACLGGRPALDAVKKGLPHAPELIR

RINRRIPERTSHRVA,

The dTALE protein is expressed an purified as described in Cuculus et al., 2020, "Divalent Cations Promote TALE DNA-Binding Specificity." Nucleic Acids Research 48 (3): 1406-22. The binding of the dTALE protein is accomplished as follows: fixed and permeabilized cells are incubated in 20 mM Tris-Cl buffer, pH 7.5, supplemented with 50 mM KCl, 10 mM MgCl2, 0.1% Tween-20, and 100 nM CBP-labeled dTALE protein at 30° C. for 30 min. After binding and washing, psoralen crosslinking is achieved by exposing the cells to long wavelength UV light, wherein the intercalated psoralen moiety cross-links the two thymidine bases located on opposing DNA strands (Bornet et al. 1995). The optimal UV exposure is 6 J/cm2 of 365 nm (long UV) applied directly to the cells placed in shallow wells on ice.

Example 29. Isolation of Nuclei from Cells Suspensions

As described by Massoni-Badosa et al. (Massoni-Badosa, et al., 2020. "Sampling Time-Dependent Artifacts in Single-Cell Genomics Studies." Genome Biology 21 (1): 112), nuclei are isolated starting with an input of ~0.3-1.0×10^6 cells in a 1.5 ml microcentrifuge tube and centrifuged at 500×g for 5 min at 4° C. The supernatant is removed, and 100 µl of chilled Lysis Buffer (10 mM Tris-HCl (pH 7.4); 10 mM NaCl; 3 MgCl2; 0.1% Tween-20; 0.1% Nonidet P40 Substitute; 0.01% Digitonin and 1% BSA) is added and pipette-mixed about 10 times. Samples are then incubated on ice during 3 min. Following lysis, 1 mL of chilled Wash Buffer (10 mM Tris-HCl (pH 7.4); 10 mM NaCl; 3 MgCl2; 0.1% Tween-20 and 1% BSA) is added and pipette mixed. Nuclei are centrifuged at 500×g for 5 min at 4° C. to create a nuclear pellet. After removal of the supernatant, nuclei are resuspended in 1×PBS buffer for further processing. Isolated nuclei can be used instead of cells in the examples and methods disclosed above.

Example 30. Improving Specificity of CBP Probes to Target gDNA Loci by Employing In Situ Hybridization and Ligation of Proximity Probes The use of two or more proximity probes which anneal adjacent or nearby to each other (gapped probes) on the target gDNA locus can generate a ligated CBP probe product with improved specificity relative to the use of a single probe. The ligation product from the proximity probes can be formed directly by ligation of adjacent probes, or by a gap-fill ligation step for gapped probes. In addition, one can employ more than two probes in a proximity-ligation approach as well to enhance specificity. Ligation of adjacent or gap-extended probes requires a phosphate moiety on one terminus (typically 5') and a hydroxyl moiety on the other terminus (typically 3') at the ligation junction. In some cases, the terminus phosphorylation requirement is to be reversed using RtcB ligases (Das, et al., 2013. "Rewriting the Rules for End Joining via Enzymatic Splicing of DNA 3'-PO4 and 5'-OH Ends." Proceedings of the National Academy of Sciences of the United States of America 110 (51): 20437-42) or via phosphoramidite chemical ligation (3' phosphate; 5' amine). Additionally, a chemical ligation reaction between proximity probes comprised of 3'-propargyl and 5' amine termini at the ligation junction can be joined using CuAAC reaction to ligate the two proximity probes (El-Sagheer et al., 2017. "Single Tube Gene Synthesis by Phosphoramidate Chemical Ligation." Chemical Communications 53 (77): 10700-702).

In some embodiments of proximity probe ligation, two nucleic acid probes are designed to anneal adjacent to each other on a target gDNA locus. In a preferred embodiment, the two probes are designed to a non-transcribed region of a single copy locus to prevent interfering signal from transcribed RNA. In brief, cells or tissue sections are fixed and permeabilized as described in Examples 2-4. A pair of CBP proximity probes are annealed to the fixed and permeabilized cells/tissue. Namely, the CBP iFISH probe sequences described in Example 5 are modified to act as sequences for proximity ligation probes. In some preferred embodiments, the upstream and downstream GBS sequence arms of the CBP probe have 17-30 bases of homology with single copy genomic loci, preferably a non-transcribed and non-repetitive region. Namely the iFISH probe: CBP_Ch11-344380; TGGCCAGGAGGAGACTCTTCCAGGTCTC-CCTTCTGACACC (SEQ ID NO: 5) can be used to generate a pair of proximity-ligation probes by splitting the GBS region into an upstream assay arm (underlined 20 bases) and downstream assay arm (bolded 20 bases) (5'-TGGCCAGGAGGAGACTCTTCCAGGTCTCCCTTCT-GACACC-3' (SEQ ID NO: 5) to create the following pair of GBS proximity probes: CBP_Ch11-344380-Up (5'-X . . . X-TGGCCAGGAGGAGACTCTTC-3'OH; SEQ ID NO: 6) and CBP_Ch11-344380-Down (5'-Phos-CAGGTCTCCCTTCTGACACC-X . . . X-3'OH; SEQ ID NO: 7). The X . . . X represents additional functional sequence elements (e.g., PCR priming sites, UMIs, cellular barcodes, spatial barcodes, and other barcodes) added to either or both the Upstream and/or Downstream GBS sequences to constitute the pair of proximity CBP probes. A similar pair of proximity CBP probes can be generated from the Example 5 iFISH probe sequence containing a PmeI site: Chr7 CBP: AAACCTTGCCAACCAT-GAGTTTCTGGGACTGACGGTGATG (SEQ ID NO: 2). Target gDNA sequence: chr7, from 63/367,821 to 63/367,861. Namely, the two CBP proximity probes derived from the iFISH probe are: 5'-X . . . X-AAACCTTGCCAACCAT-GAGT (SEQ ID NO: 8) and 5'-Phos-TTCTGGGACTGACGGTGATG-X . . . X (SEQ ID NO: 9). Again, X . . . X represents additional functional sequence elements as described above.

In situ hybridization of the paired CBP proximity probes to gDNA is facilitated by generation of single stranded DNA in the gDNA target region. This can be accomplished by methods as described in Example 8 using denaturation, strand invasion, and/or linearization approaches. Ligation and gap-fill ligation conditions similar to what is described in Example 9 are used to ligate the upstream and downstream CBP probes to form a complete CBP sequence for subsequent amplification and CBP labeling of cellular analytes.

Example 31. Labeling of Cellular Protein Analytes with Amplified gDNA-Associated CBP Probes Cellular protein molecules are denatured, and the F-amine group of lysine residues (K) is chemically conjugated to an activated universal DNA tag molecule that serves as a primer or ligation acceptor site from an amplified CBP probe. A two-step bioconjugation process is used to first attach a heterobifunctional linker comprised of an amine-reactive NHS moiety, a PEG or alkane linker, and an orthogonal reactive coupling handle. After coupling the heterobifunctional linker, an activated DNA tag stub is conjugated to the reactive handle. In this particular instance, NHS-PEG12-mTet, is used to activate the lysine F-amine group with an orthogonal reactive coupling handle, methyl tetrazine (mTet). The DNA tag is comprised of a 5' TCO moiety which readily couples to mTet via an iEDDA reaction. Excess DNA tag is washed away after coupling.

Sequence information from the amplified CBP probe is transferred to the DNA stub during a PCR amplification step. The DNA stub attached to the proteins acts as one primer (a small amount of free primer can also be used to enhance the amplification reaction) and an exogenously added primer is used as the second primer in the PCR reaction.

Exemplary workflow is shown in FIG. 15. After barcoding, individual cells are compartmentalized in droplets, followed by cell barcode amplification, transfer barcode information to rTags of protein analytes, and exemplary NGPA assay for the tagged protein analytes. The following steps can be performed using standard methods known in the art or disclosed above. (A) Single cells are fixed, permeabilized, and have their nuclei labeled with CBPs. (B) Single cells are encapsulated in droplets along with a polymerizable matrix and lysis buffer (for specific method conditions, see US 20190145982 A1; Tamminen and Virta 2015; Spencer, Tamminen et al. 2016). (C) Polymer matrix polymerizes and immobilizes DNA rTags within matrix. (D) Proteins released from the cell are conjugated to activated DNA rTags within polymer matrix. (E) Single cell polymer beads (SCPB) are extracted into aqueous phase and combinatorial barcodes can be added to SCPBs via a SCI-Seq split-pool process, as described in U.S. Ser. No. 10/144,950 B2; US20180273933 A1; O'Huallachain, et al., 2020, "Ultra-High Throughput Single-Cell Analysis of Proteins and RNAs by Split-Pool Synthesis." Communications Biology 3 (1): 1-19. (F) The resultant SCPBs can be used directly in a ProteoCode NGPA immunoassay (exemplary antibody readout shown) or processed for an NGPS assay for quantitative assessment of proteins from single cell.

Example 32. Amplification of Exemplary Polynucleotide Cell Barcode Probes by "Bridge" Amplification Using a Pair of Primers Attached to Porous Sepharose Beads To demonstrate amplification of polynucleotide barcode probes within permeabilized cells and/or nuclei by primers covalently attached to components of the permeabilized cells and/or nuclei, the following model experiment was performed (see FIG. 16A-B). An on-bead "bridge" amplification system was used comprising porous sepharose beads comprising two primers attached to their surfaces, namely P5 primer (5'-AATGATACGGCGACCACCGA-3'-SEQ ID NO: 10) and P7 primer (5'-CAAGCAGAAGACGGCAT-ACGAGAT-3'—SEQ ID NO: 11). Probe amplification on these beads using attached primers models amplification in permeabilized cells and/or nuclei.

P5 and P7 oligonucleotides (primers) were derivatized with trans-cyclooctene (TCO) and chemically immobilized on beads (NHS-Activated Sepharose High Performance, Cytiva, USA) modified with methyltetrazine (mTet) using TCO-mTet click chemistry. The densities of the P5 and P7 primers on beads were controlled by passivation as follows. A mixture of mTet-PEG-NHS and methyl-PEG-NHS was resuspended at 1 mM in DMSO and incubated with amine beads at room temperature overnight. The ratio of the Methyl to mTet PEG was titrated to adjust the final mTet surface density on the beads. Three different mTet densities were employed: 100 mM, 10 mM and 1 mM. Unreacted amine groups were capped with a mixture of 0.1M acetic anhydride and 0.1M DIEA in DMF (500 ul for 10 mg of beads) at room temperature for 2 hrs. After capping and washing 3 times in DMF, the beads were resuspended in phosphate coupling buffer at 10 mg/ml. TCO-P5 and TCO-P7 oligonucleotides were reacted with bead-immobilized mTet by the click chemistry reaction.

The beads with immobilized P5 and P7 primers were contacted with ~300 bp polynucleotide barcode probes each comprising one terminal oligonucleotide region complementary to P5 primer and another terminal oligonucleotide region complementary to P7 primer. The beads were subjected to PCR (conditions: 94° C. for 2 min, then [98° C. 20 s, 67° C. 30 s, 72° C. 1 min]×25 cycles) using 10,000 beads (having 100 mM mTet, 10 mM mTet, 1 mM mTet, or Negative Control (no mTet)) per reaction with a titration of the supplied polynucleotide barcode probes (500 pM-1 fM). Following PCR, bridge amplification effectiveness was measured by qPCR (KAPA Library Quantification Complete Universal Kit, Roche) to detect the amount of product formation on bead-bound tags. Resulting qPCR data was used for amplified probe quantification. The data are shown in Table 1 and in FIG. 16A-B.

TABLE 1 qPCR quantification of the amplified probes.

| qPCR quantification (nM) Input DNA | 100 mM mTet | 10 mM mTet | 1 mM mTet | Neg Ctrl |
|---|---|---|---|---|
| 500 pM | 38,070.710 | 9,859.871 | 1,443.692 | 45.936 |
| 100 pM | 56,317.880 | 6,896.521 | 513.707 | 4.656 |
| 20 pM | 19,999.697 | 4,893.717 | 53.631 | 0.527 |
| 4 pM | 32,612.860 | 918.246 | 15.969 | 0.108 |
| Negative-1 | 0.044 | 0.001 | 0.002 | 0.012 |
| 1 pM | 298.414 | 19.419 | 2.960 | 0.368 |
| 100 fM | 99.644 | 1.367 | 0.260 | 0.043 |
| 10 fM | 3.503 | 0.149 | 0.029 | 0.007 |
| 1 fM | 1.605 | 0.085 | 0.012 | 0.002 |
| Negative-2 | 0.001 | 0.000 | 0.001 | 0.001 |

The present disclosure is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for barcoding macromolecules from a sample comprising a population of cells, the method comprising the following steps:
   a) permeabilizing cells, and/or nuclei of the cells, from the population of cells of the sample;
   b) optionally making genomic DNA of the permeabilized cells and/or nuclei at least partially accessible to nucleic acid hybridization;
   c) delivering cell barcode probes to the permeabilized cells and/or nuclei of the permeabilized cells, wherein a given cell barcode probe comprises a genome binding element shared among the cell barcode probes, and a cell barcode unique for the given cell barcode probe, and wherein the genome binding element hybridizes to a region in the genomic DNA, thereby forming a nucleic acid duplex between the genome binding element and the region of the genomic DNA in the cells and/or nuclei;
   d) removing cell barcode probes that are not bound to the genomic DNA from the cells and/or nuclei, whereby no more than a defined number of copies of the cell barcode probe remain in each cell or nucleus;
   e) partitioning the cells and/or nuclei into a plurality of compartments; and
   f) amplifying the cell barcodes within compartments of the plurality of compartments, thereby forming amplified cell barcodes within the compartments,
   wherein nucleic acid recording tags are covalently attached to the macromolecules or derivatives thereof, and
   wherein the amplified cell barcodes or complements thereof are attached to the nucleic acid recording tags, thereby attaching the amplified cell barcodes or complements thereof to the macromolecules or derivatives thereof within the compartments to form barcoded macromolecules or derivatives thereof.

2. The method of claim 1, further comprising releasing the barcoded macromolecules from the compartments.

3. The method of claim 1, wherein the macromolecules being barcoded are polypeptides, mRNA molecules or cDNA molecules.

4. The method of claim 1, wherein the region in the genomic DNA is a non-repetitive region.

5. The method of claim 4, wherein the non-repetitive region in the genomic DNA is a non-coding region or a differentially methylated region.

6. The method of claim 1, wherein the defined number of copies is one copy.

7. The method of claim 1, wherein the defined number of copies is two copies.

8. The method of claim 1, wherein the sample is a spatial sample, and wherein the sample is dissociated into a plurality of cells at step (e).

9. The method of claim 8, wherein each of the cell barcode probes further comprise a positional barcode different for at least some of the cell barcode probes.

10. The method of claim 8, wherein the cell barcode probes are delivered at step (c) from a spatially ordered array.

11. The method of claim 8, further comprising, after step (b), (i) delivering a plurality of positional probes to the permeabilized cells and/or nuclei, wherein a given positional probe comprises a common targeting element configured to be attached to the macromolecules and a positional barcode different for each positional probes; and (ii) attaching positional probes from the plurality of positional probes to the macromolecules.

12. The method of claim 11, wherein each of the amplified cell barcodes comprises a common region that is configured to hybridize to a region in the positional probes; and the method further comprises a step of performing a primer extension reaction to transfer the amplified cell barcodes to the positional probes attached to the macromolecules.

13. The method of claim 11, wherein the plurality of positional probes is delivered from a spatially ordered array.

14. The method of claim 1, wherein each compartment of the plurality of compartments comprises a compartment barcode configured to be attached to the macromolecules.

15. The method of claim 1, wherein during partitioning the cells and/or nuclei into the plurality of compartments at step (e), on average no more than one cell or nucleus comprising a cell barcode probe is comprised within a single compartment.

16. A method for barcoding macromolecules from a sample comprising a population of cells, the method comprising the following steps:
   a) permeabilizing cells, and/or nuclei of the cells, from the population of cells of the sample;
   b) delivering reactive primers that are configured to be covalently attached to components of the permeabilized cells and/or nuclei, thereby creating a plurality of attached primers;

c) optionally making genomic DNA of the permeabilized cells and/or nuclei at least partially accessible to nucleic acid hybridization;

d) delivering cell barcode probes to the permeabilized cells and/or nuclei of the permeabilized cells, wherein a given cell barcode probe comprises a genome binding element shared among the cell barcode probes, and a cell barcode unique for the given cell barcode probe, and wherein the genome binding element hybridizes to a region in the genomic DNA, thereby forming a nucleic acid duplex between the genome binding element and the region of the genomic DNA in the cells and/or nuclei;

e) removing cell barcode probes that are not bound to the genomic DNA from the cells and/or nuclei, whereby no more than a defined number of copies of the cell barcode probe remain in each cell or nucleus; and f) amplifying the cell barcodes using the plurality of attached primers, thereby forming amplified cell barcodes within the cells and/or nuclei, wherein nucleic acid recording tags are covalently attached to macromolecules or derivatives thereof within the cells and/or nuclei, and wherein the amplified cell barcodes or complements thereof are attached to the nucleic acid recording tags, thereby attaching the amplified cell barcodes or complements thereof to the macromolecules or derivatives thereof to form barcoded macromolecules or derivatives thereof.

17. The method of claim 16, wherein amplifying the cell barcodes at step (f) comprises providing conditions for hybridization between the cell barcode probes and the plurality of attached primers.

18. The method of claim 16, wherein the defined number of copies is one copy.

19. The method of claim 16, wherein the region in the genomic DNA is a non-repetitive region.

20. A method for barcoding macromolecules from a sample comprising a population of cells, the method comprising the following steps:
   a) permeabilizing cells, and/or nuclei of the cells, from the population of cells of the sample;
   b) delivering a specific genomic DNA-binding carrier comprising a cell barcode probe to the permeabilized cells and/or nuclei, wherein a given cell barcode probe comprises a cell barcode unique for each cell or nucleus, and a priming site, and wherein the specific genomic DNA-binding carrier specifically binds to a region in the genomic DNA of the cells and/or nuclei;
   c) removing specific genomic DNA-binding carriers that are not bound to the genomic DNA from the cells and/or nuclei, whereby no more than a defined number of copies of the cell barcode probe remain in each cell or nucleus; and
   d) amplifying the cell barcodes that were not removed from the cells and/or nuclei at step (c), thereby forming amplified cell barcodes,
   wherein nucleic acid recording tags are covalently attached to macromolecules or derivatives thereof within the cells and/or nuclei, and
   wherein the amplified cell barcodes or complements thereof are attached to the nucleic acid recording tags,
   thereby attaching the amplified cell barcodes or complements thereof to the macromolecules or derivatives thereof to form barcoded macromolecules or derivatives thereof.

21. The method of claim 20, wherein step (d) comprises the following steps:
   (i) partitioning the cells and/or nuclei into a plurality of compartments;
   (ii) amplifying the cell barcodes within compartments of the plurality of compartments, thereby forming amplified cell barcodes within the compartments.

22. The method of claim 20, wherein the defined number of copies is one copy.

* * * * *

SEQUENCE LISTING

```
Sequence total quantity: 11
SEQ ID NO: 1            moltype = DNA  length = 40
FEATURE                 Location/Qualifiers
misc_feature            1..40
                        note = GBS portion of CBP probe
source                  1..40
                        mol_type = other DNA
                        organism = synthetic construct
SEQUENCE: 1
tggccaggag gagactcttc caggtctccc ttctgacacc                40

SEQ ID NO: 2            moltype = DNA  length = 40
FEATURE                 Location/Qualifiers
misc_feature            1..40
                        note = GBS portion of CBP probe
source                  1..40
                        mol_type = other DNA
                        organism = synthetic construct
SEQUENCE: 2
aaaccttgcc aaccatgagt ttctgggact gacggtgatg                40

SEQ ID NO: 3            moltype = DNA  length = 20
FEATURE                 Location/Qualifiers
misc_feature            1..20
                        note = Model dTALE binding region
source                  1..20
                        mol_type = other DNA
                        organism = synthetic construct
SEQUENCE: 3
gagtttctgg gactgacggt                                      20
```

| | | |
|---|---|---|
| SEQ ID NO: 4 | moltype = AA   length = 969 | |
| FEATURE | Location/Qualifiers | |
| REGION | 1..969 | |
| | note = Model dTALE protein | |
| source | 1..969 | |
| | mol_type = protein | |
| | organism = synthetic construct | |
| SEQUENCE: 4 | | |

```
MGPLCTPSRS SHHHHHHSSG LVPRGSHMLD TSLLDSMPAV GTPHTAAAPA ECDEVQSGLR    60
AADDPPPTVR VAVTAARPPR AKPAPRRRAA QPSDASPAAQ VDLRTLGYSQ QQQEKIKPKV   120
RSTVAQTYQD IIRALPEATH EDIVGVGKQW SGARALEALL TEAGELRGPP LQLDTGQLLK   180
IAKRGGVTAV EAVHAWRNAL TGAPLNLTPD QVVAIASNIG GKQALETVQR LLPVLCQDHG   240
LTPDQVVAIA SNNGGKQALE TVQRLLPVLC QDHGLTPDQV VAIASNIGGK QALETVQRLL   300
PVLCQDHGLT PDQVVAIASN NGGKQALETV QRLLPVLCQD HGLTPDQVVA IASNGGGKQA   360
LETVQRLLPV LCQDHGLTPD QVVAIASNGG KQALETVQR LLPVLCQDHG LTPDQVVAIA    420
SNGGGKQALE TVQRLLPVLC QDHGLTPDQV VAIASHDGGK QALETVQRLL PVLCQDHGLT   480
PDQVVAIASN GGGKQALETV QRLLPVLCQD HGLTPDQVVA IASNNGGKQA LETVQRLLPV   540
LCQDHGLTPD QVVAIASNNG GKQALETVQR LLPVLCQDHG LTPDQVVAIA SNNGGKQALE   600
TVQRLLPVLC QDHGLTPDQV VAIASNIGGK QALETVQRLL PVLCQDHGLT PDQVVAIASH   660
DGGKQALETV QRLLPVLCQD HGLTPDQVVA IASNGGGKQA LETVQRLLPV LCQDHGLTPD   720
QVVAIASNNG GKQALETVQR LLPVLCQDHG LTPDQVVAIA SNIGGKQALE TVQRLLPVLC   780
QDHGLTPDQV VAIASHDGGK QALETVQRLL PVLCQDHGLT PDQVVAIASN NGGKQALETV   840
QRLLPVLCQD HGLTPDQVVA IASNNGGKQA LETVQRLLPV LCQDHGLTPD QVVAIASNGG   900
GKQALESIVA QLSRPDPALA ALTNDHLVAL ACLGGRPALD AVKKGLPHAP ELIRRINRRI   960
PERTSHRVA                                                          969
```

| | | |
|---|---|---|
| SEQ ID NO: 5 | moltype = DNA   length = 40 | |
| FEATURE | Location/Qualifiers | |
| misc_feature | 1..40 | |
| | note = iFISH probe | |
| source | 1..40 | |
| | mol_type = other DNA | |
| | organism = synthetic construct | |
| SEQUENCE: 5 | | |
| tggccaggag gagactcttc caggtctccc ttctgacacc | | 40 |

| | | |
|---|---|---|
| SEQ ID NO: 6 | moltype = DNA   length = 20 | |
| FEATURE | Location/Qualifiers | |
| misc_feature | 1..20 | |
| | note = GBS proximity probe | |
| source | 1..20 | |
| | mol_type = other DNA | |
| | organism = synthetic construct | |
| SEQUENCE: 6 | | |
| tggccaggag gagactcttc | | 20 |

| | | |
|---|---|---|
| SEQ ID NO: 7 | moltype = DNA   length = 20 | |
| FEATURE | Location/Qualifiers | |
| misc_feature | 1..20 | |
| | note = GBS proximity probe | |
| misc_feature | 1 | |
| | note = 5'-phosphorylated | |
| source | 1..20 | |
| | mol_type = other DNA | |
| | organism = synthetic construct | |
| SEQUENCE: 7 | | |
| caggtctccc ttctgacacc | | 20 |

| | | |
|---|---|---|
| SEQ ID NO: 8 | moltype = DNA   length = 20 | |
| FEATURE | Location/Qualifiers | |
| misc_feature | 1..20 | |
| | note = GBS proximity probe | |
| source | 1..20 | |
| | mol_type = other DNA | |
| | organism = synthetic construct | |
| SEQUENCE: 8 | | |
| aaaccttgcc aaccatgagt | | 20 |

| | | |
|---|---|---|
| SEQ ID NO: 9 | moltype = DNA   length = 20 | |
| FEATURE | Location/Qualifiers | |
| misc_feature | 1..20 | |
| | note = GBS proximity probe | |
| misc_feature | 1 | |
| | note = 5'-phosphorylated | |
| source | 1..20 | |
| | mol_type = other DNA | |
| | organism = synthetic construct | |
| SEQUENCE: 9 | | |
| ttctgggact gacggtgatg | | 20 |

```
SEQ ID NO: 10          moltype = DNA  length = 20
FEATURE                Location/Qualifiers
source                 1..20
                       mol_type = other DNA
                       organism = synthetic construct
misc_feature           1..20
                       note = P5 primer
SEQUENCE: 10
aatgatacgg cgaccaccga                                                 20

SEQ ID NO: 11          moltype = DNA  length = 24
FEATURE                Location/Qualifiers
source                 1..24
                       mol_type = other DNA
                       organism = synthetic construct
misc_feature           1..24
                       note = P7 primer
SEQUENCE: 11
caagcagaag acggcatacg agat                                            24
```